United States Patent
Inoue et al.

(10) Patent No.: US 9,718,771 B2
(45) Date of Patent: Aug. 1, 2017

(54) ANILINE DERIVATIVE, PHARMACEUTICAL COMPOSITION CONTAINING SAME, AND USE THEREOF

(71) Applicant: Kissei Pharmaceutical Co., Ltd., Matsumoto-shi, Nagano (JP)

(72) Inventors: Hitoshi Inoue, Joetsu (JP); Kohsuke Ohno, Azumino (JP); Tetsuya Nakamura, Matsumoto (JP); Yusuke Ohsawa, Azumino (JP)

(73) Assignee: KISSEI PHARMACEUTICAL CO., LTD., Matsumoto, Nagano (JP)

( * ) Notice: Subject to any disclaimer, the term of this patent is extended or adjusted under 35 U.S.C. 154(b) by 0 days.

(21) Appl. No.: 15/121,522

(22) PCT Filed: Feb. 27, 2015

(86) PCT No.: PCT/JP2015/055867
§ 371 (c)(1),
(2) Date: Aug. 25, 2016

(87) PCT Pub. No.: WO2015/129859
PCT Pub. Date: Sep. 3, 2015

(65) Prior Publication Data
US 2016/0362368 A1  Dec. 15, 2016

(30) Foreign Application Priority Data
Feb. 28, 2014 (JP) ................... 2014-037823

(51) Int. Cl.
C07D 205/04 (2006.01)
(52) U.S. Cl.
CPC .................. *C07D 205/04* (2013.01)
(58) Field of Classification Search
None
See application file for complete search history.

(56) References Cited

U.S. PATENT DOCUMENTS

| | | | |
|---|---|---|---|
| 7,855,193 B2 | 12/2010 | Saha et al. | |
| 7,919,519 B2 | 4/2011 | Burli et al. | |
| 8,080,542 B2 | 12/2011 | Neira et al. | |
| 8,592,399 B2 | 11/2013 | Gill et al. | |
| 8,791,100 B2 | 7/2014 | Angst et al. | |
| 9,193,716 B2 | 11/2015 | Gill et al. | |
| 2007/0173487 A1 | 7/2007 | Saha et al. | |
| 2008/0027036 A1 | 1/2008 | Burli et al. | |
| 2009/0082331 A1 | 3/2009 | Neira et al. | |
| 2010/0216762 A1 | 8/2010 | Harris et al. | |
| 2011/0059945 A1 | 3/2011 | Saha et al. | |
| 2011/0190258 A1 | 8/2011 | Angst et al. | |
| 2011/0212202 A1 | 9/2011 | Burli et al. | |
| 2011/0318388 A1 | 12/2011 | Gill et al. | |
| 2012/0088749 A1 | 4/2012 | Neira et al. | |

(Continued)

FOREIGN PATENT DOCUMENTS

| | | |
|---|---|---|
| JP | 2010-522162 A | 7/2010 |
| JP | 2010-540438 A | 12/2010 |
| JP | 2012-505836 A | 3/2012 |
| JP | 2012-517446 A | 8/2012 |
| JP | 2013-518846 A | 5/2013 |

OTHER PUBLICATIONS

Kunkel et al., Targeting the sphingosine-1-phosphate axis in cancer, inflammation and beyond. Nature Reviews Drug Discovery, 2013, 12, 688-702.*
Horig, H., Pullman, W. From bench to clinic and back: Perspective on the 1st IQPC Translational Research conference. Journal of Translational Medicine. Dec. 2004, 2, 44.*
Schafer, S., Kolkhof, P. Failure is an option: learning from unsuccessful proof-of-concept trials. Drug Discovery Today. Nov. 2008, 13, 913-916.*
International Search Report dated Apr. 21, 2015, issued in counterpart International Application No. PCT/JP2015/055867 (2 pages).

*Primary Examiner* — Matthew Coughlin
*Assistant Examiner* — Po-Chih Chen
(74) *Attorney, Agent, or Firm* — Westerman, Hattori, Daniels & Adrian, LLP

(57) ABSTRACT

A compound having an $S1P_1$ receptor antagonistic activity. A compound represented by general formula (I): (in the formula, $R^1$, $R^2$ and $R^3$ are each a hydrogen atom, a halogen atom, a $C_{1-6}$ alkyl group, a halo $C_{1-6}$ alkyl group or the like, $R^4$ is a $C_{1-6}$ alkyl group or the like, $R^5$ is a $C_{1-6}$ alkyl group or the like, $R^6$ is a $C_{1-6}$ alkyl group or the like, $R^7$ is a hydrogen atom, a halogen atom, a $C_{1-6}$ alkyl group or the like, $R^8$ is a halogen atom, a $C_{1-6}$ alkyl group, a halo $C_{1-6}$ alkyl group, a $C_{1-6}$ alkoxy group or the like, and $R^9$ is a hydrogen atom or a $C_{1-6}$ alkyl group.) or a pharmaceutically acceptable salt thereof, a pharmaceutical compositions containing same, and use thereof. The compounds have an excellent $S1P_1$ receptor antagonistic activity and are useful for the treatment or prevention of autoimmune diseases.

(I)

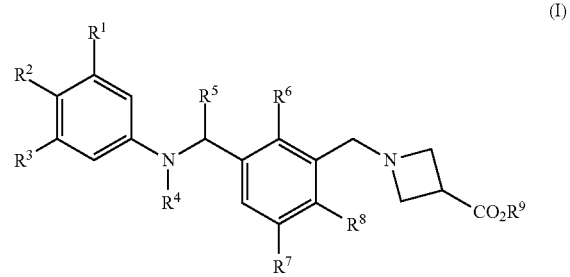

16 Claims, 1 Drawing Sheet

(56) References Cited

U.S. PATENT DOCUMENTS

2013/0035358 A1* 2/2013 Nilsson ............... C07D 213/50
514/338
2014/0066427 A1 3/2014 Gill et al.
2016/0038455 A1 2/2016 Gill et al.

* cited by examiner

ANILINE DERIVATIVE, PHARMACEUTICAL COMPOSITION CONTAINING SAME, AND USE THEREOF

TECHNICAL FIELD

The present invention relates to novel aniline derivatives having $S1P_1$ receptor antagonistic activities, pharmaceutical compositions containing the same, and use thereof.

BACKGROUND ART

Sphingosine-1-phosphate (S1P) is produced by the phosphorylation of sphingosine derived from sphingomyelin, which is a component of cell membranes, by sphingosine kinase. Conventionally, it has been considered that sphingosine-1-phosphate (S1P) is one of the metabolites of sphingolipids. In recent years, it was shown that it plays a role as intercellular messenger through the endothelial differentiation gene (Edg) receptor, which is a G protein-coupled receptor (for example, see Non-patent literature 1).

Edg receptors have been cloned eight subtypes of Edg-1 to 8 to date, and the specificity of S1P ligands differ depending on subtypes. Five subtypes of Edg-1, Edg-3, Edg-5, Edg-6 and Edg-8 are known in an S1P receptor, and also called $S1P_1$, $S1P_3$, $S1P_2$, $S1P_4$ and $S1P_5$, respectively (for example, see Non-patent literature 1).

From various studies on these S1P receptors, it has been reported that S1P receptor modulators exhibiting agonist activity or antagonist activity to these receptors are useful for a wide variety of disease.

Among these S1P receptors, an $S1P_1$ receptor is highly expressed on lymphocytes (T cells and B cells), and it has been considered that the $S1P_1$ receptor play an important role in the process where lymphocytes migrate from the secondary lymph node tissue such as lymph nodes from the research of mouse limitedly defected $S1P_1$ on lymphocytes (for example, see Non-patent literature 2).

It is known that fingolimod (FTY720), which is an agonist of an $S1P_1$ receptor, is converted to an active phosphorylated form (FTY720-P) by sphingosine kinase in vivo, shows a potent agonist action to the $S1P_1$ receptor and induces internalization and degradation of the $S1P_1$ receptor, and act as a functional antagonist. As a result, a migration of lymphocytes from secondary lymph tissues via the $S1P_1$ receptor is inhibited, and the body circulation of lymphocyte is regulated. It is known that fingolimod inhibits a migration from lymph nodes based on the same mechanism with respect to antigen-specific T cells including autoreactive T cells (for example, see Non-patent literature 3). Therefore, $S1P_1$ receptor agonists are considered to be useful as an agent for the treatment of autoimmune diseases, inflammatory bowel disease, acute or chronic rejection on allo- or xenogeneic tissue or organ transplantation, graft-versus-host disease and the like (for example, see Non-patent literature 4).

However, bradycardia, which is considered to be specific side effects associated with $S1P_1$ receptor agonists, is recognized in fingolimod and become problems (for example, see Non-patent literature 5).

It has been known that $S1P_1$ receptor antagonists have an inhibitory effect on a migration from the lymph node similar to $S1P_1$ receptor agonists as the result, by antagonizing S1P in vivo in the migration process of lymphocytes from secondary lymph node tissue (for example, see Non-patent literature 6). Therefore, $S1P_1$ receptor antagonists are considered to be useful as an agent for the treatment of autoimmune diseases, inflammatory bowel disease, acute or chronic rejection on allo- or xenogeneic tissue or organ transplantation, graft-versus-host disease and the like.

Also, $S1P_1$ receptor antagonists are considered to be useful as an agent for the treatment of age-related macular degeneration by inhibiting angiogenesis (for example, see Non-patent literature 7).

Also, $S1P_1$ receptor antagonists are considered to be useful as an agent for the treatment of cancer (for example, see Non-patent literature 8).

Therefore, a novel $S1P_1$ receptor antagonist having a potent $S1P_1$ receptor antagonistic activity and improved in bradycardia has been desired.

Patent literature 1 discloses a compound having an $S1P_1$ receptor antagonisitic activity represented by the general formula (V):

[Chem. 1]

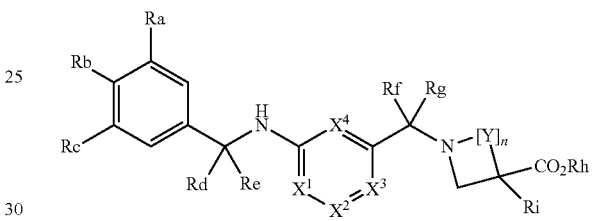

(V)

(see patent literature 1). However, a compound of the present invention represented by the general formula (I) is different from the compound represented by the general formula (V) in a chemical structure of the part binding two aromatic rings.

CITATION LIST

Patent Literature

Patent literature 1: International publication No. WO2011/095452

Non-Patent Literature

Non-patent literature 1: I. Ishii et "Annu. Rev. Biochem.", 2004, Vol. 73, pp. 321-354

Non-patent literature 2: S. R. Schwab et al., "Nat. Immunol.", 2007 Vol. 8, pp. 1295-1301

Non-patent literature 3: V. Brinkmaim et al., "Nat. Rev. Drug Discov.", 2010, Vol. 9, pp. 883-897

Non-patent literature 4: M. Maceyka et al., "Trends Cell Biol.", 2012, Vol. 22, pp. 50-60

Non-patent literature 5: D. Pelletier et al., "N. Engl. J. Med.", 2012, Vol. 366, pp. 339-347

Non-patent literature 6: Y. Fujii et al., "Biochim. Biophys. Acta.", 2012, Vol. 1821, pp. 600-606

Non-patent literature 7: V. Fujii et al., "Biochim. Biophys. Res. Commun.", 2012, Vol. 419, pp. 754-760

Non-patent literature 8: M. A. Ibrahim et al., "J. Med. Chem.", 2012, Vol. 55, pp. 1368-1381

SUMMARY OF THE INVENTION

Problem to be Solved by the Invention

An object of the present invention is to provide a novel compound having a potent $S1P_1$ receptor antagonistic activity, and preferably bradycardia is reduced.

Means for Solving the Problem

The present inventors have studied earnestly to solve the above problem. As a result, it was found surprisingly that compounds represented by the general formula (I) have highly potent antagonistic activities against $S1P_1$ receptor and have no bradycardia. Based on these findings, the present invention has been accomplished.

That is, the present invention relates to:
a compound represented by the general formula (I):

[Chem. 2]

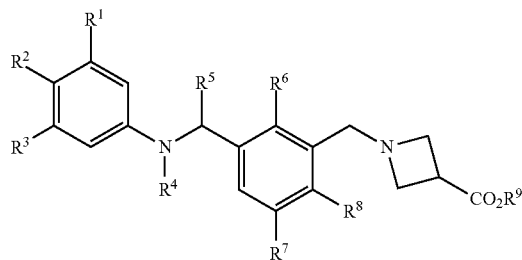

(I)

wherein
$R^1$, $R^2$ and $R^3$ are each independently any one of the following a) to f):
  a) a hydrogen atom,
  b) a halogen atom,
  c) a $C_{1-6}$ alkyl group,
  d) a halo $C_{1-6}$ alkyl group,
  e) a $C_{1-6}$ alkoxy group, or
  f) a cyano group;
$R^4$ is any one of the following a) to f):
  a) a $C_{1-6}$ alkyl group,
  b) a halo $C_{1-6}$ alkyl group,
  c) a cycloalkyl group,
  d) a cycloalkyl $C_{1-6}$ alkyl group,
  e) a $C_{1-6}$ alkoxy $C_{1-6}$ alkyl group, or
  f) a hydroxy $C_{1-6}$ alkyl group;
$R^5$ is any one of the following a) to c):
  a) a hydrogen atom,
  b) a $C_{1-6}$ alkyl group, or
  c) a hydroxy $C_{1-6}$ alkyl group;
$R^6$ is any one of the following a) to c):
  a) a hydrogen atom,
  b) a $C_{1-6}$ alkyl group, or
  c) a cyano group,
  or $R^5$ and $R^6$ combine to form $-(CH_2)_n-$;
$R^7$ and $R^8$ are each independently any one of the following a) to h):
  a) a hydrogen atom,
  b) a halogen atom,
  c) a $C_{1-6}$ alkyl group,
  d) a halo $C_{1-6}$ alkyl group,
  e) a $C_{1-6}$ alkoxy group,
  f) a hydroxy $C_{1-6}$ alkyl group,
  g) a $C_{2-6}$ alkenyl group, or
  h) a cyano group;
$R^9$ is a hydrogen atom or a $C_{1-6}$ alkyl group; and
n is 2 or 3, or a pharmaceutically acceptable salt thereof.

Also, the present invention relates to a pharmaceutical composition comprising a compound represented by the general formula (I) or a pharmaceutically acceptable salt thereof.

Also, the present invention relates to a pharmaceutical composition comprising a compound represented by the general formula (I) or a pharmaceutically acceptable salt thereof and at least one of a pharmaceutical additive.

Also, the present invention relates to an agent for the treatment or prevention of autoimmune diseases, inflammatory bowel disease, age-related macular degeneration, acute or chronic rejection on allo- or xenogeneic tissue or organ transplantation, graft-versus-host disease, or cancer comprising a compound represented by the general formula (I) or a pharmaceutically acceptable salt thereof.

Also, the present invention relates to a compound or a pharmaceutically acceptable salt thereof for the treatment or prevention of autoimmune diseases, inflammatory bowel disease, age-related macular degeneration, acute or chronic rejection on allo- or xenogeneic tissue or organ transplantation, graft-versus-host disease, or cancer.

Also the present invention relates to a method for the treatment or prevention of autoimmune diseases, inflammatory bowel disease, age-related macular degeneration, acute or chronic rejection on allo- or xenogeneic tissue or organ transplantation, graft-versus-host disease, or cancer comprising a step of administering an effective amount of a compound represented by the general formula (I) or a pharmaceutically acceptable salt thereof.

Also, the present invention relates to an $S1P_1$ receptor antagonist comprising a compound represented by the general formula (I) or a pharmaceutically acceptable salt thereof.

Also, the present invention relates to a pharmaceutical composition comprising a combination of a compound represented by the general formula (I) or a pharmaceutically acceptable salt thereof and any other immuno-suppressive drugs, inflammatory bowel disease treatment agents, anticancer agents or age-related macular degeneration treatment agents.

Effect of the Invention

The compounds of the present invention have a potent antagonistic activity against an $S1P_1$ receptor. Also, compounds of the present invention are not observed bradycardia and have a high safety. Therefore, compounds of the present invention are useful as an agent for the treatment or prevention of autoimmune diseases, inflammatory bowel disease, age-related macular degeneration, acute or chronic rejection on allo- or xenogeneic tissue or organ transplantation, graft-versus-host disease and cancer.

MODE FOR CARRYING OUT THE INVENTION

Figure 1:
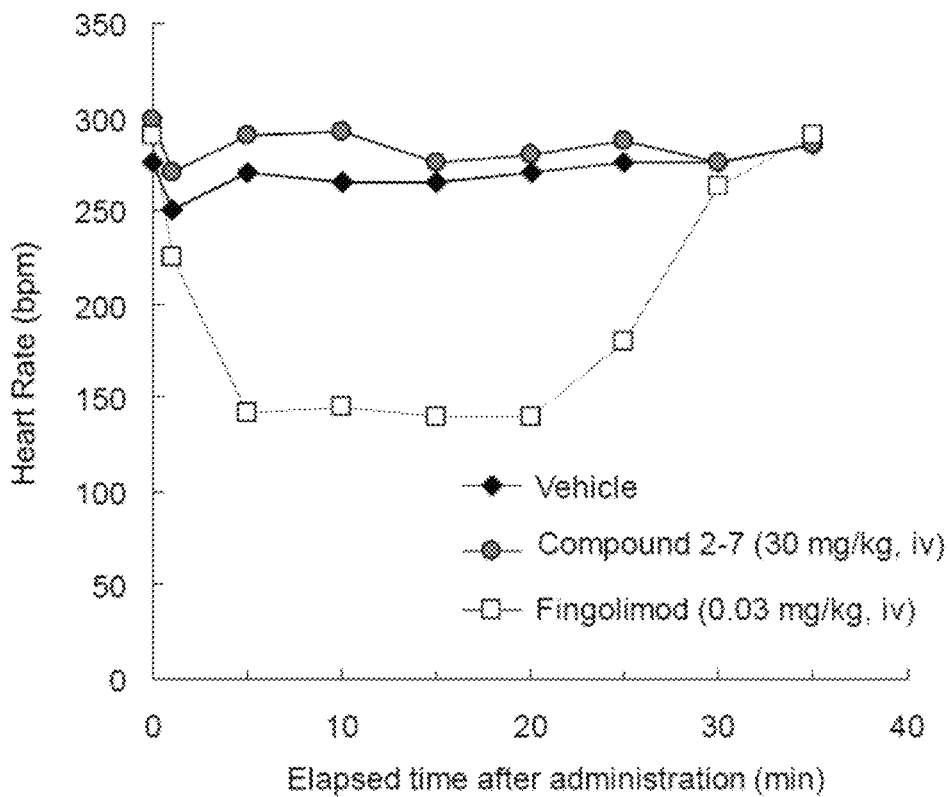
FIG. 1 is a figure showing results of confirmation test for reduction effects on heart rate shown in Test Example 3. The vertical axis represents a heart rate (bpm), and the horizontal axis represents an elapsed tune after administration (min).
Figure 2:
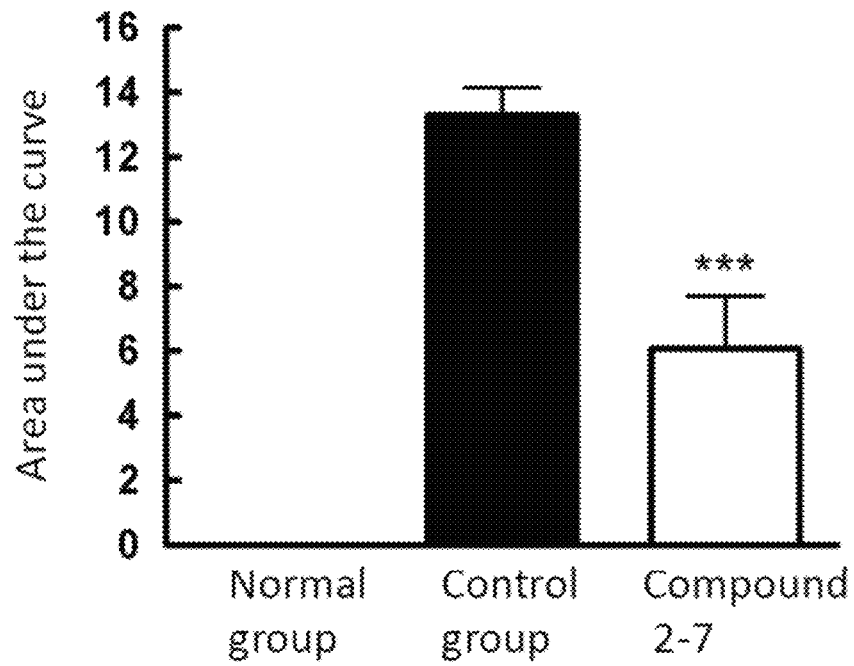
FIG. 2 is a figure showing results of examination in EAE model shown in Test Example 5. The vertical axis represents the area under the curve of EAE scores, and the horizontal axis represents the test compound groups.

In a compound represented by the general formula (I), the following terms have the following meanings unless otherwise specified.

The term "halogen atom" refers to a fluorine atom, a chlorine atom, a bromine atom or an iodine atom. In $R^1$, $R^2$ and $R^3$, a fluorine atom or a chlorine atom is preferable, and a chlorine atom is more preferable. In $R^7$ and $R^8$, a fluorine atom or a chlorine atom is preferable.

The term "$C_{1-6}$ alkyl group" refers to a straight chained or branched alkyl group having 1 to 6 carbon atoms, for example, a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group and the like can be illustrated. In $R^1$, $R^2$, $R^3$, $R^5$, $R^6$, $R^7$, $R^8$ and $R^9$, a $C_{1-3}$ alkyl group is preferable, and a methyl group is more preferable. In $R^4$, a $C_{1-4}$ alkyl group is preferable, a methyl group, an ethyl group, a propyl group or an isopropyl group is more preferable, and a methyl group or an ethyl group is more preferable.

The term "halo $C_{1-6}$ alkyl group" refers to an alkyl group having 1 to 6 carbon atoms substituted by the same or different 1 to 3 halogen atoms, for example, a fluoromethyl group, a 2-fluoroethyl group, a difluoromethyl group, a trifluoromethyl group, a 2,2,2-trifluoroethyl group, a 3,3,3-trifluoropropyl group, a 4,4,4-trifluorobutyl group and the like can be illustrated. In $R^1$, $R^2$, $R^3$, $R^7$ and $R^8$, a halo $C_{1-3}$ alkyl group is preferable, and a trifluoromethyl group is more preferable. In $R^4$, a halo $C_{1-3}$ alkyl group is preferable, and 2,2,2-trifluoroethyl group is more preferable.

The term "$C_{1-6}$ alkoxy group" refers to a straight chained or branched alkoxy group having 1 to 6 carbon atoms, for example, a methoxy group, an ethoxy group, a propoxy group, an isopropoxy group, a butoxy group, an isobutoxy group, a sec-butoxy group, a tert-butoxy group, a pentyloxy group, a hexyloxy group and the like can be illustrated, a $C_{1-3}$ alkoxy group is preferable, and a methoxy group is more preferable.

The term "cycloalkyl group" refers to a 3- to 7-membered saturated cyclic hydrocarbon, for example, a cyclopropyl group, a cyclobutyl group, a cyclopentyl group, a cyclohexyl group and a cycloheptyl group can be illustrated, and a cyclobutyl group is preferable.

As "cycloalkyl $C_{1-6}$ alkyl group", for example, as cyclopropylmethyl group, a cyclobutylmethyl group, a cyclopentylmethyl group, a cyclohexylmethyl group and the like can be illustrated, and a cyclopropylmethyl group is preferable.

As "$C_{1-6}$ alkoxy $C_{1-6}$ alkyl group", for example, a 2-methoxyethyl group, a 3-methoxypropyl group, an 2-ethoxyethyl group, an 3-ethoxypropyl group and the like can be illustrated, a $C_{1-3}$ alkoxy $C_{1-3}$ alkyl group is preferable, and a 2-methoxyethyl group is more preferable.

The term "hydroxy $C_{1-6}$ alkyl group" refers to an alkyl group having 1 to 6 carbon atoms substituted by a hydroxy group, for example a hydroxymethyl group, a 1-hydroxyethyl group, a 1-hydroxy-1,1-dimethylmethyl group, a 2-hydroxyethyl group, a 2-hydroxy-2-methylpropyl group, a 3-hydroxypropyl group and the like can be illustrated. In $R^4$, a hydroxy $C_{1-3}$ alkyl group is preferable, and a 1-hydroxy-ethyl group is more preferable. In $R^5$, $R^7$ and $R^8$, a hydroxy $C_{1-3}$ alkyl group is preferable, and a hydroxymethyl group is more preferable.

The term "$C_{2-6}$ alkenyl group" refers to a straight chained or branched unsaturated hydrocarbon group having 2 to 6 carbon atoms and at least one double bond, for example, $CH_2=CH-$, $CH_2=CHCH_2-$, $CH_2=CHCH_2CH_2-$, $CH_3CH=CHCH_2-$ and the like can be illustrated, and $CH_2=CH-$ is preferable.

The term "carbonyl compound" refers to a straight chained or branched aldehyde or ketone having 1 to 6 carbon atoms which may be substituted by the group selected from a halogen atom, a cycloalkyl group, a $C_{1-6}$ alkoxy group and a hydroxy group, or 3 to 7-membered cyclic ketone, for example, formaldehyde, acetoaldehyde, hydroxyacetoaldehyde, methoxyacetoaldehyde, trifluoroacetoaldehyde, propionaldehyde, cyclopropanecarbaldehyde, acetone, cyclobutanone and the like can be illustrated.

In the case where a compound represented by the general formula (I) of the present invention contains one or more asymmetric carbon atoms, all stereoisomers in the R- or S-configuration at each of asymmetric carbons and their mixtures are included in the scope of the present invention. In such cases, racemic compounds, racemic mixtures, racemic solid solutions, individual enantiomers and mixtures of diastereomers are included in the scope of the present invention. In the case where a compound represented by the general formula (I) has the geometrical isomers, all geometrical isomers are included in the scope of the present invention. In the case where a compound represented by the general formula (I) has the atropisomers, all atropisomers are included in the scope of the present invention. Moreover a compound represented by the general formula (I) also includes a hydrate and a solvate with a pharmaceutically acceptable solvent such as ethanol and the like.

Compounds represented by the general formula (I) of the present invention can exist in the form of salts. As such a salt, an acid additive salt with a mineral acid such as hydrochloric acid, hydrobromic acid, hydroiodic acid, sulfuric acid, nitric acid, phosphoric acid and the like; an acid additive salt with an organic acid such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; a salt with an inorganic base such as a lithium salt, a sodium salt, a potassium salt, a calcium salt, a magnesium salt and the like; a salt with organic base such as triethylamine, piperidine, morpholine, lysine and the like can be illustrated.

In one embodiment of a compound represented by the general formula (I) of the present invention, $R^1$, $R^2$ and $R^3$ are preferably each independently any one of the following a) to e):
  a) a hydrogen atom,
  b) a halogen atom,
  c) a $C_{1-6}$ alkyl group,
  d) a halo $C_{1-6}$ alkyl group, or
  e) a cyano group;
more preferably, $R^1$ and $R^2$ are each independently any one of the following a) to d):
  a) a halogen atom;
  b) a $C_{1-6}$ alkyl group,
  c) a halo $C_{1-6}$ alkyl group, or
  d) a cyano group;
$R^3$ is a hydrogen atom;

more preferably, $R^1$ and $R^2$ are each independently any one of the following a) to c):
a) a halogen atom,
b) a $C_{1-6}$ alkyl group, or
c) a halo $C_{1-6}$ alkyl group,
$R^3$ is a hydrogen atom;
$R^4$ is preferably a $C_{1-6}$ alkyl group or a hydroxy $C_{1-6}$ alkyl group,
more preferably, $R^4$ is a $C_{1-6}$ alkyl group;
preferably, $R^5$ is any one of the following a) to c):
a) a hydrogen atom,
b) a $C_{1-6}$ alkyl group, or
c) a hydroxy $C_{1-6}$ alkyl group;
$R^6$ is a hydrogen atom or a $C_{1-6}$ alkyl group, or
$R^5$ and $R^6$ combine to form $—(CH_2)_n—$,
more preferably, $R^5$ is a $C_{1-6}$ alkyl group;
$R^6$ is a hydrogen atom or a $C_{1-6}$ alkyl group, or
$R^5$ and $R^6$ combine to form $—(CH_2)_n—$;
$R^7$ and $R^8$ are preferably each independently any one of the following a) to g):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group, or
g) a $C_{2-6}$ alkenyl group,
more preferably, $R^7$ is a hydrogen atom,
$R^8$ is any one of the following a) to f):
a) a halogen atom,
b) a $C_{1-6}$ alkyl group,
c) a halo $C_{1-6}$ alkyl group,
d) a $C_{1-6}$ alkoxy group,
e) a hydroxy $C_{1-6}$ alkyl group, or
f) a $C_{2-6}$ alkenyl group,
more preferably, $R^7$ is a hydrogen atom,
$R^8$ is any one of the following a) to c):
a) a halogen atom,
b) a $C_{1-6}$ alkyl group, or
c) a halo $C_{1-6}$ alkyl group.
$R^9$ is preferably a hydrogen atom, or
n is preferably 2.
In a preferable embodiment of the present invention,
$R^7$ and $R^8$ are each independently any one of the following a) to g):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group, or
g) a $C_{2-6}$ alkenyl group.
In a more preferable embodiment of the present invention,
$R^1$, $R^2$ and $R^3$ are each independently any one of the following a) to e):
a) a hydrogen atom,
b) a halogen atom,
c) a $C_{1-6}$ alkyl group,
d) a halo $C_{1-6}$ alkyl group, or
e) a cyano group.
$R^7$ and $R^8$ are each independently any one of the following a) to g):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group, or
g) a $C_{2-6}$ alkenyl group.
In an even more preferable embodiment of the present invention,
$R^1$, $R^2$ and $R^3$ are each independently any one of the following a) to e):
a) a hydrogen atom,
b) a halogen atom,
c) a $C_{1-6}$ alkyl group,
d) a halo $C_{1-6}$ alkyl group, or
e) a cyano group,
$R^4$ is a $C_{1-6}$ alkyl group or a hydroxy $C_{1-6}$ alkyl group,
$R^7$ and $R^8$ are each independently any one of the following a) to g):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group, or
g) a $C_{2-6}$ alkenyl group.
In an even more preferable embodiment of the present invention,
$R^1$, $R^2$ and $R^3$ are each independently any one of the following a) to e):
a) a hydrogen atom,
b) a halogen atom,
c) a $C_{1-6}$ alkyl group,
d) a halo $C_{1-6}$ alkyl group, or
e) a cyano group.
$R^4$ is a $C_{1-6}$ alkyl group or a hydroxy $C_{1-6}$ alkyl group,
$R^5$ is any one of the following a) to c):
a) a hydrogen atom,
b) a $C_{1-6}$ alkyl group, or
c) a hydroxy $C_{1-6}$ alkyl group.
$R^6$ is any one of the following a) to b):
a) a hydrogen atom, or
b) a $C_{1-6}$ alkyl group,
or $R^5$ and $R^6$ combine to form $—(CH_2)_n—$,
$R^7$ and $R^8$ are each independently any one of the following a) to g):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group, or
g) a $C_{2-6}$ alkenyl group.
In an even more preferable embodiment of the present invention,
$R^1$, $R^2$ and $R^3$ are each independently any one of the following a) to e):
a) a hydrogen atom,
b) a halogen atom,
c) a $C_{1-6}$ alkyl group,
d) a halo $C_{1-6}$ alkyl group, or
e) a cyano group,
$R^4$ is a $C_{1-6}$ alkyl group,
$R^5$ is any one of the following a) to c):
a) a hydrogen atom,
b) a $C_{1-6}$ alkyl group, or
c) a hydroxy $C_{1-6}$ alkyl group,
$R^6$ is any one of the following a) to b):
a) a hydrogen atom, or
b) a $C_{1-6}$ alkyl group,
or $R^5$ and $R^6$ combine to form $—(CH_2)_n—$, $R^7$ and $R^8$ are each independently any one of the following a) to g):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group, or
g) a $C_{2-6}$ alkenyl group.

In an even more preferable embodiment of the present invention,
$R^1$, $R^2$ and $R^3$ are each independently any one of the following a) to e):
a) a hydrogen atom,
b) a halogen atom,
c) a $C_{1-6}$ alkyl group,
d) a halo $C_{1-6}$ alkyl group, or
e) a cyano group,
$R^4$ is a $C_{1-6}$ alkyl group,
$R^5$ is any one of the following a) to c):
a) a hydrogen atom,
b) a $C_{1-6}$ alkyl group, or
c) a hydroxy $C_{1-6}$ alkyl group,
$R^6$ is any one of the following a) to b):
a) a hydrogen atom, or
b) a $C_{1-6}$ alkyl group,
or $R^5$ and $R^6$ combine to form —$(CH_2)_n$—,
$R^7$ is a hydrogen atom,
$R^8$ is any one of the following a) to f):
a) a halogen atom,
b) a $C_{1-6}$ alkyl group,
c) a halo $C_{1-6}$ alkyl group,
d) a $C_{1-6}$ alkoxy group,
e) a hydroxy $C_{1-6}$ alkyl group, or
f) a$C_{2-6}$ alkenyl group.

In an even more preferable embodiment of the present invention,
$R^1$ and $R^2$ are each independently any one of the following a) to d):
a) a halogen atom,
b) a $C_{1-6}$ alkyl group,
c) a halo $C_{1-6}$ alkyl group, or
d) a cyano group:
$R^3$ is a hydrogen atom,
$R^4$ is a $C_{1-6}$ alkyl group,
$R^5$ is any one of the following a) to c):
a) a hydrogen atom,
b) a $C_{1-6}$ alkyl group, or
c) a hydroxy $C_{1-6}$ alkyl group,
$R^6$ is any one of the following a) to b):
a) a hydrogen atom, or
b) a $C_{1-6}$ alkyl group,
or $R^5$ and $R^6$ combine to form —$(CH_2)_n$—,
$R^7$ is a hydrogen atom,
$R^8$ is any one of the following a) to f):
a) a halogen atom,
b) a $C_{1-6}$ alkyl group,
c) a halo $C_{1-6}$ alkyl group,
d) a $C_{1-6}$ alkoxy group,
e) a hydroxy $C_{1-6}$ alkyl group, or
f) a $C_{2-6}$ alkenyl group.

In an even more preferable embodiment of the present invention,
$R^1$ and $R^2$ are each independently any one of the following, a) to d):
a) a halogen atom,
b) a $C_{1-6}$ alkyl group,
c) a halo $C_{1-6}$ alkyl group, or
d) a cyano group;
$R^3$ is a hydrogen atom.
$R^4$ is a $C_{1-6}$ alkyl group,
$R^5$ is a $C_{1-6}$ alkyl group,
$R^6$ is a hydrogen atom, or
$R^5$ and $R^6$ combine to form —$(CH_2)_n$—,
$R^7$ is a hydrogen atom,
$R^8$ is any one of the following a) to f):
a) a halogen atom,
b) a $C_{1-6}$ alkyl group,
c) a halo $C_{1-6}$ alkyl group,
d) a $C_{1-6}$ alkoxy group,
e) a hydroxy $C_{1-6}$ alkyl group, or
f) a $C_{2-6}$ alkenyl group.

In an even more preferable embodiment of the present invention,
$R^1$ and $R^2$ are each independently any one of the following a) to c):
a) a halogen atom,
b) a $C_{1-6}$ alkyl group, or
c) a halo $C_{1-6}$ alkyl group,
$R^3$ is a hydrogen atom,
$R^4$ is a $C_{1-6}$ alkyl group,
$R^5$ is a $C_{1-6}$ alkyl group,
$R^6$ is a hydrogen atom, or
$R^5$ and $R^6$ combine to form —$(CH_2)_n$—,
$R^7$ is a hydrogen atom,
$R^8$ is any one of the following a) to f):
a) a halogen atom,
b) a $C_{1-6}$ alkyl group,
c) a halo $C_{1-6}$ alkyl group,
d) a $C_{1-6}$ alkoxy group,
e) a hydroxy $C_{1-6}$ alkyl group, or
f) a $C_{2-6}$ alkenyl group.

In an even more preferable embodiment of the present invention,
$R^1$ and $R^2$ are each independently any one of the following a) to c):
a) a halogen atom,
b) a $C_{1-6}$ alkyl group, or
c) a halo $C_{1-6}$ alkyl group,
$R^3$ is a hydrogen atom,
$R^4$ is a $C_{1-6}$ alkyl group,
$R^5$ is a $C_{1-6}$ alkyl group,
$R^6$ is a hydrogen atom, or
$R^5$ and $R^6$ combine to form —$(CH_2)_n$—,
$R^7$ is a hydrogen atom,
$R^8$ is any one of the following a) to c):
a) a halogen atom,
b) a $C_{1-6}$ alkyl group, or
c) a halo $C_{1-6}$ alkyl group.

In these preferable embodiments, $R^9$ is preferably a hydrogen atom.

In these preferable embodiment, n is preferably 2.

Specific examples of preferred embodiments of the present invention are compounds selected form the group consisting of:

1-(5-{1-[(4-Chloro-3-methylphenyl)(ethyl)amino]ethyl}-2-methylbenzyl)azetidine-3-carboxylic acid (Compound 2-6);

1-(5-{1-[(4-Chloro-3-trifluoromethylphenyl)(ethyl)amino]ethyl}-2-methylbenzyl)azetidine-3-carboxylic acid (Compound 2-7);

1-{1-[(4-Chloro-3-trifluoromethylphenyl)(ethyl)amino]-5-methylindan-4-ylmethyl}azetidine-3-carboxylic acid (Compound 2-8);

1-{1-[(4-Chloro-3-trifluoromethylphenyl)(methyl)amino]-5-methylindan-4-ylmethyl}azetidine-3-carboxylic acid (Compound 2-10);
1-(5-{1-[(4-Chloro-3-methylphenyl)(propyl)amino]ethyl}-2-methylbenzyl)-azetidine-3-carboxylic acid (Compound 2-14);
1-{1-[(4-Chloro-3-methylphenyl)(ethyl)amino]-5-fluoroindan-4-ylmethyl}-azetidine-3-carboxylic acid (Compound 2-15);
1-{1-[(4-Chloro-3-methylphenyl)(ethyl)amino]-5-methylindan-4-ylmethyl}-azetidine-3-carboxylic acid (Compound 2-21);
1-(5-{1-[(4-Chloro-3-trifluommethylphenyl)(methyl)amino]ethyl}-2-methylbenzyl)azetidine-3-carboxylic acid (Compound 2-25);
1-(5-{1-[(4-Chloro-3-methylphenyl)(ethyl)amino]ethyl}-2-fluorobenzyl)-azetidine-3-carboxylic acid (Compound 2-31);
1-(2-Chloro-5-{1-[(4-chloro-3-methylphenyl)(ethyl)amino]ethyl}benzyl)-azetidine-3-carboxylic acid (Compound 2-32);
1-(2-Chloro-5-{1-[(4-chloro-3-trifluoromethylphenyl)(methyl)amino]-ethyl}benzyl)azetidine-3-carboxylic acid (Compound 2-33);
1-(2-Chloro-5-{1-[(4-chloro-3-tri fluoromethylphenyl)(ethyl)amino]ethyl}-benzyl)azetidine-3-carboxylic acid (Compound 2-34);
1-(5-{1-[(4-Chloro-3-trifluoromethylphenyl)(ethyl)amino]ethyl}-2-trifluoromethylbenzyl)azetidine-3-carboxylic acid (Compound 2-41);
1-(5-{1-[(4-Chloro-3-methylphenyl)(ethyl)amino]ethyl}-2-trifluoromethylbenzyl)azetidine-3-carboxylic acid (Compound 2-43);
1-(5-{1-[(4-Chloro-3-trifluoromethylphenyl)(ethyl)amino]propyl}-2-methylbenzyl)azetidine-3-carboxylic acid (Compound 2-45); and
1-(5-{1-[(4-Chloro-3-methylphenyl)(ethyl)amino]propyl}-2-methylbenzyl)-azetidine-3-carboxylic acid (Compound 2-46).

Compounds represented by the general formula (I) of the present invention can be prepared by methods as illustrated in schemes 1 to 7.

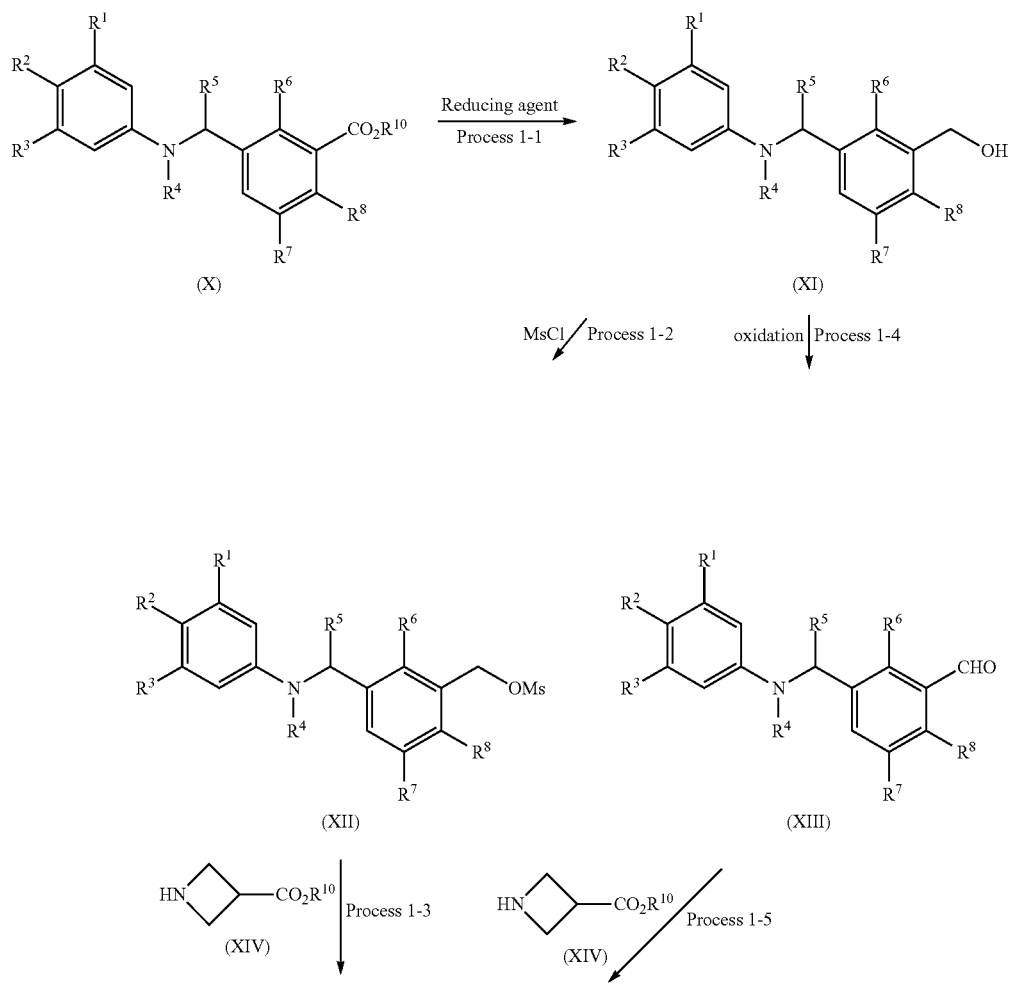

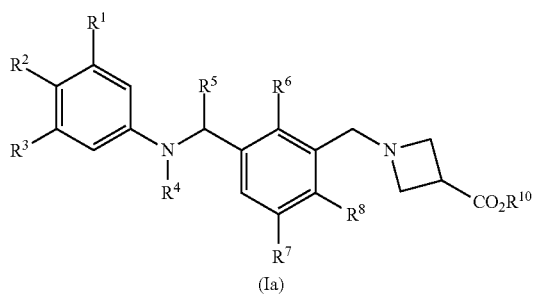

(Ia)

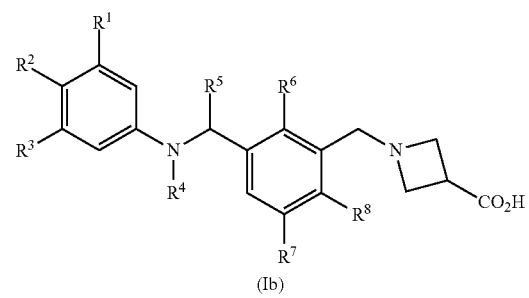

(Ib)

In the formula, $R^1$, $R^2$, $R^3$, $R^4$, $R^5$, $R^6$, $R^7$ and $R^8$ have the same meanings as defined above; and $R^{10}$ is a $C_{1-6}$ alkyl group, Ms represents methansulfonyl.

Process 1-1

Compound (XI) can be prepared by subjecting Compound (X) to reduction using a reducing agent (for example, lithium aluminum hydride, diisobutylaluminum hydride and the like) in an inert solvent (for example, tetrahydrofuran, diethyl ether and the like). The reaction temperature is usually at −78° C. to room temperature, and the reaction time is usually 10 minutes to 24 hours, varying based on the starting materials employed, the reaction temperature and the like.

Process 1-2

Compound (XII) can be prepared by treating Compound (XI) by using a mesylation agent (for example, mesyl chloride, methanesulfonic anhydride and the like) in the presence of a base (for example, triethylamine, pyridine and the like) in a suitable solvent (for example, tetrahydrofuran, methylene chloride and the like). The reaction temperature is usually at −78° C. to room temperature, and the reaction time is usually 10 minutes to 24 hours, varying based on the starting materials employed, the reaction temperature and the like.

Process 1-3

Compound (Ia) can be prepared by allowing Compound (XII) to react with Azetidine ester derivative (XIV) in the presence of a base (for example, N,N-diisopropylethylamine, triethylamine and the like) in an inert solvent (for example, tetrahydrofuran, acetonitrile, N,N-dimethylformamide and the like). The reaction can be carried out by adding sodium iodide, tetrabutyl ammonium iodide and the like as needed. The reaction temperature is usually at room temperature to reflux temperature, and the reaction time is usually 10 minuites to 24 hours, varying based on the starting materials employed, the reaction temperature and the like.

Further, Compound (Ia) can be also prepared by carrying out the reaction shown in the following Processes 1-4 and 1-5.

Process 1-4

Compound (XIII) can be prepared by subjecting Compound (XI) to oxidation using oxidizing agent (for example, Dess-Martin reagent, manganese dioxide and the like) in an inert solvent (for example, methylene chloride, benzene, ethyl acetate and the like). The reaction temperature is usually at −78° C. to reflux temperature, and the reaction time is usually 10 minutes to 1 week, varying based on the starting materials employed, the reaction temperature and the like.

Process 1-5

Compound (Ia) can be prepared by condensing Compound (XIII) and Azetidine ester derivative (XIV) in the presence of a reducing agent (for example, sodium triacetoxyborohydride, sodium borohydride, cyanoborohydride and the like) in a suitable solvent (for example, tetrahydrofuran, methylene chloride, N,N-dimethylformamide, methanol and the like). The reaction temperature is usually at 0° C. to reflux temperature, and the reaction time is usually 10 minutes to 24 hours, varying based on the starting materials employed, the reaction temperature and the like. The reaction can be carried out by adding an acid such as acetic acid, p-toluenesulfonic acid, methanesulfonic acid, sulfuric acid, hydrochloric acid and the like as needed.

Process 1-6

Compound (Ib) can be prepared by subjecting Compound (Ia) to hydrolysis using a base (for example, sodium hydroxide, lithium hydroxide, potassium hydroxide and the like) in a suitable solvent (for example, tetrahydrofuran, methanol, 1,4-dioxane, water and the like). The reaction temperature is usually at 0° C. to reflux temperature, and the reaction time is usually 10 minutes to 24 hours, varying based on the starting materials employed, the reaction temperature and the like.

Scheme 2

[Chem. 4]

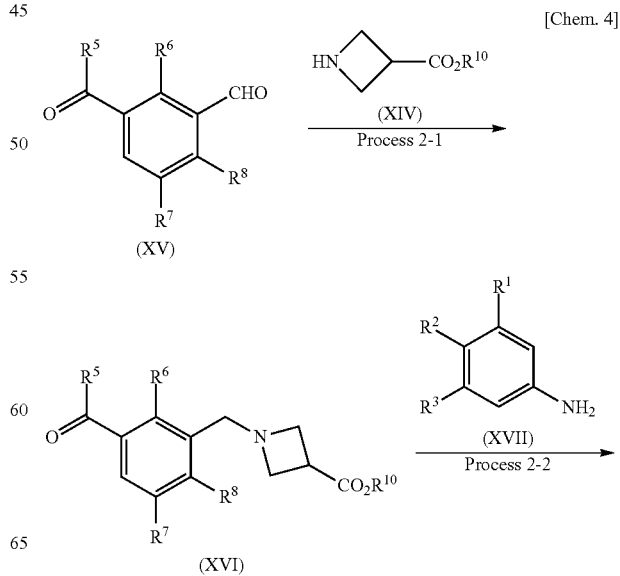

-continued

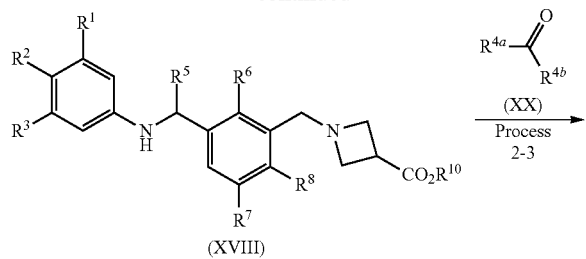

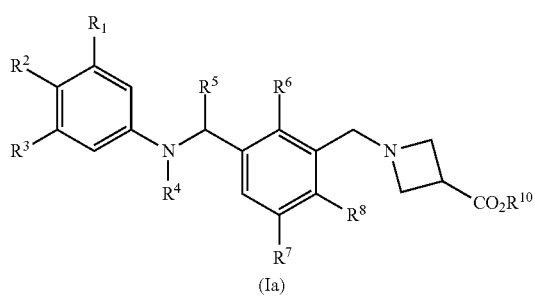

In the formula, $R^1$, $R^2$, $R^3$, $R^4$, $R^5$, $R^6$, $R^7$, $R^8$ and $R^{10}$ have the same meanings as defined above, and $R^{4a}$ C(O)$R^{4b}$ represents a carbonyl compound.

Process 2-1

Compound (XVI) can be prepared by condensing Compound (XV) and Azetidine ester derivative (XIV) in the presence of a reducing agent (for example, sodium triacetoxyborohydride, sodium borohydride, cyanoborohydride and the like) in a suitable solvent (for example, tetrahydrofuran, methylene chloride, N,N-dimethylformamide, methanol and the like). The reaction temperature is usually at 0° C. to relax temperature, and the reaction time is usually 10 minutes to 24 hours, varying based on the starting materials employed, the reaction temperature and the like. The reaction can be carried out by adding an acid such as acetic acid, p-toluenesulfonic acid, methanesulfonic acid, sulfuric acid, hydrochloric acid and the like as needed.

Process 2-2

Compound (XVIII) can be prepared by condensing Compound (XVI) and Aniline derivative (XVII) in the presence of as reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Process 2-3

Compound (Ia) can be prepared by condensing Compound (XVIII) and Carbonyl derivative (XX) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Scheme 3

[Chem. 5]

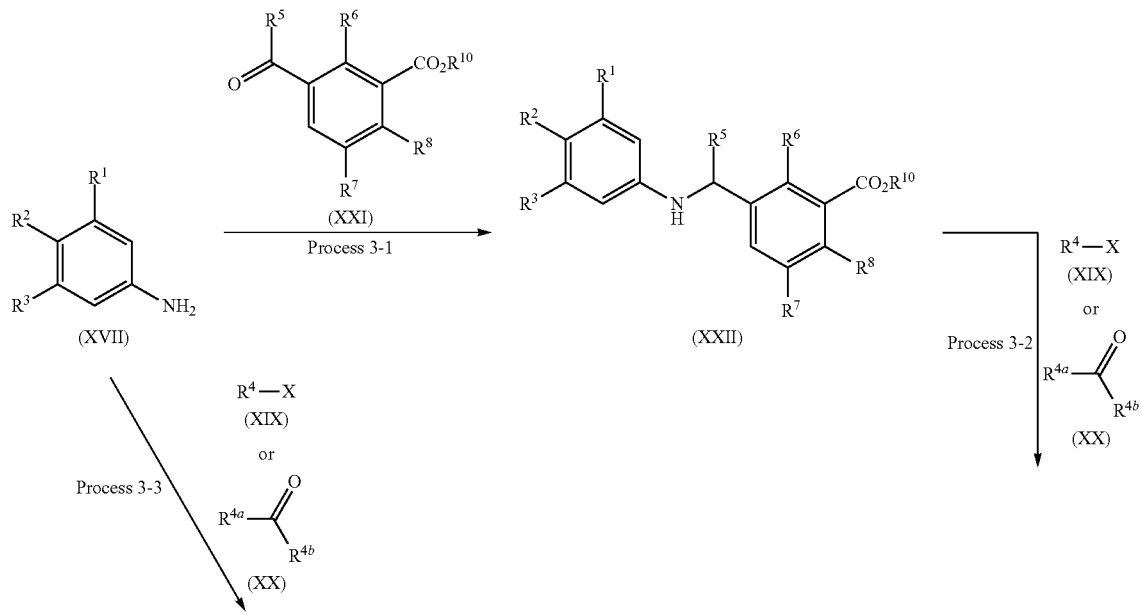

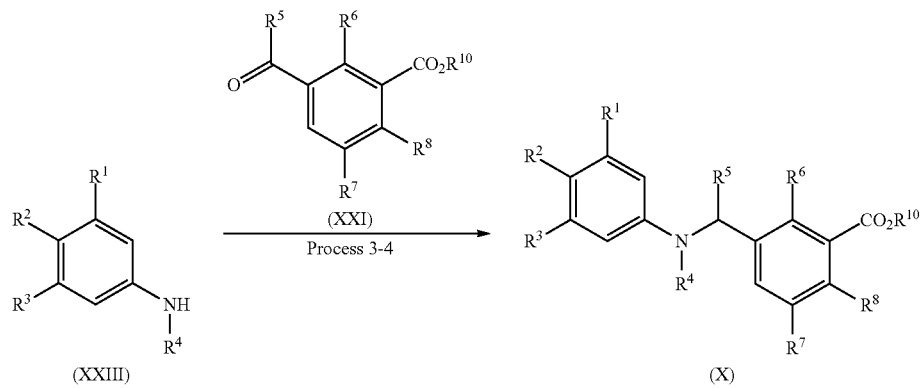

In the formula, $R^1$, $R^2$, $R^3$, $R^4$, $R^5$, $R^6$, $R^7$, $R^8$, $R^{10}$ and $R^{4a}C(O)R^{4b}$ have the same meanings as defined above, and X represents a leaving group such as chlorine, bromine, iodine, methanesulfonyloxy or the like.

Process 3-1

Compound (XXII) can be prepared by condensing Aniline derivative (XVII) and Carbonyl derivative (XXI) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Process 3-2

Compound (X) can be prepared by condensing Compound (XXII) and Carbonyl derivative (XX) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Also, Compound (X) can be prepared by condensing Compound (XXII) and an alkylating agent (XIX) in the presence of a base (for example, sodium hydride, potassium carbonate) in an inert solvent (for example, N,N-dimethylformamide, tetrahydrofuran and the like). The reaction temperature is usually at −78° C. to reflux temperature, and the reaction time is usually 10 minutes to 24 hours, varying based on the starting materials employed, the reaction temperature and the like.

Also, compound (X) can be also prepared by carrying out the reaction shown in the following Processes 3-3 and 3-4.

Process 3-3

Compound (XXIII) can be prepared by condensing Aniline derivative (XVII) and Carbonyl derivative (XX) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Also, Compound (XXIII) can be prepared by condensing Aniline derivative (XVII) and alkylating agent (XIX) in the presence of a base (for example, sodium hydride, potassium carbonate) in an inert solvent (for example, N,N-dimethylformamide, tetrahydrofuran and the like). The reaction temperature is usually at −78° C. to reflux temperature, and the reaction time is usually 10 minutes to 24 hours, varying based on the starting materials employed, the reaction temperature and the like.

Process 3-4

Compound (X) can be prepared by condensing Compound (XXIII) and Carbonyl derivative (XXI) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Scheme 4

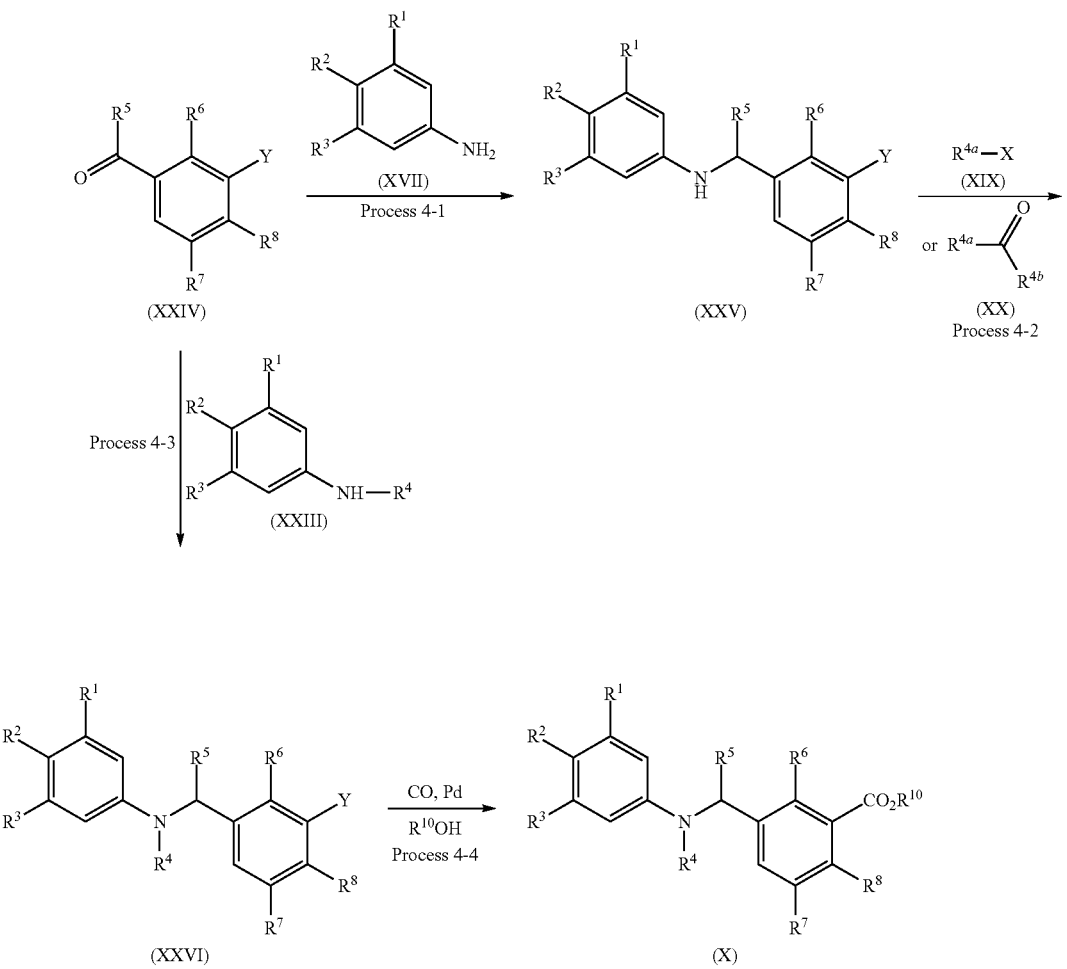

In the formula, $R^1$, $R^2$, $R^3$, $R^4$, $R^5$, $R^6$, $R^7$, $R^8$, $R^{10}$, X and $R^{4a}C(O)R^{4b}$ have the same meanings as defined above, and Y represents bromine or iodine.

Process 4-1

Compound (XXV) can be prepared by condensing Compound (XXIV) and Aniline derivative (XVII) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Process 4-2

Compound (XXVI) can be prepared by condensing Compound (XXV) and Carbonyl derivative (XX) in the presence of a base (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Also, Compound (XXVI) can be prepared by condensing Compound (XXV) and an alkylating agent (XIX) in the presence of a base (for example, sodium hydride, potassium carbonate) in an inert solvent (for example, N,N-dimethylformamide, tetrahydrofuran and the like). The reaction temperature is usually at −78° C. to reflux temperature, and the reaction time is usually 10 minutes to 24 hours, varying based on the starting materials employed, the reaction temperature and the like.

Process 4-3

Also, Compound (XXVI) can be also prepared by condensing Compound (XXIV) and Compound (XXIII) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Process 4-4

Compound (X) can be prepared by condensing Compound (XXVI) and $C_{1-6}$ alcohol in the presence of a palladium catalyst (for example, [1,1'-bis(diphenylphosphino)ferrocene]dichloropalladium, tetrakistriphenylphosphinepalladium, palladium acetate and the like), a phosphorus ligand (for example, 1,1'-bis(diphenylphosphino)ferrocene, triphenylphosphine and the like) and a base (for example, triethylamine, potassium carbonate, N,N-dimethylaminopyridine and the like) in an inert solvent (for example, N-methylpyrrolidone, N,N-dimethylformamide, toluene and the like) under a carbon monoxide atomosphere. The reaction temperature is usually at room temperature to reflux temperature, and the reaction time is usually 1 hour to 1 week, varying based on the starting materials employed, the reaction temperature and the like.

Scheme 5

[Chem. 7]

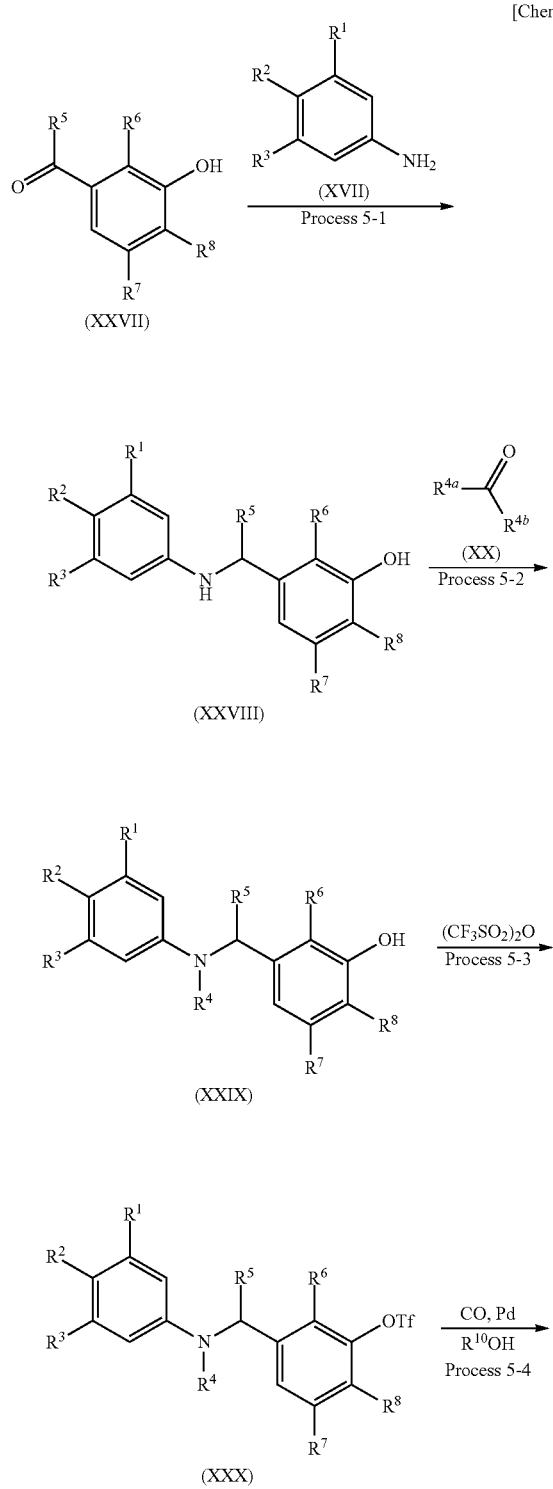

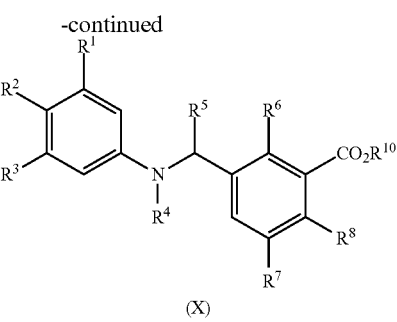

(X)

In the formula, $R^1$, $R^2$, $R^3$, $R^4$, $R^5$, $R^6$, $R^7$, $R^8$, $R^{10}$ and $R^{4a}C(O)R^{4b}$ have the same meanings as defined above, and Tf represents trifluoromethanesulfonyl.

Process 5-1

Compound (XXVIII) can be also prepared by condensing Compound (XXVII) and Aniline derivative (XVII) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Process 5-2

Compound (XXIX) can be prepared by condensing Compound (XXVIII) and Carbonyl derivative (XX) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Process 5-3

Compound (XXX) can be prepared by allowing Compound (XXIX) to react with trifluoromethanesulfonic anhydride in the presence of a base (for example, pyridine, triethylamine and the like) in an inert solvent (for example, methylene chloride, and tetra and the like). The reaction temperature is usually at −78° C. to room temperature, and the reaction time is usually 10 minutes to 24 hours, varying based on the starting materials employed, the reaction temperature and the like.

Process 5-4

Compound (X) can be prepared by condensing Compound (XXX) and $C_{1-6}$ alcohol in the presence of a palladium catalyst (for example, [1,1′-bis(diphenylphosphino)ferrocene]dichloropalladium, tetrakistriphenylphosphinepalladium, palladium acetate and the like), a phosphorus ligand (for example, 1,1′-bis(diphenylphosphino)ferrocene, triphenylphosphine and the like) and a base (for example, triethylamine, potassium carbonate, N,N-dimethylaminopyridine and the like) in an inert solvent (for example, N-methylpyrrolidone, N,N-dimethylformamide, toluene and the like) under a carbon monoxide atomosphere. The reaction temperature is usually at room temperature to reflux temperature, and the reaction time is usually 1 hour to 1 week, varying based on the starting materials employed, the reaction temperature and the like.

[Chem. 8]

Scheme 6

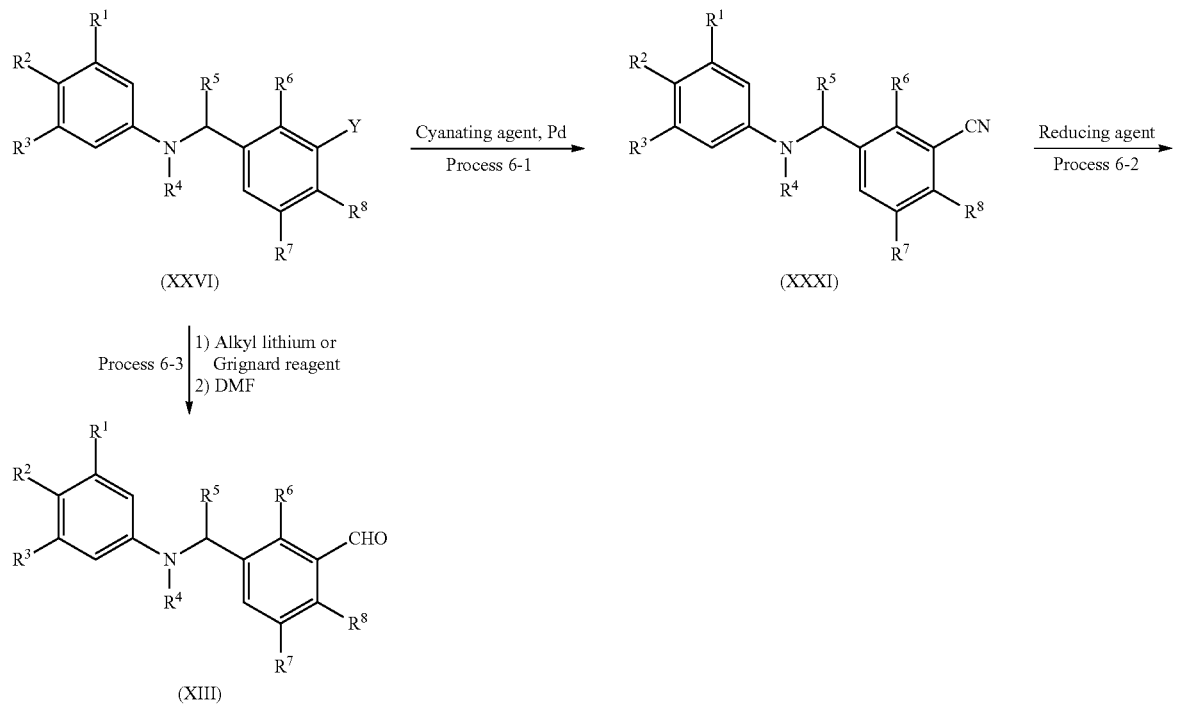

In the formula, $R^1$, $R^2$, $R^3$, $R^4$, $R^5$, $R^6$, $R^7$, $R^8$ and Y have the same meanings as defined above, and DMF represents N,N-dimethylformamide.

Process 6-1

Compound (XXXI) can be prepared by allowing Compound (XXVI) to react with a cyanating agent (for example, zinc cyanide, copper cyanide and the like) in the presence of a palladium catalyst (for example, [1,1'-bis(diphenylphosphino)ferrocene] dichloropalladiuin, tetrakistriphenylphosphine palladium, palladium acetate and the like) and a phosphorus ligand (for example, 1,1'-bis(diphenylphosphino)ferrocene, triphenylphosphine and the like) in an inert solvent (for example, N-methylpyrrolidone, N,N-dimethylformamide, toluene and the like). The reaction temperature is usually at room temperature to reflux temperature, and the reaction time is usually 1 hour to 1 week, varying based on the starting matetials employed, the reaction temperature and the like.

Process 6-2

Compound (XIII) can be prepared by subjecting Compound (XXXI) to reduction using a reducing agent (for example, diisobutylaluminum hydride and the like) in a suitable solvent (for example, methylene chloride, tetrahydrofuran, toluene and the like). The reaction temperature is usually at −78° C. to room temperature, and the reaction time is usually 10 minutes to 24 hours, varying based on the starting materials employed, the reaction temperature and the like.

Process 6-3

Also, Compound (XIII) can be also prepared by treating Compound (XXVI) with alkyl metal (for example, an alkyllithium such as n-butyl lithium or the like, Grignard reagent such as isopropyl magnesium bromide or the like and the like) in an inert solvent (for example, tetrahydrofuran, diethyl ether and the like) and subsequently treating it with N,N-dimethylformamide. The reaction temperature is usually at −78° C. to room temperature, and the reaction time is usually 1 hour to 24 hours, varying based on the starting materials employed, the reaction temperature and the like.

Scheme 7

[Chem. 9]

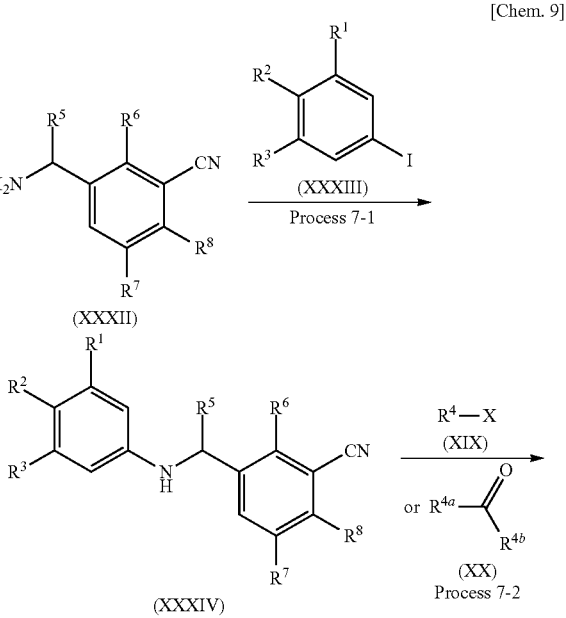

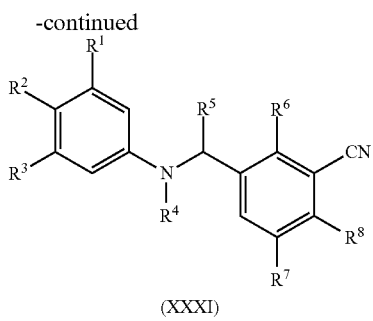

(XXXI)

In the formula, $R^1$, $R^2$, $R^3$, $R^4$, $R^5$, $R^6$, $R^7$, $R^8$, X and $R^{4a}C(O)R^{4b}$ have the same meanings as defined above.

Process 7-1

Compound (XXXIV) can be prepared by condensing Compound (XXXII) and Compound (XXXIII) in the presence of copper iodide, a ligand (for example, proline, 1,2-cyclohexanediamine and the like) and a base (for example, potassium carbonate, potassium tert-butoxide and the like) in an inert solvent (for example, dimethyl sulfoxide, N,N-dimethylformamide, toluene and the like). The reaction temperature is usually at room temperature to reflux temperature, and the reaction time is usually 1 hour to 1 week, varying based on the starting materials employed, the reaction temperature and the like.

Process 7-2

Compound (XXXI) can be prepared by condensing Compound (XXXIV) and Carbonyl derivative (XX) in the presence of a reducing agent (for example, decaborane) in a suitable solvent (for example, methanol, tetrahydrofuran and the like). The reaction temperature is usually at room temperature to reflux temperature, and the reaction time is usually 1 hour to 1 week, varying based on the starting materials employed, the reaction temperature and the like.

Also, Compound (XXXI) can be also prepared by condensing Compound (XXXIV) and an alkylating agent (XIX) in the presence of a base (for example, sodium hydride, potassium carbonate) in an inert solvent (for example, N,N-dimethylformamide, tetrahydrofuran and the like). The reaction temperature is usually at −78° C. to reflux temperature, and the reaction time is usually 10 minutes to 24 hours, varying based on the starting materials employed, the reaction temperature and the like.

The above-mentioned schemes are a number of examples of methods for preparing the compound of the present invention or synthetic intermediates thereof, and various modifications of these schemes are available as a person skilled in the art can be easily understood.

In addition, when a protective group is necessary depending on the type of functional group, operations of introduction and deprotection can be also conducted optionally in combination according to conventional method. With regrad to the introduction, the deprotection and the kind of protecting group, for example, a method described in Greene's Protective Groups in Organic Synthesis (4th edition) Wiley-Interscience, edited and written by Peter G. M. Wuts & Theodora W. Greene, 2006, can be illustrated.

Compounds represented by the general formula (I) of the present invention and intermediates used for preparing compounds thereof can be isolated or purified by conventional isolation or purification techniques well known to a person skilled in the art, such as solvent extraction, crystallization, recrystallization, chromatography, preparative high performance liquid chromatography or the like as needed.

Compounds of the present invention prepared in this way exhibit excellent $S1P_1$ receptor antagonistic activities, and are useful as an agent for the treatment or prevention of $S1P_1$ receptor-mediated various diseases. For example, compounds of the present invention are useful as an agent for the treatment or prevention of a disease selected from autoimmune diseases, inflammatory bowel disease, age-related macular degeneration, acute or chronic rejection on allo- or xenogeneic tissue or organ transplantation, graft-versus-host disease and cancer.

As autoimmune diseases, for example, multiple sclerosis, rheumatoid arthritis, systemic lupus erythematosus, Hashimoto's disease, scleroderma, polymyositis, psoriasis, lupus nephritis, severe asthma, atopic dermatitis, contact dermatitis and the like can be illustrated.

As inflammatory bowel diseases, for example, ulcerative colitis, Crohn's disease and the like can be illustrated.

As acute or chronic rejection on allo- or xenogeneic tissue or organ transplantation, for example, rejections of heart transplantation, kidney transplantation, liver transplantation, skin transplantation, bone marrow transplantation and the like can be illustrated.

As cancers, for example, Kaposi's sarcoma, breast cancer, bladder cancer, esophageal cancer, fallopian tube cancer, pancreatic cancer, prostate cancer, cervical cancer, colorectal cancer, gastric cancer, head and neck cancer, Hodgkin's disease, leukemia, malignant lymphoma, osteosarcoma, ovarian cancer, lung cancer, testicular cancer and the like can be illustrated.

Compounds of the present invention can be also optionally used in combination with any other immuno-suppressive drugs used in the the treatment or prevention of autoimmune diseases, inflammatory bowel disease, age-related macular degeneration, acute or chronic rejection on allo- or xenogeneic tissue or organ transplantation, graft-versus-host disease and cancer, inflammatory bowel disease treatment agents, anticancer agents or age-related macular degeneration treatment agents.

As such immuno-suppressive agents, for example, $S1P_1$ receptor agonists such as fingolimod and the like; calcineurin inhibitors such as cyclosporine, tacrolimus and the like; mTOR inhibitors such as rapamycin and the like; folic acid metabolism antagonist such as methotrexate and the like; azathioprine, cyclophosphamide and the like can be illustrated.

As inflammatory bowel disease treatment agents, for example, 5-ASA formulations such as mesalazine, sulfasalazine and the like; steroids such as prednisolone, methylprednisolone, dexamethasone, betamethasone, triamcinolone and the like, and the like can be illustrated.

As anticancer agents, for example, a topoisomerase I inhibitor such as camptothecin, irinotecan and the like; topoisomerase II inhibitors such as etoposide, dexrazoxane and the like; classical alkylating agents such as cyclophosphamide and the like; DNA damage/binding agents such as cisplatin, oxaliplatin and the like; antibiotics such as bleomycin, actinomycin, mitomycin C and the like; anthracyclines such as daunorubicin and the like; antimetabolites such as methotrexate, 5-fluorouracil and the like, and the like can be illustrated.

As age-related macular degeneration treatment agents, for example, VEGF inhibitors such as pegaptanib aflibercept, ranibizumab and the like; steroids such as triamcinolone and the like, and the like can be illustrated.

A pharmaceutical composition comprising a compound represented by the general formula (I) of the present invention or a pharmaceutically acceptable salt thereof as an active ingredient can be administered in various dosage forms depending on their usages. As such dosage forms, for example, powders, granules, fine granules, dry syrups, tablets, capsules, injections, liquids, ointments, suppositories, poultices and the like can be illustrated, which are administered orally or parenterally.

A pharmaceutical composition comprising a compound represented by the general formula (I) of the present invention or a pharmaceutically acceptable salt thereof can be prepared by using a compound represented by the general formula (I) or a pharmeceutically acceptable salt thereof and at least one of a pharmaceutical additive. These pharmaceutical compositions can be formulated by admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents, solubilizing agents and the like, according to a conventional formulation procedure depending upon their dosage forms.

The dosage of a compound represented by the general formula (I) or a pharmaceutically acceptable salt thereof is appropriately determined depending on the age, sex, body weight, degree of disorders and treatment of each patient and the like, which is approximately within the range of from about 1 mg to about 1000 mg per day per adult human, preferably about 5 mg to about 500 mg, and more preferably about 10 mg to about 100 mg, in the case of oral administration, and approximately within the range of from about 0.1 mg to about 100 mg per day per adult human, preferably about 1 mg to about 10 mg, in the case of parenteral administration, the daily dose can be divided into one to several times per day and administered.

A pharmaceutical comprising combination of a compound represented by the general formula (I) of the present invention or a pharmaceutically acceptable salt thereof and other immuno-suppressive drugs, inflammatory bowel disease treatment agents, age-related macular degeneration treatment agents or anticancer agents can be administered as a single pharmaceutical composition comprising together with these active ingredients, or as separately formulated pharmaceutical compositions each of which comprises a single active ingredient. When separately formulated pharmaceutical compositions are used, these compositions can be administered separately or concurrently. Alternatively, when separately formulated pharmaceutical compositions are used, these compositions can be mixed together with an appropriate diluent, at the point of use, and administered simultaneously.

In a pharmaceutical comprising combination of a compound represented by the general formula (I) of the present invention or a pharmaceutically acceptable salt thereof and other immuno-suppressive drugs, inflammatory bowel disease treatment agents, age-related macular degeneration treatment agents or anticancer agents, the combination ratio of medicament can be appropriately determined depending on the age, sex or body weight of the individual patient, the severity of the disease, administration time, dosage form, administration method, combination of medicaments and the like.

The present invention is further illustrated in more detail by way of the following Reference Examples, Examples and Test Examples. However, the present invention is not limited thereto.

EXAMPLES

Reference Example 1-1

1-{3-[(4-Chloro-3-methylphenylamino)methyl]benzyl}azetidine-3-carboxylic acid methyl ester
Step 1
To a mixture of azetidine-3-carboxylic acid methyl ester hydrochloride (400 mg), benzene-1,3-dicarbaldehyde (708 mg), triethylamine (0.37 mL) and tetrahydrofuran (10 mL) was added sodium blacetoxyborohydride (1.12 g), and the mixture was stirred at room temperature for 3 hours. After the mixture was diluted with ethyl acetate, the resulting mixture was washed with saturated sodium hydrogen carbonate aqueous solution and brine successively, and concentrated under reduced pressure. The residue was purified by column chromatography on silica gel (eluent: 20%-100% ethyl acetate/hexane, gradient elution) to give 1-(3-formylbenzyl) azetidine-3-carboxylic acid methyl ester (330 mg).
MS (ESI, m/z): 234M+H)+
Step 2
To a mixture of 1-(3-formylbenzyl)azetidine-3-carboxylic acid methyl ester (330 mg), 4-chloro-3-methylphenylamine (243 mg) and methanol (8 mL) was added decaborane (90 mg), and the mixture was stirred at room temperature for 2 hours. After the mixture was diluted with ethyl acetate, to the resulting mixture was added aminopropyl silica gel powder (3 g). The resulting mixture was filtered and the filtrate was concentrated under reduced pressure. The residue was purified by aminopropyl silica gel column chromatography (eluent: 20%-50% ethyl acetate/hexane, gradient elution) to give the title compound (450 mg). The structural formula was illustrated in Table 1.

TABLE 1

| Reference Example | Structural formula |
| --- | --- |
| 1-1 | 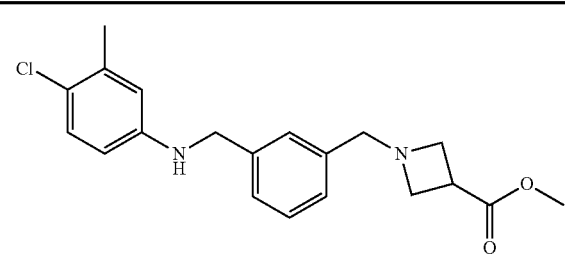 |

The physical data of Reference Example 1-1 was shown below.

Reference Example 1-1

MS (ESI, m/z): 359(M+H)$^+$

Reference Example 2-1

(3-{[(4-Chloro-3-methylphenyl)(ethyl)amino]methyl}phenyl)methanol

Step 1
To a mixture of 3-formylbenzoic acid methyl ester (1.25 g), 4-chloro-3-methylphenylamine (1.29 g), tetrahydrofuran (15 mL) and methanol (15 mL) was added decaborane (232 mg), and the mixture was stirred at room temperature for 2 hours. After the mixture was diluted with ethyl acetate, to the resulting mixture was added aminopropyl silica gel powder (5 g). The resulting mixture was filtered and the filtrate was concentrated under reduced pressure to give 3-[(4-chloro-3-methylphenylamino)methyl]benzoic acid methyl ester (2.13 g).
MS (ESI m/z): 290(M+H)$^+$ Step 2
To a mixture of 3-[(4-chloro-3-methylphenylamino)methyl]benzoic acid methyl ester (415 mg), acetaldehyde (5 mol/L tetrahydrofuran solution, 0.72 mL) and methanol (6 mL) was added decaborane (53 mg), and the mixture was stirred at room temperature for 20 minutes. After the mixture was diluted with ethyl acetate, to the resulting mixture was added aminopropyl silica gel powder (3 g). The resulting mixture was filtered and the filtrate was concentrated under reduced pressure to give 3-{[(4-chloro-3-methylphenyl)(ethyl)amino]methyl}benzoic acid methyl ester (421 mg).
MS (ESI, m/z): 318(M+H)$^+$ Step 3
To a mixture of 3-{[(4-chloro-3-methylphenyl)(ethyl)amino]methyl}benzoic acid methyl ester (421 mg) and tetrahydrofuran (10 mL) was added lithium aluminum hydride (80 mg) under ice-cooling, and the mixture was stirred at the same temperature for 30 minutes. To the mixture was added water in a dropwise manner, and the resulting mixture was diluted with saturated sodium hydrogen carbonate aqueous solution and ethyl acetate. The ethyl acetate layer was washed with brine, and concentrated under reduced pressure to give the title compound (384 mg). The structural formula was illustrated in Table 2.

Reference Example 2-2 to Reference Example 2-10

Reference Example 2-2 to Reference Example 2-10 were synthesized in a similar manner to that described in Reference Example 2-1 using the corresponding phenylamine derivatives instead of 4-chloro-3-methylphenylamine in Step 1, and using the corresponding aldehyde derivatives instead of acetaldehyde in Step 2. These structural formulae were illustrated in Table 2.

Reference Example 2-11

Reference Example 2-11 was synthesized in a similar manner to that described in Reference Example 2-1 using Reference Example 6-9 instead of 3-formylbenzoic acid methyl ester and using 3,5-bis-trifluoromethylphenylamine instead of 4-chloro-3-methylphenylamine in Step 1. The structural formula was illustrated in Table 2.

Reference Example 2-12

Reference Example 2-12 was synthesized in a similar manner to that described in Reference Example 2-1 using Reference Example 6-10 instead of 3-formylbenzoic acid methyl ester and using 4-chloro-3-trifluoromethylphenylamine instead of 4-chloro-3-methylphenylamine in Step 1. The structural formula was illustrated in Table 2.

Reference Example 2-13

(3-{[(4-Chloro-3-methylphenyl)(isopropyl)amino]methyl}phenyl)methanol

Step 1
To a mixture of 4-chloro-3-methylphenylamine (300 mg), acetone (0.19 mL) and methanol (10 mL) was added decaborane (130 mg), and the mixture was stirred at room temperature for 6 hours. After the mixture was diluted with ethyl acetate, to the resulting mixture was added aminopropyl silica gel powder (3 g). The resulting mixture was filtered and the filtrate was concentrated under reduced pressure to give (4-chloro-3-methylphenyl)(isopropyl)amine (390 mg).

Step 2
To a mixture of (4-chloro-3-methylphenyl)(isopropyl)amine (390 mg), 3-formylbenzoic acid methyl ester (452 mg) and methanol (10 mL) was added decaborane (130 mg), and the mixture was stirred at room temperature for 18 hours. After the mixture was diluted with ethyl acetate, to the resulting mixture was added aminopropyl silica gel powder (3 g). The resulting mixture was filtered and the filtrate was concentrated under reduced pressure to give 3-{[(4-chloro-3-methylphenyl)(isopropyl)amino]methyl}benzoic acid methyl ester (379 mg).
MS (ESI, m/z): 332(M+H)$^+$ Step 3
To a mixture of 3-{[(4-chloro-3-methylphenyl)(isopropyl)amino]methyl}-benzoic acid methyl ester (379 mg) and tetrahydrofuran (10 mL) was added lithium aluminium hydride (69 mg) under ice-cooling, and the mixture was stirred at the same temperature for 30 minutes. To the mixture was added water in a dropwise manner, and the resulting mixture was diluted with saturated sodium hydrogen carbonate aqueous solution and ethyl acetate. The ethyl acetate layer was washed with brine, and concentrated under reduced pressure to give the title compound (345 mg). The structural formula was illustrated in Table 2.

Reference Example 2-14

Reference Example 2-14 was synthesized in a similar manner to that described in Reference Example 2-13 using cyclobutanone instead of acetone in Step 1. The structural formula was illustrated in Table 2.

Reference Example 2-15

(3-{[(4-Chloro-3-methylphenyl)-2,2,2-trifluoroethyl)amino]methyl}phenyl)methanol Step 1
To a mixture of 4-chloro-3-methylphenylamine (350 mg), potassium carbonate (1.09 g) and N,N-dimethylformamide (10 mL) was added trifluoromethanesulfonic acid 2,2,2- trifluoroethyl ester (0.57 mL), and the mixture was stirred at an external temperature of 80° C. for 20 hours. The mixture was cooled to room temperature. After the mixture was diluted with ethyl acetate, and the resulting mixture was washed with water, saturated sodium hydrogen carbonate aqueous solution and brine successively, and concentrated under reduced pressure. The residue was purified by column chromatography on silica gel (eluent: 0%-10% ethyl acetate:hexane, gradient elution) to give (4-chloro-3-methylphenyl)-(2,2,2-trifluoroethyl)amine (209 mg).

$^1$H-NMR (CDCl$_3$) δ ppm: 2.31 (3H, s), 3.65-3.90 (3H, m), 6.46 (1H, dd, J=8.5, 2.8 Hz), 6.55 (1H, d, J=2.8 Hz), 7.15 (1H, d, J=8.5 Hz).

Step 2

To a mixture of (4-chloro-3-methylphenyl)-(2,2,2-trifluoroethyl)amine (209 mg), 3-formylbenzoic acid methyl ester (184 mg) and methanol (4 mL) was added decaborane (60 mg), and the mixture was stirred at room temperature for 20 hours. After the mixture was diluted with ethyl acetate, to the resulting mixture was added aminopropyl silica gel powder (3 g). The resulting mixture was filtered and the filtrate was concentrated under reduced pressure to give 3-{[(4-chloro-3-methylphenyl)-(2,2,2-trifluoroethyl)amino]methyl}benzoic acid methyl ester (350 mg)

Step 3

To a mixture of 3-{[(4-chloro-3-methylphenyl)-(2,2,2-trifluoroethyl)amino]-methyl}benzoic acid methyl ester (350 mg) and tetrahydrofuran (10 mL) was added lithium aluminium hydride (71 mg) under ice-cooling, and the mixture was stirred at the same temperature for 30 minutes. To the mixture was added water in a dropwise manner, and the resulting mixture was diluted with saturated sodium hydrogen carbonate aqueous solution and ethyl acetate. The ethyl acetate layer was washed with brine, and concentrated under reduced pressure to give the title compound (340 mg). The structural formula was illustrated in Table 2.

Reference Example 2-16

{5-[(4-Chloro-3-methylphenyl)(ethyl)amino]-5,6,7,8-tetrahydronaphthalen-1-yl}-methanol Step 1

To a mixture of 5-hydroxy-3,4-dihydro-2H-naphthalen-1-one (693 mg), 4-chloro-3-methylphenylamine (550 mg) and methanol (20 mL) was added decaborane (236 mg), and the mixture was stirred at room temperature for 8 hours. After the mixture was diluted with ethyl acetate, to the resulting mixture was added aminopropyl silica gel powder (5 g). The resulting mixture was filtered and the filtrate was concentrated under reduced pressure to give 5-(4-chloro-3-methylphenylamino)-5,6,7,8-tetrahydronaphthalen-1-ol (1.1 g).

Step 2

To a mixture of 5-(4-chloro-3-methylphenylamino)-5,6,7,8-tetrahydronaphthalen-1-ol (1.1 g), acetaldehyde (5 mol/L tetrahydrofuran solution, 2.0 mL) and methanol (20 mL) was added decaborane (236 mg), and the mixture was stirred at room temperature for 30 minutes. After the mixture was diluted with ethyl acetate, to the resulting mixture was added aminopropyl silica gel powder (5 g). The resulting mixture was filtered and the filtrate was concentrated under reduced pressure. The residue was purified by column chromatography on silica gel (eluent: 10%-25% ethyl acetate/hexane, gradient elution) to give 5-[(4-chloro-3-methylphenyl)(ethyl)-amino]-5,6,7,8-tetrahydronaphthalen-1-ol (840 mg).

$^1$H-NMR (CDCl$_3$) δ ppm: 1.12 (3H, t, J=7.0 Hz), 1.70-2.20 (4H, m), 2.32 (3H, s), 2.50-2.65 (1H, m), 2.75-2.85 (1H, m), 3.00-3.20 (2H, m), 4.68 (1H, s), 4.85-5.00 (1H, m), 6.56 (1H, dd, J=8.8, 3.0 Hz), 6.60-6.70 (2H, m), 6.80-6.85 (1H, m), 6.95-7.05 (1H, m), 7.13 (1H, d, J=8.8 Hz)

Step 3

To a mixture of 5-[(4-chloro-3-methylphenyl)(ethyl)amino]-5,6,7,8-tetrahydronaphthalen-1-ol (830 mg), pyridine (0.64 mL) and dichloromethane (15 mL) was added trifluoromethanesulfonic anhydride (0.66 mL) under ice-cooling, and the mixture was stirred at the same temperature for 20 minutes. After the mixture was diluted with ethyl acetate, the resulting mixture was washed with water, saturated sodium hydrogen carbonate aqueous solution and brine successively, and concentrated under reduced pressure to give trifluoromethanesulfonic acid 5-[(4-chloro-3-methylphenyl)(ethyl)amino]-5,6,7,8-tetrahydronaphthalen-1-yl ester (1.2 g).

MS (ESI, m/z): 448(M+H)$^+$

Step 4

To a mixture of trifluoromethanesulfonic acid 5-[(4-chloro-3-methylphenyl)(ethyl)amino]-5,6,7,8-tetrahydronaphthalen-1-yl ester (1.2 g), 1-propanol (10 mL), triethylamine (1.47 mL), toluene (10 mL) and N-methylpyrrolidone (5 mL) were added [1,1'-bis(diphenylphosphino)ferrocene]palladium dichloride dichloromethane complex (215 mg) and 1,1'-bis(diphenylphosphino)ferrocene (146 mg), and the mixture was stirred under a carbon monoxide atmosphere at an external temperature of 105° C. for 3 hours. The mixture was cooled to room temperature. After the mixture was diluted with ethyl acetate, the resulting mixture was washed with water, saturated sodium hydrogen carbonate aqueous solution and brine successively, and concentrated under reduced pressure to give 5-[(4-chloro-3-methylphenyl)(ethyl)amino]-5,6,7,8-tetrahydronaphthalene-1-carboxylic acid propyl ester (1.0 g).

Step 5

To a mixture of 5-[(4-chloro-3-methylphenyl)(ethyl)amino]-5,6,7,8-tetrahydronaphthalene-1-carboxylic acid propyl ester (1.0 g) and tetrahydrofuran (20 mL) was added lithium aluminium hydride (150 mg) under ice-cooling, and the mixture was stirred at the same temperature for 30 minutes. To the mixture was added water in a dropwise manner, and the resulting mixture was diluted with saturated sodium hydrogen carbonate aqueous solution and ethyl acetate. The ethyl acetate layer was washed with brine, and concentrated under reduced pressure. The residue was purified by aminopropyl silica gel column chromatography (eluent: 10%-50% ethyl acetate/hexane, gradient elution) to give the title compound (723 mg). The structural formula was illustrated in Table 2.

Reference Example 2-17

Reference Example 2-17 was synthesized in a similar manner to that described in Reference Example 2-16 using 2-formyl-6-hydroxybenzonitrile instead of 5-hydroxy-3,4-dihydro-2H-naphthalen-1-one in Step 1. The structural formula was illustrated in Table 2.

TABLE 2
| Reference Example | Structural formula |
|---|---|
| 2-1 | 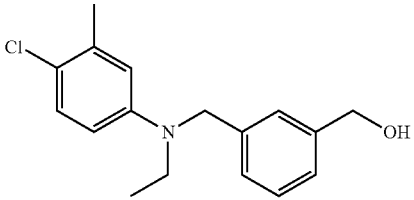 [SMILES: CCN(Cc1cccc(CO)c1)c1ccc(Cl)c(C)c1] |
| 2-2 | 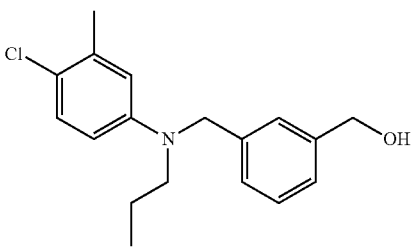 [SMILES: CCCN(Cc1cccc(CO)c1)c1ccc(Cl)c(C)c1] |
| 2-3 | 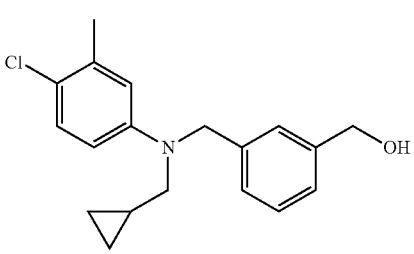 [SMILES: Cc1cc(N(Cc2cccc(CO)c2)CC2CC2)ccc1Cl] |
| 2-4 | 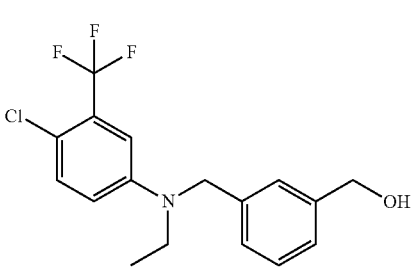 [SMILES: CCN(Cc1cccc(CO)c1)c1ccc(Cl)c(C(F)(F)F)c1] |
| 2-5 | 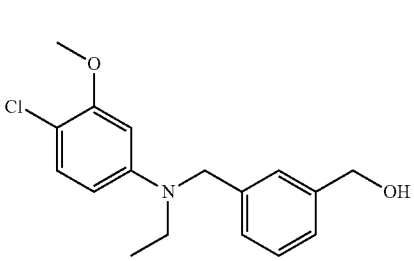 [SMILES: CCN(Cc1cccc(CO)c1)c1ccc(Cl)c(OC)c1] |
| 2-6 | 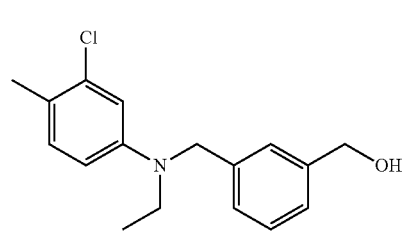 [SMILES: CCN(Cc1cccc(CO)c1)c1ccc(C)c(Cl)c1] |
| 2-7 | 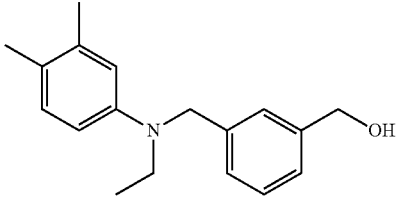 [SMILES: CCN(Cc1cccc(CO)c1)c1ccc(C)c(C)c1] |
| 2-8 | 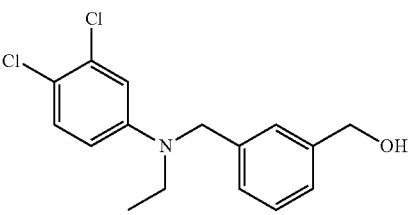 [SMILES: CCN(Cc1cccc(CO)c1)c1ccc(Cl)c(Cl)c1] |
| 2-9 | 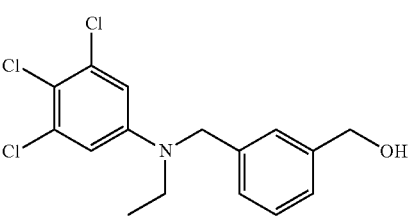 [SMILES: CCN(Cc1cccc(CO)c1)c1cc(Cl)c(Cl)c(Cl)c1] |
| 2-10 | 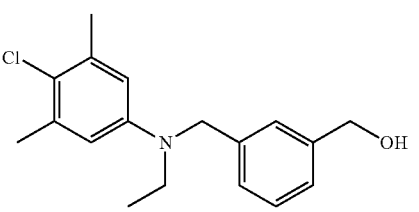 [SMILES: CCN(Cc1cccc(CO)c1)c1cc(C)c(Cl)c(C)c1] |
| 2-11 | 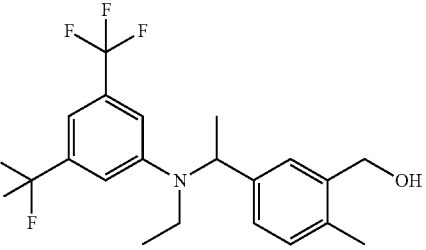 |
| 2-12 | 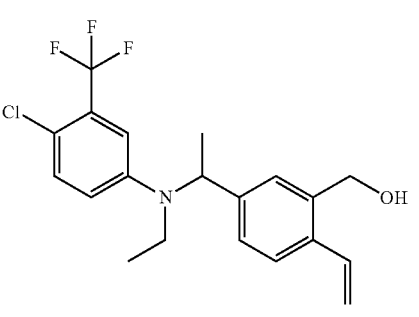 [SMILES: C=Cc1ccc(C(C)N(CC)c2ccc(Cl)c(C(F)(F)F)c2)cc1CO] |

TABLE 2-continued

| Reference Example | Structural formula |
|---|---|
| 2-13 | 4-Cl-3-methylphenyl-N(iPr)-CH2-(3-hydroxymethyl)phenyl |
| 2-14 | 4-Cl-3-methylphenyl-N(cyclobutyl)-CH2-(3-hydroxymethyl)phenyl |
| 2-15 | 4-Cl-3-methylphenyl-N(CH2CF3)-CH2-(3-hydroxymethyl)phenyl |
| 2-16 | 4-Cl-3-methylphenyl-N(Et)-(tetrahydronaphthalenyl with CH2OH) |
| 2-17 | 4-Cl-3-methylphenyl-N(Et)-CH2-(2-CN-6-hydroxymethyl)phenyl |

The physical properties of Reference Example 2-1 to Reference Example 2-6, Reference Example 2-13 to Reference Example 2-15 and Reference Example 2-17 were shown below.

Reference Example 2-1

$^1$H-NMR (CDCl$_3$) δ ppm: 1.18 (3H, t, J=7.0 Hz), 1.67 (1H, t, J=5.8 Hz), 2.28 (3H, s), 3.43 (2H, q, J=7.01 Hz), 4.47 (2H, s), 4.67 (2H, d, J=5.8 Hz), 6.44 (1H, dd, J=8.8, 3.0 Hz), 6.55 (1H, d, J=3.0 Hz), 7.05-7.35 (5H, m)

Reference Example 2-2

MS (ESI, m/z): 304(M+H)$^+$

Reference Example 2-3

MS (ESI, m/z): 316(M+H)$^+$

Reference Example 2-4

$^1$H-NMR (CDCl$_3$) δ ppm: 1.22 (3H, t, J=7.0 Hz), 1.65 (1H, t, J=5.8 Hz), 3.50 (2H, q, J=7.0 Hz), 4.52 (2H, s), 4.68 (2H, d, J=5.8 Hz), 6.67 (1H, dd, J=8.8, 3.0 Hz), 6.96 (1H, d, J=3.0 Hz), 7.10-7.35 (5H, m)

Reference Example 2-5

$^1$H-NMR (CDCl$_3$) δ ppm: 1.22 (3H, t, J=7.0 Hz), 1.63 (1H, t J=5.8 Hz), 3.48 (2H, q, J=7.0 Hz), 3.77 (3H, s), 4.50 (2H, s), 4.68 (2H, d, J=5.8 Hz), 6.20-6.25 (2H, m), 7.05-7.35 (5H, m)

Reference Example 2-6

$^1$H-NMR (CDCl$_3$) δ ppm: 1.18 (3H, t, J=7.0 Hz), 2.24 (3H, s), 3.43 (2H, q, J=7.0 Hz), 4.47 (2H, s), 4.67 (2H, d, J=6.0 Hz), 6.48 (1H, dd, J=8.5, 2.8 Hz), 6.70 (1H, d, J=2.8 Hz), 6.99 (1H, d, J=8.5 Hz), 7.10-7.35 (4H, m)

Reference Example 2-13

MS (ESI, m/z): 304(M+H)$^+$

Reference Example 2-14

MS (ESI, m/z): 316(M+H)$^+$

Reference Example 2-15

MS (ESI, m/z): 344(M+H)$^+$

Reference Example 2-17

MS (ESI, m/z): 315(M+H)$^+$

Reference Example 3-1

(4-Chloro-3-methylphenyl)(ethyl)(3-iodo-4-methylbenzyl)amine

Step 1
To a mixture of 3-iodo-4-methylbenzaldehyde (600 mg), 4-chloro-3-methylphenylamine (414 mg), tetrahydrofuran (2 mL) and methanol (6 mL) was added decaborane (90 mg), and the mixture was stirred at room temperature for 1 hour. After the mixture was diluted with ethyl acetate, to the resulting mixture was added aminopropyl silica gel powder (3 g). The resulting mixture was filtered and the filtrate was concentrated under reduced pressure to give (4-chloro-3-methylphenyl)-(3-iodo-4-methylbenzyl)amine (900 mg).

Step 2
To a mixture of (4-chloro-3-methylphenyl)-(3-iodo-4-methylbenzyl)amine (900 mg), acetaldehyde (5 mol/L tetrahydrofuran solution, 2.0 mL), tetrahydrofuran (2 mL) and methanol (6 mL) was added decaborane (90 mg), and the mixture was stirred at room temperature for 1 hour. After the mixture was diluted with ethyl acetate, to the resulting mixture was added aminopropyl silica gel powder (4 g). The resulting mixture was filtered and the filtrate was concentrated under reduced pressure. The residue was purified by aminopropyl silica gel column chromatography (eluent:

hexane) to give the title compound (747 mg). The structural formula was illustrated in Table 3.

Reference Example 3-2 to Reference Example 3-26 and Reference Example 3-28 to Reference Example 3-44

Reference Example 3-2 to Reference Example 3-26 and Reference Example 3-28 to Reference Example 3-44 were synthesized in a similar manner to that described in Reference Example 3-1 using the corresponding commercially available benzaldehyde derivatives, commercially available phenylketone derivatives or Reference Example 6-1 to Reference Example 6-7 instead of 3-iodo-4-methylbenzaldehyde, and the corresponding phenylamine derivatives instead of 4-chloro-3-methyl-phenylamine in Step 1, and using the corresponding aldehyde derivatives instead of acetaldehyde in Step 2. The structural formula was illustrated in Table 3.

Reference Example 3-45

2-(3-Bromo-4-methylphenyl)-2-[(4-chloro-3-trifluoromethylphenyl)(ethyl)amino]-ethanol Step 1

To a mixture of acetic acid 2-(3-bromo-4-methylphenyl)-2-oxoethyl ester (1.11 g) (Reference Example 6-8), 4-chloro-3-trifluoromethylphenylamine (0.92 g) and methanol (20 mL) was added decaborane (250 mg), and the mixture was stirred at room temperature for 90 hours. To the mixture were added water (5 mL) and potassium carbonate (2.9 g), and the resulting mixture was stirred at an external temperature of 60° C. for 2 hours. The mixture was cooled to room temperature. The mixture was diluted with water and ethyl acetate. The ethyl acetate layer was washed with brine, and concentrated under reduced pressure to give 2-(3-bromo-4-methylphenyl)-2-(4-chloro-3-trifluoromethylphenylamino)ethanol (1.68 g).

Step 2

To a mixture of 2-(3-bromo-4-methylphenyl)-2-(4-chloro-3-trifluoromethyl-phenylamino)ethanol (1.68 g), acetaldehyde (5 mol/L tetrahydrofuran solution, 4.0 mL) and methanol (20 mL) was added decaborane (150 mg), and the mixture was stirred at room temperature for 6 hours. After the mixture was diluted with ethyl acetate, to the resulting mixture was added aminopropyl silica gel powder (4 g). The resulting mixture was filtered and the filtrate was concentrated under reduced pressure. The residue was purified by silica gel column chromatography (eluent: 10%-40% ethyl acetate/hexane gradient elution) to give the title compound (1.55 g). The structural formula was illustrated in Table 3.

Reference Example 3-27

Reference Example 3-27 was synthesized in a similar manner to that described in Reference Example 3-45 using acetic acid 2-(3-bromophenyl)-2-oxoethyl ester instead of acetic acid 2-(3-bromo-4-methylphenyl)-2-oxoethyl ester (Reference Example 6-8), and using 4-chloro-3-methylphenylamine instead of 4-chloro-3-trifluoromethylphenylamine in Step 1. The structural formula was illustrated in Table 3.

Reference Example 3-46

2-{[1-(3-Bromo-4-methylphenyl)ethyl]-(4-chloro-3-trifluoromethylphenyl)amino)}-ethanol Step 1

To a mixture of 1-(3-bromo-4-methylphenyl)ethanone (1.11 g), 4-chloro-3-trifluoromethylphenylamine (1.02 g) and methanol (10 mL) was added decaborane (279 mg), and the mixture was stirred at room temperature for 12 hours. After the mixture was diluted with ethyl acetate, to the resulting mixture was added aminopropyl silica gel powder (5 g). The resulting mixture was filtered and the filtrate was concentrated under reduced pressure to give [1-(3-bromo-4-methylphenyl)ethyl]-(4-chloro-3-trifluoromethylphenyl)amine (2.11 g).

Step 2

To a mixture of [1-(3-bromo-4-methylphenyl)ethyl]-(4-chloro-3-trifluoromethylphenyl)amine (531 mg), (tert-butyldimethylsilanyloxy)acetaldehyde (589 mg), tetrahydrofuran (2 mL) and methanol (3 mL) was added decaborane (104 mg), and the mixture was stirred at room temperature for 12 hours. After the mixture was diluted with ethyl acetate, to the resulting mixture was added aminopropyl silica gel powder (5 g). The resulting mixture was filtered and the filtrate was concentrated under reduced pressure. The residue was purified by aminopropyl silica gel column chromatography (eluent: 0%-60% ethyl acetate/hexane, gradient elution) to give the title compound (580 mg). The structural formula was illustrated in Table 3.

Reference Example 3-47 to Reference Example 3-50

Reference Example 3-47 to Reference Example 3-50 were synthesized in a similar manner to that described in Reference Example 3-46 using the corresponding commercially available phenylketone, Reference Example 6-1 or Reference Example 6-3 instead of 1-(3-bromo-4-methylphenyl)ethanone, and using the corresponding phenylamine derivatives instead of 4-chloro-3-trifluoromethylphenylamine in Step 1. The structural formula was illustrated in Table 3.

Reference Example 3-51

[1-(3-Bromo-4-methylphenyl)ethyl]-(4-chloro-3-trifluoromethylphenyl)-(2-methoxyethyl)amine To a mixture of 2-{[1-(3-bromo-4-methylphenyl)ethyl]-(4-chloro-3-trifluoromethylphenyl)amino}ethanol (Reference Example 3-46 (294 mg), iodomethane (0.13 mL) and N,N-dimethylformamide (4 mL) was added sodium hydride (50% in oil, 39 mg) under ice-cooling, and the mixture was stirred at room temperature for 1 hour. After the mixture was diluted with ethyl acetate, the resulting mixture was washed with water and brine successively, and concentrated under reduced pressure. The residue was purified by aminopropyl silica gel column chromatography (eluent: 0%-15% ethyl acetate/hexane, gradient elution) to give the title compound (280 mg). The structural formula was illustrated in Table 3.

Reference Example 3-52 and Reference Example 3-53

Reference Example 3-52 and Reference Example 3-53 were synthesized in a similar manner to that described in Reference Example 3-51 using Reference Example 3-49 and Reference Example 3-50 instead of Reference Example 3-46. The structural formula was illustrated in Table 3.

Reference Example 3-54

(4-Chloro-3-methylphenyl)-(3-iodo-4-methylbenzyl)(isopropyl)amine

To a mixture of (4-chloro-3-methylphenyl)(isopropyl)amine (520 mg) obtained in Step 1 of Reference Example 2-13, 3-iodo-4-methylbenzaldehyde (700 mg), tetrahydrofuran (2 mL) and methanol (8 mL) was added decaborane (173 mg), and the mixture was stirred at room temperature for 16 hours. After the mixture was diluted with ethyl acetate, to the resulting mixture was added aminopropyl silica gel powder (3 g). The resulting mixture was filtered and the filtrate was concentrated under reduced pressure. The residue was purified by column chromatography on silica gel (eluent: 0%-5% ethyl acetate/hexane, gradient elution) to give the title compound (368 mg). The structural formula was illustrated in Table 3.

TABLE 3-continued

| Reference Example | Structural formula |
|---|---|
| 3-12 | |
| 3-13 | |
| 3-14 | |
| 3-15 | |
| 3-16 | |
| 3-17 | |
| 3-18 | |
| 3-19 | |
| 3-20 | |
| 3-21 | |
| 3-22 | |
| 3-23 | |

TABLE 3-continued

| Reference Example | Structural formula |
|---|---|
| 3-24 | (4-chloro-3-methylphenyl)(N-ethyl)(1-(3-bromo-5-chlorophenyl)ethyl)amine |
| 3-25 | (4-chloro-3-methylphenyl)(N-ethyl)(1-(3-bromo-4-methoxyphenyl)ethyl)amine |
| 3-26 | (4-chloro-3-methylphenyl)(N-ethyl)(1-(3-bromo-4-fluorophenyl)ethyl)amine |
| 3-27 | (4-chloro-3-methylphenyl)(N-ethyl)(2-hydroxy-1-(3-bromophenyl)ethyl)amine |
| 3-28 | (4-chloro-3-methylphenyl)(N-ethyl)(1-(3-bromo-4-chlorophenyl)ethyl)amine |
| 3-29 | (4-chloro-3-trifluoromethylphenyl)(N-methyl)(1-(3-bromo-4-chlorophenyl)ethyl)amine |

TABLE 3-continued

| Reference Example | Structural formula |
|---|---|
| 3-30 | (4-chloro-3-trifluoromethylphenyl)(N-ethyl)(1-(3-bromo-4-chlorophenyl)ethyl)amine |
| 3-31 | (4-chloro-3-trifluoromethylphenyl)(N-methyl)(4-bromo-5-methylindan-1-yl)amine |
| 3-32 | (4-chloro-3-trifluoromethylphenyl)(N-ethyl)(4-bromo-5-methylindan-1-yl)amine |
| 3-33 | (4-chloro-3-methylphenyl)(N-ethyl)(3-bromo-2,4-dimethylbenzyl)amine |
| 3-34 | (4-chloro-3-trifluoromethylphenyl)(N-ethyl)(1-(3-bromo-4-trifluoromethylphenyl)ethyl)amine |

TABLE 3-continued

| Reference Example | Structural formula |
|---|---|
| 3-35 | 4-chloro-3-(trifluoromethyl)phenyl-N-methyl-N-[1-(3-bromo-4-(trifluoromethyl)phenyl)ethyl]amine |
| 3-36 | 4-chloro-3-methylphenyl-N-ethyl-N-[1-(3-bromo-4-(trifluoromethyl)phenyl)ethyl]amine |
| 3-37 | 4-cyano-3-(trifluoromethyl)phenyl-N-methyl-N-[1-(3-bromo-4-methylphenyl)ethyl]amine |
| 3-38 | 4-chloro-3-(trifluoromethyl)phenyl-N-ethyl-N-[1-(3-iodo-4-methylphenyl)propyl]amine |
| 3-39 | 4-chloro-3-methylphenyl-N-ethyl-N-[1-(3-iodo-4-methylphenyl)propyl]amine |
| 3-40 | 4-chlorophenyl-N-ethyl-N-[1-(3-bromo-4-methylphenyl)ethyl]amine |
| 3-41 | phenyl-N-ethyl-N-[1-(3-bromo-4-methylphenyl)ethyl]amine |
| 3-42 | 3-chlorophenyl-N-ethyl-N-[1-(3-bromo-4-methylphenyl)ethyl]amine |
| 3-43 | 3-methoxyphenyl-N-ethyl-N-[1-(3-bromo-4-methylphenyl)ethyl]amine |
| 3-44 | 4-methoxyphenyl-N-ethyl-N-[1-(3-bromo-4-methylphenyl)ethyl]amine |
| 3-45 | 4-chloro-3-(trifluoromethyl)phenyl-N-ethyl-N-[2-hydroxy-1-(3-bromo-4-methylphenyl)ethyl]amine |
| 3-46 | 4-chloro-3-(trifluoromethyl)phenyl-N-(2-hydroxyethyl)-N-[1-(3-bromo-4-methylphenyl)ethyl]amine |

TABLE 3-continued

| Reference Example | Structural formula |
|---|---|
| 3-47 | [4-chloro-3-methylphenyl-N-(2-hydroxyethyl)-N-(4-bromo-5-fluoro-indan-1-yl)amine] |
| 3-48 | [4-chloro-3-methylphenyl-N-(2-hydroxyethyl)-N-(4-bromo-indan-1-yl)amine] |
| 3-49 | [4-chloro-3-trifluoromethylphenyl-N-(2-hydroxyethyl)-N-(4-bromo-5-methyl-indan-1-yl)amine] |
| 3-50 | [4-chloro-3-methylphenyl-N-(2-hydroxyethyl)-N-[1-(3-bromo-4-methylphenyl)ethyl]amine] |
| 3-51 | [4-chloro-3-trifluoromethylphenyl-N-(2-methoxyethyl)-N-[1-(3-bromo-4-methylphenyl)ethyl]amine] |
| 3-52 | [4-chloro-3-trifluoromethylphenyl-N-(2-methoxyethyl)-N-(4-bromo-5-methyl-indan-1-yl)amine] |
| 3-53 | [4-chloro-3-methylphenyl-N-(2-methoxyethyl)-N-[1-(3-bromo-4-methylphenyl)ethyl]amine] |
| 3-54 | [4-chloro-3-methylphenyl-N-isopropyl-N-(3-iodo-4-methylbenzyl)amine] |

The physical properties of Reference Example 3-1 to Reference Example 3-26, Reference Example 3-28 to Reference Example 3-30, Reference Example 3-37, Reference Example 3-46 to Reference Example 3-47, Reference Example 3-50 and Reference Example 3-53 to Reference Example 3-54 were shown below.

Reference Example 3-1

MS (ESI, m/z): 400(M+H)$^+$

Reference Example 3-2

MS (ESI, m/z): 386(M+H)$^+$

Reference Example 3-3

MS (ESI, m/z): 400(M+H)$^+$

Reference Example 3-4

$^1$H-NMR (CDCl$_3$) δ ppm: 0.82 (3H, t, J=6.8 Hz) 1.47 (3H, d, J=6.8 Hz), 2.30-2.40 (6H, m), 2.95-3.20 (2H, m), 4.95-5.10 (1H, m), 6.54 (1H, dd, J=8.8, 3.0 Hz), 6.62 (1H, d, J=3.0 Hz), 6.90 (1H, t, J=7.5 Hz), 7.17 (1H, d, J=8.8 Hz), 7.35 (1H, d, J=7.5 Hz), 7.80 (1H, d, J=7.5 Hz)

Reference Example 3-5

$^1$H-NMR (CDCl$_3$) δ ppm: 1.05 (3H, t, J=7.01 Hz), 1.51 (3H, d, J=7.0 Hz), 2.31 (3H, s), 2.37 (3H, s), 3.05-3.20 (2H, m), 4.85-4.95 (1H, m), 6.55 (1H, dd, J=8.8, 3.0 Hz), 6.66 (1H, d, J=3.0 Hz), 7.05-7.20 (3H, m), 7.40-7.50 (1H, m)

Reference Example 3-6

¹H-NMR (CDCl₃) δ ppm: 0.90-1.05 (6H, m), 1.85-2.10 (2H, m), 2.32 (3H, s), 2.95-3.20 (2H, m), 4.60-4.75 (1H, m), 6.59 (1H, dd, J=8.8, 3.0 Hz), 6.68 (1H, d, J=3.0 Hz), 7.10-7.20 (3H, m), 7.30-7.45 (2H, m)

Reference Example 3-7

¹H-NMR (CDCl₃) δ ppm: 1.49 (3H, d, J=6.8 Hz), 2.33 (3H, s), 2.38 (3H, s), 2.63 (3H, s), 4.90-5.05 (1H, m) 6.59 (1H, dd, J=8.8, 3.0 Hz), 6.67 (1H, d, J=3.0 Hz), 7.05-7.25 (3H, m), 7.40-7.50 (1H, m)

Reference Example 3-8

¹H-NMR (CDCl₃) δ ppm: 0.81 (3H, t, J=7.3 Hz), 1.35-1.55 (5H, m), 2.31 (3H, s), 2.37 (3H, s), 2.90-3.05 (2H, m), 4.80-4.95 (1H, m), 6.53 (1H, dd, J=8.8, 3.0 Hz), 6.63 (1H, d, J=3.01 Hz), 7.05-7.20 (3H, m), 7.40-7.50 (1H, m)

Reference Example 3-9

¹H-NMR (CDCl₃) δ ppm: 1.08 (3H, t, J=7.0 Hz), 2.00-2.20 (1H, m), 2.33 (3H, s), 2.40-2.55 (1H, m), 2.75-2.95 (1H, m), 3.00-3.20 (3H, m), 5.40 (1H, t, J=8.0 Hz), 6.59 (1H, dd, J=8.8, 3.0 Hz), 6.70 (1H, d, J=3.0 Hz), 6.94 (1H, t, J=8.3 Hz), 7.00-7.10 (1H, m), 7.15 (1H, d, J=8.8 Hz)

Reference Example 3-10

¹H-NMR (CDCl₃) δ ppm: 1.11 (3H, t, j=7.0 Hz), 2.00-2.20 (1H, m), 2.33 (3H, s), 2.35-2.50 (1H, m), 2.65-3.25 (4H, m), 5.37 (1H, t, J=8.3 Hz), 6.58 (1H, dd, J=8.8, 3.0 Hz), 6.69 (1H, d, J=3.0 Hz), 6.75-6.90 (1H, m), 7.10-7.20 (2H, m)

Reference Example 3-11

¹H-NMR (CDCl₃) δ ppm: 1.90-2.15 (1H, m), 2.30-2.50 (4H, m), 2.61 (3H, s), 2.75-3.15 (2H, m), 5.52 (1H, t, J=8.0 Hz), 6.67 (1H, dd, J=8.8, 3.0 Hz), 6.75 (1H, d, J=3.0 Hz), 7.00-7.15 (2H, m), 7.19 (1H, d, J=8.8 Hz), 7.35-7.45 (1H, m)

Reference Example 3-12

¹H-NMR (CDCl₃) δ ppm: 1.09 (3H, t, J=7.0 Hz), 2.00-2.15 (1H, m), 2.32 (3H, s), 2.35-2.50 (1H, m), 2.80-2.90 (1H, m), 3.00-3.20 (3H, m), 5.42 (1H, t, J=8.1 Hz), 6.60 (1H, dd, J=8.8, 3.0 Hz), 6.70 (1H, d, J=3.0 Hz), 7.00-7.20 (3H, m), 7.35-7.45 (1H, m)

Reference Example 3-13

¹H-NMR (CDCl₃) δ ppm: 1.08 (3H, t, J=7.0 Hz), 2.00-2.10 (1H, m), 2.33 (3H, s), 2.35-2.50 (1H, m), 2.80-2.90 (1H, m), 3.00-3.20 (3H, m), 3.90 (3H, s), 5.39 (1H, t, J=7.8 Hz), 6.60 (1H, dd, J=8.8, 3.0 Hz), 6.70 (1H, d, J=3.0 Hz), 6.74 (1H, d, J=8.3 Hz), 7.05 (1H, d, J=8.3 Hz), 7.15 (1H, d, J=8.8 Hz)

Reference Example 3-14

¹H-NMR (CDCl₃) δ ppm: 0.81 (3H, t, J=7.3 Hz), 1.45-1.65 (2H, m), 2.00-2.15 (1H, m), 2.32 (3H, s), 2.35-2.45 (1H, m), 2.80-3.10 (4H, m), 539 (1H, t, J=8.3 Hz), 6.57 (1H, dd, J=8.8, 3.0 Hz), 6.68 (1H, d, J=3.0 Hz), 7.00-7.20 (3H, m), 7.39 (1H, d, J=7.7 Hz)

Reference Example 3-15

¹H-NMR (CDCl₃) δ ppm: 1.08 (3H, t, J=7.0 Hz), 1.95-2.15 (1H, m), 2.32 (3H, s), 2.35-2.50 (4H, m), 2.75-3.25 (4H, m), 5.41 (1H, t, J=8.0 Hz), 6.60 (1H, dd, J=8.8, 3.0 Hz), 6.70 (1H, d, J=3.0 Hz), 7.00 (1H, d, J=7.8 Hz), 7.06 (1H, d, J=7.8 Hz), 7.15 (1H, d, J=8.8 Hz)

Reference Example 3-16

¹H-NMR (CDCl₃) δ ppm: 1.90-2.10 (1H, m), 2.29 (3H, s), 2.30-2.45 (4H, m), 2.61 (3H, s), 2.70-3.10 (2H, m), 5.47 (1H, t, J=8.0 Hz), 6.67 (1H, dd, J=8.8, 3.0 Hz), 6.75 (1H, d, J=3.0 Hz), 6.90 (1H, s), 7.16 (1H, d, J=8.8 Hz), 7.24 (1H, s)

Reference Example 3-17

¹H-NMR (CDCl₃) δ ppm: 1.09 (3H, t, J=7.0 Hz), 1.95-2.15 (1H, m), 2.28 (3H, s), 2.30-2.50 (4H, m), 2.70-3.25 (4H, m), 5.37 (1H, t, J=8.0 Hz), 6.59 (1H, dd, J=8.8, 3.0 Hz), 6.70 (1H, d, J=3.0 Hz), 6.90 (1H, s), 7.15 (1H, d, J=8.8 Hz), 7.23 (1H, s)

Reference Example 3-18

¹H-NMR (CDCl₃) δ ppm: 1.95-2.10 (1H, m), 2.40-2.50 (1H, m), 2.67 (3H, s), 2.85-2.95 (1H, m), 3.00-3.15 (1H, m), 5.53 (1H, t, J=8.0 Hz), 6.93 (1H, dd, J=8.8, 3.0 Hz), 7.05-7.20 (3H, m), 7.32 (1H, d, J=8.8 Hz), 7.40-7.50 (1H, m)

Reference Example 3-19

¹H-NMR (CDCl₃) δ ppm: 1.11 (3H, t, J=7.0 Hz), 2.00-2.15 (1H, m), 2.40-2.55 (1H, m), 2.80-2.95 (1H, m), 3.00-3.30 (3H, m), 5.43 (1H, t, J=8.1 Hz), 6.83 (1H, dd, J=8.8, 3.0 Hz), 7.00-7.15 (3H, m), 7.28 (1H, d, J=8.8 Hz), 7.35-7.45 (1H, m)

Reference Example 3-20

¹H-NMR (CDCl₃) δ ppm: 1.08 (3H, t, J=7.0 Hz), 1.56 (3H, d, J=7.0 Hz), 2.38 (3H, s), 3.15-3.30 (2H, m), 4.90-5.00 (1H, m), 6.78 (1H, dd, J=8.8, 3.0 Hz), 7.03 (1H, d, J=3.0 Hz) 7.05-7.10 (1H, m), 7.18 (1H, d, J=7.7 Hz), 7.26 (1H, d, J=8.8 Hz), 7.40-7.45 (1H, m)

Reference Example 3-21

¹H-NMR (CDCl₃) δ ppm: 1.50-1.55 (3H, m), 2.38 (3H, s), 2.70 (3H, s), 4.95-5.05 (1H, m), 6.83 (1H, dd, J=8.8, 3.0 Hz), 7.00-7.15 (2H, m), 7.19 (1H, d, J=7.9 Hz), 7.29 (1H, d, J=8.8 Hz), 7.40-7.45 (1H, m)

Reference Example 3-22

¹H-NMR (CDCl₃) δ ppm: 2.00-2.10 (1H, m), 2.35 (3H, s), 2.40-2.50 (1H, m), 2.60 (3H, s), 2.80-2.95 (1H, m), 3.00-3.10 (1H, m), 5.50 (1H, t, J=7.8 Hz), 6.67 (1H, dd, J=8.8, 3.0 Hz), 6.75 (1H, d, J=3.0 Hz), 6.90-7.10 (2H, m), 7.19 (1H, d, J=8.8 Hz)

Reference Example 3-23

¹H-NMR (CDCl₃) δ ppm: 1.95-2.05 (1H, m), 2.30-2.50 (4H, m), 2.60 (3H, s), 2.80-2.90 (1H, m), 3.00-3.10 (1H, m), 3.90 (3H, s), 5.49 (1H, t, J=7.7 Hz), 6.67 (1H, dd, J=8.8, 3.0 Hz), 6.70-6.80 (2H, m), 7.04 (1H, d, J=8.3 Hz), 7.18 (1H, t, J=8.8 Hz)

Reference Example 3-24

¹H-NMR (CDCl₃) δ ppm: 1.07 (3H, t, J=7.0 Hz), 1.50 (3H, d, J=7.0 Hz), 2.32 (3H, s), 3.05-3.25 (2H, m), 4.80-4.90 (1H, m), 6.55 (1H, dd, J=8.8, 3.0 Hz), 6.66 (1H, d, J=3.0 Hz), 7.16 (1H, d, J=8.8 Hz), 7.20-7.25 (1H, m), 7.30-7.45 (2H, m)

Reference Example 3-25

¹H-NMR (CDCl₃) δ ppm: 1.03 (3H, t, J=7.0 Hz), 1.50 (3H, d, J=6.8 Hz), 2.32 (3H, s), 3.05-3.20 (2H, m), 3.88 (3H, s), 4.85-4.95 (1H, m), 6.56 (1H, dd, J=8.8, 3.0 Hz), 6.66 (1H, d, J=3.0 Hz), 6.83 (1H, d, J=8.5 Hz), 7.10-7.20 (2H, m), 7.45-7.50 (1H, m)

Reference Example 3-26

¹H-NMR (CDCl₃) δ ppm: 1.05 (3H, t, J=7.0 Hz), 1.51 (3H, d, J=6.8 Hz), 2.32 (3H, s), 3.00-3.25 (2H, m), 4.80-4.95 (1H, m), 6.56 (1H, dd, J=8.8, 3.0 Hz), 6.66 (1H, d, 3=3.0 Hz), 7.00-7.25 (3H, m), 7.40-7.55 (1H, m)

Reference Example 3-28

¹H-NMR (CDCl₃) δ ppm: 1.06 (3H, t, J=7.0 Hz), 1.51 (3H, d, J=6.8 Hz), 2.32 (3H, s), 3.05-3.20 (2H, m), 4.80-4.95 (1H, m), 6.55 (1H, dd, J=8.8, 3.0 Hz), 6.65 (1H, d, J=3.0 Hz), 7.10-7.20 (2H, m), 7.37 (1H, d, J=8.3 Hz), 7.50-7.60 (1H, m)

Reference Example 3-29

¹H-NMR (CDCl₃) δ ppm: 1.54 (3H, d, J=7.0 Hz), 2.71 (3H, s), 4.95-5.05 (1H, m) 6.83 (1H, dd, J=8.8, 3.0 Hz), 7.06 (1H, d, J=3.0 Hz), 7.10-7.20 (1H, m), 7.31 (1H, d, J=8.8 Hz), 7.41 (1H, d, J=8.5 Hz) 7.50-7.55 (1H, m)

Reference Example 3-30

¹H-NMR (CDCl₃) δ ppm: 1.10 (3H, t, J=7.0 Hz), 1.57 (3H, d, J=6.8 Hz), 3.15-3.30 (2H, m), 4.85-5.00 (1H, m), 6.78 (1H, dd, J=8.8, 3.0 Hz), 7.04 (1H, d, J=3.0 Hz), 7.10-7.20 (1H, m), 7.28 (1H, d, J=8.8 Hz), 7.40 (1H, d, J=8.3 Hz), 7.50-7.55 (1H, m)

Reference Example 3-37

¹H-NMR (CDCl₃) δ ppm: 1.60 (3H, d, J=6.8 Hz), 2.39 (3H, s), 2.80 (3H, s), 5.05-5.20 (1H, m), 6.88 (1H, dd, J=8.8, 2.8 Hz), 7.00-7.10 (2H, m), 7.21 (1H, d, J=8.0 Hz), 7.35-7.45 (1H, m), 7.60 (1H, d, J=8.8 Hz)

Reference Example 3-46

¹H-NMR (CDCl₃) δ ppm: 1.43 (1H, t, J=5.4 Hz), 1.56 (3H, d, J=6.8 Hz), 2.38 (3H, s), 3.20-3.70 (4H, m), 4.85-5.00 (1H, m), 6.85-6.95 (1H, m), 7.05-7.25 (3H, m), 7.30 (1H, d, J=8.8 Hz), 7.40-7.50 (1H, m)

Reference Example 3-47

¹H-NMR (CDCl₃) δ ppm: 2.10-2.25 (1H, m), 2.33 (3H, s), 2.40-2.55 (1H, m), 2.80-2.90 (1H, m), 2.95-3.30 (3H, m), 3.55-3.70 (2H, m), 5.30-5.40 (1H, m), 6.71 (1H, dd, J=8.8, 2.8 Hz), 6.81 (1H, d, J=2.8 Hz), 6.90-7.00 (1H, m), 7.07 (1H, dd, J=8.1, 4.7 Hz), 7.18 (1H, d, J=8.8 Hz)

Reference Example 3-50

¹H-NMR (CDCl₃) δ ppm: 1.48 (3H, d, J=6.8 Hz), 2.33 (3H, s), 2.37 (3H, s), 3.05-3.30 (2H, m), 3.45-3.60 (2H, m), 4.75-4.90 (1H, m), 6.68 (1H, dd, J=8.5, 3.0 Hz), 6.79 (1H, d, J=3.0 Hz), 7.05-7.25 (3H, m), 7.40-7.50 (1H, m)

Reference Example 3-53

¹H-NMR (CDCl₃) δ ppm: 1.52 (3H, d, J=6.8 Hz), 2.31 (3H, s), 2.37 (3H, s), 3.20-3.50 (7H, m), 4.85-4.95 (1H, m), 6.59 (1H, dd, J=8.8, 3.0 Hz), 6.70 (1H, d, J=3.0 Hz), 7.05-7.20 (3H, m), 7.40-7.50 (1H, m)

Reference Example 3-54

MS (ESI, m/z): 414(M+H)⁺

Reference Example 4-1

1-[(4-Chloro-3-methylphenyl)(ethyl)amino]indan-4-carbonitrile

To a mixture of (4-bromoindan-1-yl)-(4-chloro-3-methylphenyl)(ethyl)amine (Reference Example 3-12)(2.46 g), zinc cyanide (1.43 g) and N-methylpyrrolidone (20 mL) was added tetrakistriphenylphosphinepalladium (779 mg), and the mixture was stirred at an external temperature of 105° C. for 18 hours. The mixture was cooled to room temperature. After the mixture was diluted with ethyl acetate, the resulting mixture was washed with water and brine successively, and concentrated under reduced pressure. The residue was purified by column chromatography on silica gel (eluent: 2%-10% ethyl acetate/hexane, gradient elution) to give the title compound (1.96 g). The structural formula was illustrated in Table 4.

Reference Example 4-2 and Reference Example 4-3

Reference Example 4-2 and Reference Example 4-3 were synthesized in a similar manner to that described in Reference Example 4-1 using Reference Example 3-27 and Reference Example 3-45 instead of Reference Example 3-12. The structural formula was illustrated in Table 4.

TABLE 4

| Reference Example | Structural formula |
|---|---|
| 4-1 | 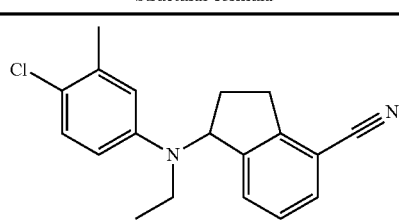 |

TABLE 4-continued

| Reference Example | Structural formula |
|---|---|
| 4-2 | (4-chloro-3-methylphenyl)(ethyl)amino-(3-cyanophenyl)methanol structure |
| 4-3 | 4-chloro-3-(trifluoromethyl)phenyl-(ethyl)amino-(4-methyl-3-cyanophenyl)methanol structure |

The physical data of Reference Example 4-1 to Reference Example 4-3 were shown below.

Reference Example 4-1

MS (ESI, m/z): 311(M+H)$^+$

Reference Example 4-2

MS (ESI, m/z): 315(M+H)$^+$

Reference Example 4-3

MS (ESI, m/z): 383(M+H)$^+$

Reference Example 5-1

3-{(R)-1-[(4-Chloro-3-methylphenyl)(ethyl)amino]ethyl}benzonitrile

Step 1

To a mixture of 3-(R)-1-aminoethyl)benzonitrile (750 mg), 1-chloro-4-iodo-2-methylbenzene (1.94 g), L-proline (177 mg) and copper (I) iodide (147 mg) and dimethylsulfoxide (4 mL) was added potassium carbonate (1.42 g), and the mixture was stirred at an external temperature of 110° C. for 23 hours. The mixture was cooled to room temperature. After the mixture was diluted with ethyl acetate, the resulting mixture was washed with water and brine successively, and concentrated under reduced pressure. The residue was purified by column chromatography on silica gel (eluent: 5%-35% ethyl acetate/hexane, gradient elution) to give 3-[(R)-1-(4-chloro-3-methylphenylamino)ethyl]benzonitrile (502 mg).

Step 2

To a mixture of 3-[(R)-1-(4-chloro-3-methylphenylamino)ethyl]benzonitrile (502 mg), acetaldehyde (5 mol/L tetrahydrofuran solution, 1.0 mL) and methanol (5 mL) was added decaborane (68 mg), and the mixture was stirred at room temperature for 1 hour. After the mixture was diluted with ethyl acetate, to the resulting mixture was added aminopropyl silica gel powder (2 g). The resulting mixture was filtered and the filtrate was concentrated under reduced pressure. The residue was purified by column chromatography on silica gel (eluent: 0%-10% ethyl acetate/hexane, gradient elution) to give the title compound (493 mg). The structural formula was illustrated in Table 5.

Reference Example 5-2

Reference Example 5-2 was synthesized in a similar manner to that described in Reference Example 5-1 using 3-((S)-1-aminoethyl)benzonitrile instead of 3-((R)-1-aminoethyl)benzonitrile. The structural formula was illustrated in Table 5.

TABLE 5

| Reference Example | Structural formula |
|---|---|
| 5-1 | (R)-3-{1-[(4-chloro-3-methylphenyl)(ethyl)amino]ethyl}benzonitrile structure |
| 5-2 | (S)-3-{1-[(4-chloro-3-methylphenyl)(ethyl)amino]ethyl}benzonitrile structure |

The physical data of Reference Example 5-1 to Reference Example 5-2 were shown below.

Reference Example 5-1

$^1$H-NMR (CDCl$_3$) δ ppm: 1.06 (3H, t, J=7.0 Hz), 1.56 (3H, d, J=6.9 Hz), 2.32 (3H, s), 3.10-3.20 (2H, m), 4.93 (1H, q, J=6.9 Hz), 6.55 (1H, dd, J=8.8, 3.0 Hz), 6.66 (1H, d, J=3.0 Hz), 7.15 (1H, d, J=8.8 Hz), 7.40-7.45 (1H, m), 7.50-7.65 (3H, m)

Reference Example 5-2

$^1$H-NMR (CDCl$_3$) δ ppm 1.06 (3H, t, J=7.0 Hz), 1.56 (3H, d, J=6.9 Hz) 2.32 (3H, s), 3.10-3.20 (2H, m), 4.93 (1H, q, J=6.9 Hz), 6.55 (1H, dd, J=8.8, 3.0 Hz), 6.66 (1H, d, J=3.0 Hz), 7.15 (1H, d, J=8.8 Hz), 7.40-7.45 (1H, m), 7.50-7.65 (3H, m)

Reference Example 6-1

4-Bromo-5-methyl-indan-1-one

Step 1

A mixture of 2-bromo-3-methylbenzaldehyde (3.15 g), 2,2-dimethyl-[1,3]dioxane-4,6-dione (2.28 g), triethylamine (3 mL) and formic acid (2 mL) was stirred at an external temperature of 100° C. for 2 hours. The mixture was cooled to room temperature. The mixture was poured into ice water, and the resulting mixture was diluted with hydrochloric acid (2 mol/L) and ethyl acetate. The ethyl acetate layer was washed with brine, and concentrated under reduced pressure to give 3-(2-bromo-3-methylphenyl)propionic acid (3. 90 g).

Step 2

To a mixture of 3-(2-bromo-3-methylphenyl)propionic acid (3.85 g), dichloromethane (15 mL) and oxalyl dichloride (4.0 g) was added N,N-dimethylformamide (0.05 mL), and the mixture was stirred at room temperature for 2 hours. The mixture was concentrated under reduced pressure. To a mixture of the residue and dichloromethane (30 mL) was added aluminium chloride (2.64 g), and the mixture was stirred at an external temperature of 50° C. for 12 hours. The mixture was cooled to room temperature. The mixture was poured into ice water, and the resulting mixture was diluted with dichloromethane. The insoluble material was removed by filtration with Celite pad, and the dichloromethane layer of the filtrate was separated. The dichloromethane layer was washed with 0.1 mol/L sodium hydroxide aqueous solution and brine successively, and concentrated under reduced pressure. The residue was purified by column chromatography on silica gel (eluent: 0%-20% ethyl acetate/hexane, gradient elution) to give the title compound (2.59 The structural formula was illustrated in Table 6.

Reference Example 6-2 to Reference Example 6-5

Reference Example 6-2 to Reference Example 6-5 were synthesized in a similar manner to that described in Reference Example 6-1 using the corresponding commercially available benzaldehyde derivatives instead of 2-bromo-3-methylbenzaldehyde in Step 1. The structural formula was illustrated in Table 6.

Reference Example 6-6

1-(3-Bromo-4-trifluoromethylpheny)ethanone

Step 1

To a mixture of 3-bromo-4-trifluoromethylbenzaldehyde (2 g) and tetrahydrofuran (36 mL) was added methylmagnesium iodide (2 mol/L diethylether solution, 4.35 mL) under ice-cooling, and the mixture was stirred at the same temperature for 30 minutes. The mixture was diluted with ammonium chloride aqueous solution and ethyl acetate. The ethyl acetate layer was washed with brine, and concentrated under reduced pressure to give 1-(3-bromo-4-trifluoromethylphenyl-ethanol.

Step 2

To a mixture of 1-(3-bromo-4-trifluoromethylphenyl) ethanol and dichloromethane (36 mL) was added Dess-Martin periodinane (3.52 g), and the mixture was stirred at room temperature for 30 minutes. The mixture was diluted with 1 mol/L sodium hydroxide aqueous solution and ethyl acetate. The ethyl acetate layer was washed with brine, and concentrated under reduced pressure. The residue was purified by aminopropyl silica gel column chromatography (eluent: 0%-20% ethyl acetate/hexane, gradient elution) to give the title compound (890 mg). The structural formula was illustrated in Table 6.

Reference Example 6-7

Reference Example 6-7 was synthesized in a similar manner to that described in Reference Example 6-6 using 3-iodo-4-methylbenzaldehyde instead of 3-bromo-4-trifluoromethylbenzaldehyde, and using ethylmagnesium bromide instead of methylmagnesium iodide in Step 1. The structural formula was illustrated in Table 6.

Reference Example 6-8

Acetic acid 2-(3-bromo-4-methylphenyl)-2-oxoethyl ester

Step 1

To a mixture of 1-(3-bromo-4-methylphenyl)ethanone (1 g), acetic acid (5 mL) and concentrated sulfuric acid (0.1 mL) was added N-bromosuccinimide (1.0 g), and the mixture was stirred at room temperature for 2 hours. The reaction mixture was diluted with water, and the precipitated solid was collected by filtration. The obtained solid was washed with water, and dried under reduced pressure to give 2-bromo-1-(3-bromo-4-methylphenyl)ethanone.

Step 2

To a mixture of 2-bromo-1-(3-bromo-4-methylphenyl) ethanone, N,N-dimethylformamide (15 mL) was added sodium acetate (1.16 g), and the mixture was stirred at an external temperature of 70° C. for 30 minutes. The mixture was cooled to room temperature. The mixture was diluted with water and ethyl acetate. The ethyl acetate layer was washed with brine, and concentrated under reduced pressure. The residue was purified by silica gel column chromatography (eluent: 10%-20% ethyl acetate/hexane, gradient elution) to give the title compound (1.11 g). The structural formula was illustrated in Table 6.

Reference Example 6-9

5-Acetyl-2-methylbenzoic acid propyl ester

To a mixture of 1-(3-bromo-4-methylphenyl)ethanone (2.0 g), 1-propanol (50 mL), triethylamine (3.90 mL) and N-methylpyrrolidone (10 mL) were added [1,1'-bis(diphenylphosphino)ferrocene]palladium dichloride dichloromethane complex (307 mg) and 1,1'-bis(diphenylphosphino)ferrocene (208 mg), and the mixture was stirred under a carbon monoxide atmosphere at an external temperature of 110° C. for 3 hours. The mixture was cooled to room temperature. After the mixture was diluted with ethyl acetate, and the resulting mixture was washed with water, saturated sodium hydrogen carbonate aqueous solution and brine successively, and concentrated under reduced pressure to give the title compound (2.0 g). The structural formula was illustrated in Table 6.

Reference Example 6-10

5-Acetyl-2-vinylbenzoic acid ethyl ester

Step 1

To a mixture of 5-acetyl-2-hydroxybenzoic acid ethyl ester (1.0 g), pyridine (1.3 mL) and dichloromethane (30 mL) was added trifluoromethanesulfonic anhydride (1.4 mL) under ice-cooling, and the mixture was stirred at the same temperature for 20 minutes. After the mixture was diluted with ethyl acetate, the resulting mixture was washed with water, saturated sodium hydrogen carbonate aqueous solution and brine successively, and concentrated under reduced pressure to give 5-acetyl-2-trifluoromethanesulfonyloxybenzoic acid ethyl ester (953 mg).

Step 2

To a mixture of 5-acetyl-2-trifluoromethanesulfonyloxybenzoic acid ethyl ester (953 mg), tributylvinyltin (1.6 mL) and toluene (12 mL) was added [1,1'-bis(diphenylphosphino)ferrocene]palladium dichloride dichloromethane complex (229 mg), and the mixture was stirred at an external temperature of 100° C. for 12 hours. The mixture was cooled to room temperature. After the mixture was diluted with ethyl acetate, the resulting mixture was washed with 1 mol/L sodium hydroxide aqueous solution and brine successively, and concentrated under reduced pressure to give the title compound (630 mg). The structural formula was illustrated in Table 6.

TABLE 6

| Reference Example | Structural formula |
|---|---|
| 6-1 | 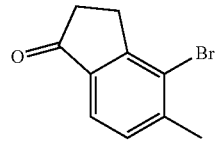 |
| 6-2 | 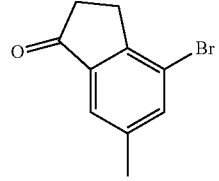 |
| 6-3 | 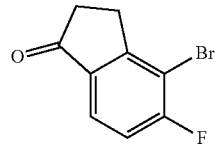 [SMILES: O=C1CCc2c1ccc(F)c2Br] |
| 6-4 | 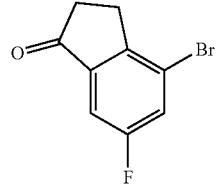 [SMILES: O=C1CCc2c(Br)cc(F)cc21] |
| 6-5 | 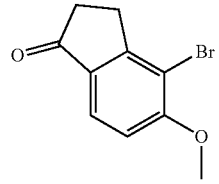 |
| 6-6 | 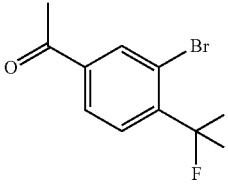 |
| 6-7 | 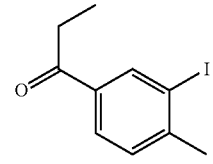 |

TABLE 6-continued

| Reference Example | Structural formula |
|---|---|
| 6-8 | 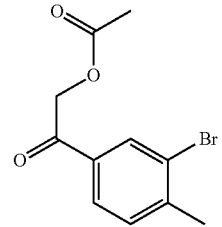 |
| 6-9 | 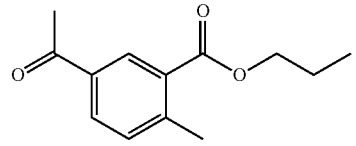 [SMILES: CCCOC(=O)c1cc(C(C)=O)ccc1C] |
| 6-10 | 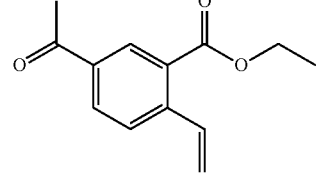 |

The physical data of Reference Example 6-1 to Reference Example 6-7 were shown below.

Reference Example 6-1

$^1$H-NMR (CDCl$_3$) δ ppm: 2.51 (3H, s), 2.65-2.80 (2H, m), 3.00-3.15 (2H, m), 7.20-7.35 (1H, m), 7.61 (1H d, J=7.8 Hz)

Reference Example 6-2

$^1$H-NMR (CDCl$_3$) δ ppm: 2.40 (3H, s), 2.65-2.80 (2H, m), 3.00-3.10 (2H, m), 7.51 (1H, s), 7.61 (1H, s)

Reference Example 6-3

$^1$H-NMR (CDCl$_3$) δ ppm: 2.70-2.80 (2H, m), 3.05-3.15 (2H, m) 7.10-7.20 (1H, m), 7.65-7.75 (1H, m)

Reference Example 6-4

$^1$H-NMR (CDCl$_3$) ppm: 2.75-2.85 (2H, m), 3.00-3.10 (2H, m), 7.38 (1H, dd, J=7.0, 2.3 Hz), 7.54 (1H, dd, J=8.0, 2.3 Hz)

Reference Example 6-5

$^1$H-NMR (CDCl$_3$) δ ppm: 2.65-2.75 (2H, m), 3.00-3.10 (2H, m) 4.00 (3H, s) 6.95 (1H, d, J=8.5 Hz) 7.72 (1H, d, J=8.5 Hz)

Reference Example 6-6

$^1$H-NMR (CDCl$_3$) δ ppm: 2.64 (3H, s), 7.80 (1H, d, J=8.0 Hz), 7.90-8.00 (1H, m) 8.26 (1H, s)

Reference Example 6-7

$^1$H-NMR (CDCl$_3$) δ ppm: 1.21 (3H, t, J=7.3 Hz), 2.48 (3H, s), 2.95 (2H, q, J=7.3 Hz), 7.31 (1H, d, J=8.0 Hz), 7.83 (1H, dd, J=8.0, 1.8 Hz), 8.38 (1H, d, J=1.8 Hz)

Example 1-1

1-3-{[(4-Chloro-3-methylphenyl)(methyl)amino]methyl}benzyl)azetidine-3-carboxylic acid methyl ester (Compound 1-1)

To a mixture of 1-{3-[(4-chloro-3-methylphenylamino)methyl]benzyl}-azetidine-3-carboxylic acid methyl ester (Reference Example 1-1) (266 mg) and methanol (5 mL) were added formaldehyde aqueous solution (37%, 0.35 mL) and decaborane (45 mg), and the mixture was stirred at room temperature for 1 hour. After the mixture was diluted with ethyl acetate, to the resulting mixture was added aminopropyl silica gel powder (5 g). The resulting mixture was filtered and the filtrate was concentrated under reduced pressure. The residue was purified by silica gel column chromatography (eluent: 50%-100% ethyl acetate/hexane, gradient elution) to give the title compound (162 mg). The structural formula was illustrated in Table 7.

Example 1-2

1-(3-{[4-Chloro-3-methylphenyl)(methyl)amino]methyl}benzyl)azetidine-3-carboxylic acid (Compound 1-2)

To a mixture of 1-(3-{[(4-chloro-3-methylphenyl)(methyl)amino]-methyl}benzyl)azetidine-3-carboxylic acid methyl ester (Example 1-1) (137 mg), 1,4-dioxane (2 mL) and methanol (2 mL) was added 2 mol/L sodium hydroxide aqueous solution (0.55 mL), and the mixture was stirred at room temperature for 2 hours. To the mixture was added 2 mol/L hydrochloric acid (0.55 mL), and concentrated under reduced pressure. The obtained residue was diluted with ethanol, and the insoluble material was removed by filtration. The filtrate was concentrated under reduced pressure to give the title compound (88 mg). The structural formula was illustrated in Table 7.

The physical data of Compound 1-1 to Compound 1-2 were shown below.

Compound 1-1
MS (ESI, m/z): 373(M+H)$^+$

Compound 1-2
$^1$H-NMR (DMSO-$d_6$) δ ppm: 2.22 (3H, s), 2.97 (3H, s), 3.10-3.70 (7H, m), 4.53 (2H, s), 6.54 (1H, dd, J=8.8, 3.0 Hz), 6.69 (1H, d, J=3.0 Hz), 7.00-7.30 (5H, m)

Example 2-1

1-(5-{[(4-Chloro-3-methylphenyl)(ethyl)amino]methyl}-2-methylbenzyl)azetidine-3-carboxylic acid (Compound 2-1)

Step 1

To a mixture of (4-chloro-3-methylphenyl)(ethyl)-(3-iodo-4-methylbenzyl)amine (Reference Example 3-1) (747 mg) and tetrahydrofuran (12 mL) was added isopropylmagnesium chloride (2 mol/L tetrahydrofuran solution, 1.9 mL) under ice-cooling, and the mixture was stirred at the same temperature for 30 minutes. To the mixture was added NN-dimethylformamide (0.72 mL), and the mixture was stirred at room temperature for 1 hour. The mixture was diluted with water and ethyl acetate. The ethyl acetate layer was washed with brine, and concentrated under reduced pressure to give 5-{[(4-chloro-3-methylphenyl)(ethyl)amino]methyl}-2-methylbenzaldehyde (400 mg).

Step 2

To a mixture of 5-{[(4-chloro-3-methylphenyl)(ethyl)amino]methyl}-2-methylbenzaldehyde (400 mg), azetidine-3-carboxylic acid methyl ester hydrochloride salt (425 mg), triethylamine (0.39 mL) and tetrahydrofuran (10 mL) was added sodium triacetoxyborohydride (1.19 g), and the mixture was stirred at room temperature for 3 hours. After the mixture was diluted with ethyl acetate, the resulting, mixture was washed with saturated sodium hydrogen carbonate aqueous solution and brine successively, and concentrated

TABLE 7

| Compound No. | Structural formula |
| --- | --- |
| 1-1 | |
| 1-2 | | under reduced pressure. The residue was purified by column chromatography on silica gel (eluent: 20%-100% ethyl acetate/hexane, gradient elution) to give 1-(5-{[(4-chloro-3-methylphenyl)(ethyl)amino]methyl}-2-methylbenzyl)azetidine-3-carboxylic acid methyl ester (267 mg).

MS (ESI, m/z): 401(M+H)$^+$

Step 3

To a mixture of 1-(5-{[(4-chloro-3-methylphenyl)(ethyl)amino]methyl}-2-methylbenzyl)azetidine-3-carboxylic acid methyl ester (242 mg), 1,4-dioxane (4 mL) and methanol (4 mL) was added 2 mol/L sodium hydroxide aqueous solution (0.91 mL), and the mixture was stirred at room temperature for 2 hours. To the mixture was added 2 mol/L hydrochloric acid (0.91 mL), and concentrated under reduced pressure. The obtained residue was diluted with ethanol, and the insoluble material was removed by filtration. The filtrate was concentrated under reduced pressure to give the title compound (216 mg). The structural formula was illustrated in Table 8.

Example 2-2 to Example 2-5 (Compound 2-2 to Compound 2-5)

Compound 2-2 to Compound 2-5 were synthesized in a similar manner to that described in Example 2-1 using the corresponding halobenzenes (Reference Example 3-2 to Reference Example 3-4, Reference Example 3-54) instead of (4-chloro-3-methylphenyl)(ethyl)-(3-iodo-4-methylbenzyl)amine (Reference Example 3-1) in Step 1. The structural formula was illustrated in Table 8.

TABLE 8

| Compound No. | Structural formula |
|---|---|
| 2-1 | (structure) |
| 2-2 | (structure) |
| 2-3 | (structure) |
| 2-4 | (structure) |
| 2-5 | (structure) |

The physical data of Compound 2-1 to Compound 2-5 were shown below.

Compound 2-1
$^1$H-NMR (DMSO-d$_6$) δ ppm: 1.09 (3H, t, J=6.9 Hz), 2.15-2.25 (6H, m), 3.10-3.55 (9H, m) 4.44 (2H, s), 6.46 (1H, dd, J=8.8, 3.0 Hz), 6.64 (1H, d, J=3.0 Hz), 6.90-7.15 (4H, m)

Compound 2-2
$^1$H-NMR (DMSO-d$_6$) δ ppm: 2.21 (3H, s), 2.22 (3H, s), 2.95 (3, s), 3.10-3.70 (7H, m), 4.49 (2H, s), 6.54 (1H, dd, J=8.8, 3.0 Hz), 6.69 (1H, d, J=3.0 Hz), 6.90-7.15 (4H, m)

Compound 2-3
$^1$H-NMR (DMSO-d$_6$) δ ppm: 1.13 (6H, d, J=6.5 Hz), 2.17 (3H, s), 2.20 (3H, s), 3.05-3.65 (7H, m), 4.15-4.30 (1H, m), 4.31 (2H, s), 6.44 (1H, dd, J=9.0, 3.0 Hz), 6.66 (1H d, J=3.0 Hz), 6.95-7.15 (4H, m)

Compound 2-4

$^1$H-NMR (DMSO-d$_6$) δ ppm: 1.10 (3H, t, J=7.0 Hz), 2.15-2.25 (6H, m), 3.15-3.70 (9H, m), 4.43 (2H, s), 6.38 (1H, dd, J=8.8, 3.0 Hz), 6.60 (1H, d, J=3.0 Hz), 6.80-7.15 (4H, m)

Compound 2-5
$^1$H-NMR (DMSO-d$_6$) δ ppm: 0.65 (3H, t, J=7.0 Hz), 1.40 (3H, d, J=6.5 Hz), 2.07 (3H, s), 2.26 (3H, s), 2.90-3.60 (9H, m), 5.10-5.25 (1H, m), 6.63 (1H, dd, J=8.8, 3.0 Hz), 6.75 (1H, d, J=3.0 Hz), 7.10-7.25 (3H, m), 7.25-7.35 (1H, m)

Example 2-6

1-(5-{1-[(4-Chloro-3-methylphenyl)(ethyl)amino]ethyl}-2-methylbenzyl)azetidine-3-carboxylic acid (Compound 2-6)

Step 1

To a mixture of [1-(3-bromo-4-methylphenyl) ethyl]-(4-chloro-3-methylphenyl)(ethyl)amine (Reference Example 3-5) (1.04 g) and tetrahydrofuran (10 mL) was added n-butyllithium (2.69 mol/L tetrahydrofuran solution, 1.16 mL) at −78° C., and the mixture was stirred at the same temperature for 30 minutes. To the mixture was added N,N-dimethylformamide (1.1 mL), and the mixture was stirred at room temperature for 20 minutes. The mixture was diluted with ammonium chloride aqueous solution and ethyl acetate. The ethyl acetate layer was washed with brine, and concentrated under reduced pressure to give 5-{1-[(4-chloro-3-methylphenyl)(ethyl)-amino]ethyl}-2-methylbenzaldehyde (623 mg).

Step 2

To a mixture of 5-{1-[(4-chloro-3-methylphenyl)(ethyl)amino]ethyl}-2-methylbenzaldehyde (623 mg), azetidine-3-carboxylic acid methyl ester hydrochloride salt (748 mg), triethylamine (0.69 mL) and tetrahydrofuran (20 mL) was added sodium triacetoxyborohydride (2.09 g), and the mixture was stirred at room temperature for 12 hours. After the mixture was diluted with ethyl acetate, the resulting mixture was washed with saturated sodium hydrogen carbonate aqueous solution and brine successively, and concentrated under reduced pressure. The residue was purified by column chromatography on aminopropyl silica gel (eluent: 0%-35% ethyl acetate/hexane, gradient elution) to give 1-(5-{1-[(4-chloro-3-methylphenyl)(ethyl)-amino]ethyl}-2-methylbenzyl)azetidine-3-carboxylic acid methyl ester (654 mg).

$^1$H-NMR (CDCl$_3$) δ ppm: 1.02 (3H, t, J=7.0 Hz), 1.53 (3H, d, J=6.8 Hz), 2.28 (3H, s), 2.31 (3H, s), 3.10-3.40 (5H, m), 3.45-3.55 (2H, m), 3.56 (2H, s), 3.71 (3H, s), 4.90-5.00 (1H, m), 6.55 (1H, dd, 3.0 Hz), 6.65 (1H, d, J=3.0 Hz), 7.00-7.20 (4H, m)

Step 3

To a mixture of 1-(5-{1-[(4-chloro-3-methylphenyl)(ethyl)amino]ethyl}-2-methylbenzyl)azetidine-3-carboxylic acid methyl ester (654 mg) and methanol (16 mL) was added 2 mol/L sodium hydroxide aqueous solution (1.2 mL), and the mixture was stirred at room temperature for 2 hours. To the mixture was added 2 mol/L hydrochloric acid (1.2 mL), and concentrated under reduced pressure. The obtained residue was diluted with ethanol, and the insoluble material was removed by filtration. The filtrate was concentrated under reduced pressure to give the title compound (610 mg). The structural formula was illustrated in Table 9.

Example 2-7

1-(5-{1-[(4-Chloro-3-trifluoromethylphenyl)(ethyl)amino]ethyl}-2-methylbenzyl)-azetidine-3-carboxylic acid (Compound 2-7)

Step 1

To a mixture of [1-(3-bromo-4-methylphenyl)ethyl]-(4-chloro-3-trifluoromethylphenyl)(ethyl)amine (Reference Example 3-20) (1.19 g) and tetrahydrofuran (15) was added n-butyllithium (2.65 mol/L tetrahydrofuran solution, 1.2 mL) at −78° C., and the mixture was stirred at the same temperature for 30 minutes. To the mixture was added NN-dimethylformamide (1.1 mL), and the mixture was stirred at room temperature for 20 minutes. The mixture was diluted with ammonium chloride aqueous solution and ethyl acetate. The ethyl acetate layer was washed with brine, and concentrated under reduced pressure to give 5-{1-[(4-chloro-3-trifluoromethylphenyl)(ethyl)amino]ethyl}-2-methylbenzaldehyde (652 mg).

Step 2

To a mixture of 5-{1-[(4-chloro-3-trifluoromethylphenyl)(ethyl)amino]ethyl}-2-methylbenzaldehyde (652 mg), azetidine-3-carboxylic acid methyl ester hydrochloride salt (669 mg), triethylamine (0.61 mL) and tetrahydrofuran (17 mL) was added sodium triacetoxyborohydride (1.87 g), and the mixture was stirred at room temperature for 12 hours. After the mixture was diluted with ethyl acetate, the resulting mixture was washed with saturated sodium hydrogen carbonate aqueous solution and brine successively, and concentrated under reduced pressure. The residue was purified by column chromatography on aminopropyl silica gel (eluent: 0%-35% ethyl acetate/hexane, gradient elution) to give 1-(5-{1-[(4-chloro-3-trifluoromethylphenyl)(ethyl)amino]ethyl}-2-methylbenzyl)azetidine-3-carboxylic acid methyl ester (628 mg).

MS (ESI, m/z): 469(M+H)$^+$

Step 3

To a mixture of 1-(5-{1-[(4-chloro-3-trifluoromethylphenyl)(ethyl)amino]-ethyl}-2-methylbenzyl) azetidine-3-carboxylic acid methyl ester (628 mg) and methanol (13 mL) was added 2 mol/L sodium hydroxide aqueous solution (1.35 mL), and the mixture was stirred at room temperature for 2 hours. To the mixture was added 2 monohydrochloric acid (1.35 mL), and concentrated under reduced pressure. The obtained residue was diluted with ethanol, and the insoluble material was removed by filtration. The filtrate was concentrated under reduced pressure to give the title compound (570 mg). The structural formula was illustrated in Table 9.

Example 2-8

1-{1-[(4-Chloro-3-trifluoromethylphenyl)(ethyl)amino]-5-methylindan-4-ylmethyl}azetidine-3-carboxylic acid (Compound 2-8)

Step 1

To a mixture of (4-bromo-5-methylindan-1-yl)-(4-chloro-3-trifluoromethyl-phenyl)(ethyl)amine (Reference Example 3-32) (665 mg) and tetrahydrofuran (7.5 mL) was added n-butyllithium (2.65 mol/L tetrahydrofuran solution, 0.70 mL) at −78° C., and the mixture was stirred at the same temperature for 20 minutes. To the mixture was added N,N-dimethylformamide (0.59 mL), and the mixture was stirred at room temperature for 20 minutes. The mixture was diluted with ammonium chloride aqueous solution and ethyl acetate. The ethyl acetate layer was washed with brine, and concentrated under reduced pressure to give 1-[(4-chloro-3-trifluoromethylphenyl)(ethyl)amino]-5-methylindan-4-carbaldehyde (440 mg).

Step 2

To a mixture of 1-[(4-chloro-3-trifluoromethylphenyl)(ethyl)amino]-5-methylindan-4-carbaldehyde (440 mg), azetidine-3-carboxylic acid methyl ester hydrochloride salt (437 mg), triethylamine (0.4 mL) and tetrahydrofuran (12 mL) was added sodium triacetoxyborohydride (1.22 g), and the mixture was stirred at room temperature for 12 hours. After the mixture was diluted with ethyl acetate, the resulting mixture was washed with saturated sodium hydrogen carbonate aqueous solution and brine successively, and concentrated under reduced pressure. The residue was purified by column chromatography on aminopropyl silica gel (eluent: 0%-35% ethyl acetate/hexane, gradient elution) to give 1-{1-[(4-chloro-3-trifluoromethylphenyl)(ethyl)amino]-5-methylindan-4-ylmethyl}aztidine-3-carboxylic acid methyl ester (446 mg).

Step 3

To a mixture of 1-{1-[(4-chloro-3-trifluoromethylphenyl)(ethyl)amino]-5-methylindan-4-ylmethyl}azetidine-3-carboxylic acid methyl ester (446 mg) and methanol (9 mL) was added 2 mol/L sodium hydroxide aqueous solution (0.93 mL), and the mixture was stirred at room temperature for 2 hours. To the mixture was added 2 mol/L hydrochloric acid (0.93 mL), and concentrated under reduced pressure. The obtained residue was diluted with ethanol, and the insoluble material was removed by filtration. The filtrate was concentrated under reduced pressure to give the title compound (320 mg). The structural formula was illustrated in Table 9.

Example 2-9 to Example 2-51 (Compound 2-9 to Compound 2-51)

Compound 2-9 to Compound 2-51 were synthesized in a similar manner to that described in Example 2-8 using the corresponding halobenzenes (Reference Example 3-6 to Reference Example 3-11, Reference Example 3-13 to Reference Example 3-19, Reference Example 3-21 to Reference Example 3-26, Reference Example 3-28 to Reference Example 3-31, Reference Example 3-33 to Reference Example 3-44, Reference Example 3-46 to Reference Example 3-53) instead of (4-bromo-5-methylindan-1-yl)-(4-chloro-3-trifluoromethylphenyl)(ethyl)amine (Reference Example 3-32) in Step 1. The structural formula was illustrated in Table 9.

TABLE 9

| Compound No. | Structural formula |
|---|---|
| 2-6 | |
| 2-7 | |
| 2-8 | |
| 2-9 | |

TABLE 9-continued

| Compound No. | Structural formula |
|---|---|
| 2-10 | |
| 2-11 | |
| 2-12 | |
| 2-13 | |
| 2-14 | |
| 2-15 | |

TABLE 9-continued

| Compound No. | Structural formula |
|---|---|
| 2-16 | |
| 2-17 | |
| 2-18 | |
| 2-19 | |
| 2-20 | |
| 2-21 | |

TABLE 9-continued

| Compound No. | Structural formula |
|---|---|
| 2-22 | |
| 2-23 | |
| 2-24 | |
| 2-25 | |
| 2-26 | |

TABLE 9-continued

| Compound No. | Structural formula |
| --- | --- |
| 2-27 | |
| 2-28 | |
| 2-29 | |
| 2-30 | |
| 2-31 | |
| 2-32 | |

TABLE 9-continued
| Compound No. | Structural formula |
|---|---|
| 2-33 | 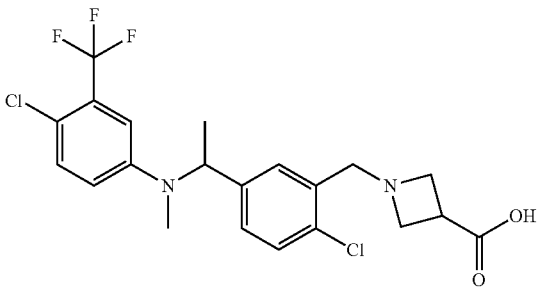 [SMILES: Cc1ccc(C(C)N(C)c2ccc(Cl)c(C(F)(F)F)c2)cc1CN1CC(C(=O)O)C1] |
| 2-34 | 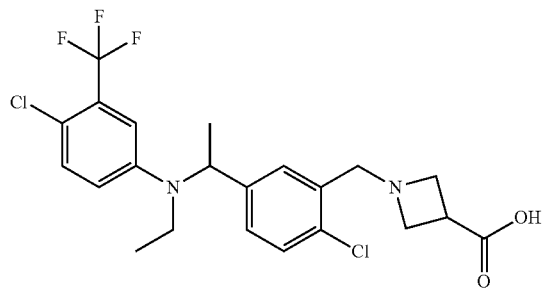 [SMILES: CCN(c1ccc(Cl)c(C(F)(F)F)c1)C(C)c1ccc(Cl)c(CN2CC(C(=O)O)C2)c1] |
| 2-35 | 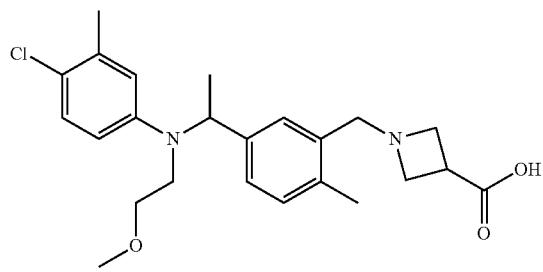 [SMILES: COCCN(c1ccc(Cl)c(C)c1)C(C)c1ccc(C)c(CN2CC(C(=O)O)C2)c1] |
| 2-36 | 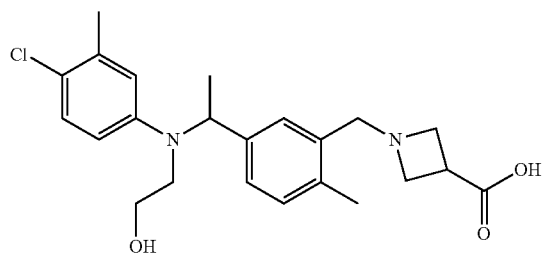 [SMILES: Cc1cc(N(CCO)C(C)c2ccc(C)c(CN3CC(C(=O)O)C3)c2)ccc1Cl] |
| 2-37 | 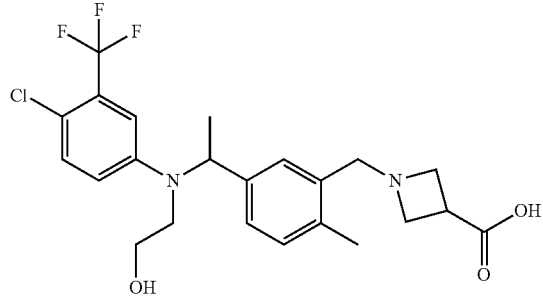 [SMILES: Cc1ccc(C(C)N(CCO)c2ccc(Cl)c(C(F)(F)F)c2)cc1CN1CC(C(=O)O)C1] |

TABLE 9-continued

| Compound No. | Structural formula |
|---|---|
| 2-38 | |
| 2-39 | |
| 2-40 | |
| 2-41 | |
| 2-42 | |

TABLE 9-continued

| Compound No. | Structural formula |
|---|---|
| 2-43 | |
| 2-44 | |
| 2-45 | |
| 2-46 | |
| 2-47 | |
| 2-48 | |

TABLE 9-continued

| Compound No. | Structural formula |
|---|---|
| 2-49 | 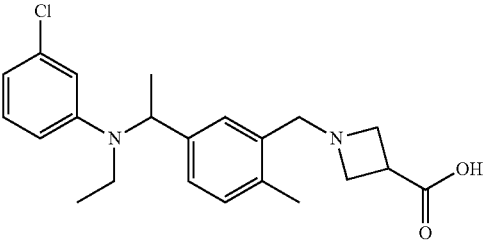 [SMILES: CCN(c1cccc(Cl)c1)C(C)c1ccc(C)c(CN2CC(C(=O)O)C2)c1] |
| 2-50 | 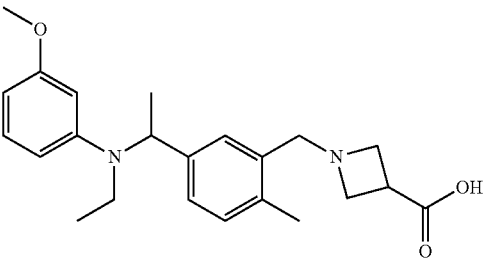 [SMILES: CCN(c1cccc(OC)c1)C(C)c1ccc(C)c(CN2CC(C(=O)O)C2)c1] |
| 2-51 | 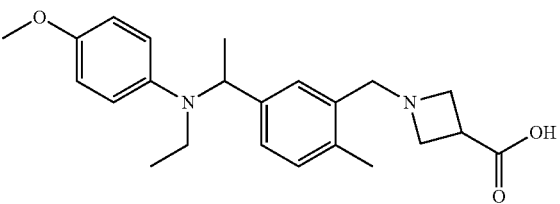 [SMILES: CCN(c1ccc(OC)cc1)C(C)c1ccc(C)c(CN2CC(C(=O)O)C2)c1] |

The physical data of Compound 2-6 to Compound 2-51 were shown below.

Compound 2-6

$^1$H-NMR (DMSO-d$_6$) ppm: 0.95 (3H, t, J=7.0 Hz), 1.47 (3H, d, J=6.8 Hz), 2.21 (3H, s), 2.23 (3H, s), 3.10-3.55 (9H, m), 5.02 (1H, q, J=6.8 Hz), 6.58 (1H, dd, J=8.8, 3.0 Hz), 6.75 (1H, d, J=3.0 Hz), 7.00-7.15 (4H, m)

Compound 2-7

$^1$H-NMR (DMSO-d$_6$) δ ppm: 1.00 (3H, t, J=7.0 Hz), 1.52 (3H, d, J=6.8 Hz), 2.21 (3H, s), 3.10-3.55 (9H, m), 5.11 (1H, q, J=6.8 Hz), 6.95-7.20 (5H, m), 7.38 (1H, d, J=9.2 Hz)

Compound 2-8

$^1$H-NMR (DMSO-d$_6$) δ ppm: 1.00 (3H, t, J=7.0 Hz), 1.85-2.00 (1H, m), 2.30-2.50 (4H, m) 2.80-2.95 (1H, m), 3.00-3.60 (10H, m), 5.45 (1H, t, J=7.8 Hz), 6.88 (1H, d, J=7.8 Hz), 6.99 (1H, d. J=7.8 Hz), 7.00-7.10 (2H, m), 7.35-7.45 (1H, m)

Compound 2-9

$^1$H-NMR (DMSO-d$_6$) δ ppm: 1.75-1.90 (1H, m), 2.20-2.55 (10H, m), 2.65-2.80 (1H, m), 2.85-3.00 (1H, m), 3.15-3.55 (7H, m), 5.48 (1H, t, J=7.8 Hz), 6.70-6.80 (2H, m), 6.89 (1H, d, J=3.01 Hz), 6.95-7.00 (1H, m), 7.17 (1H, d, J=8.8 Hz)

Compound 2-10

$^1$H-NMR (DMSO-d$_6$) δ ppm: 1.75-1.95 (1H, m), 2.30-2.45 (4H, m), 2.58 (3H, s), 2.80-2.95 (1H, m), 3.00-3.60 (8H, m), 5.58 (1H, t, J=7.8 Hz), 6.87 (1H, d, J=7.8 Hz), 7.01 (1H, d, J=7.8 Hz), 7.15-7.25 (2H, m), 7.45 (1H, d, J=9.5 Hz)

Compound 2-11

$^1$H-NMR (DMSO-d$_6$) δ ppm: 1.08 (3H, t, J=7.0 Hz), 2.20 (3H, s), 2.28 (3H, s), 2.32 (3H, s), 3.10-3.70 (9H, m), 4.38 (2H, s), 6.38 (1H, dd, J=8.8, 3.0 Hz), 6.58 (1H, d, J=3.0 Hz), 6.74 (1H, d, J=7.8 Hz), 6.89 (1H, d, J=7.8 Hz), 7.07 (1H, d, J=8.8 Hz)

Compound 2-12

$^1$H-NMR (DMSO-d$_6$) δ ppm: 0.80-1.00 (6H, m), 1.80-2.10 (2H, m), 2.25 (3H, s), 3.00-3.60 (9H, m), 4.80-4.90 (1H, m), 6.66 (1H, dd, J=9.0, 3.0 Hz), 6.80 (1H, d, J=3.0 Hz), 7.05-7.30 (5H, m)

Compound 2-13

$^1$H-NMR (DMSO-d$_6$) δ ppm: 1.44 (3H, d, J=7.0 Hz), 2.21 (3H, s), 2.2.5 (3H, s), 2.58 (3H, s), 3.05-3.55 (7H, m), 5.05-5.15 (1H, m), 6.66 (1H, dd, J=8.8, 3.0 Hz), 6.80 (1H, d, J=3.0 Hz), 7.02 (1H, dd, J=7.8, 1.8 Hz), 7.05-7.15 (3H, m)

Compound 2-14

$^1$H-NMR (DMSO-d$_6$) δ ppm: 0.75 (3H, t, J=7.3 Hz), 1.25-1.50 (5H, m), 2.21 (3H, s), 2.23 (3H, s), 2.90-3.50 (9H, m), 4.95-5.10 (1H, m), 6.57 (1H, dd, J=9.0, 3.0 Hz), 6.73 (1H, d, J=3.0 Hz), 6.95-7.15 (4H, m)

Compound 2-15

$^1$H-NMR (DMSO-d$_6$) δ ppm: 0.98 (3H, t, J=7.0 Hz), 1.85-2.05 (1H, m), 2.25 (3H, s), 2.35-2.45 (1H, m), 2.75-2.90 (1H, m), 2.95-3.60 (10H, m), 5.40 (1H, t, J=7.8 Hz), 6.65 (1H, dd, J=9.0, 3.0 Hz), 6.81 (1H, d, J=3.0 Hz), 6.95-7.05 (2H, m), 7.13 (1H, d, J=9.0 Hz)

Compound 2-16

$^1$H-NMR (DMSO-d$_6$) δ ppm: 1.00 (3H, t, J=7.0 Hz), 1.85-2.05 (1H, m), 2.20-2.55 (4H, m), 2.60-2.80 (1H, m), 2.85-3.60 (10H, m), 5.41 (1H, t, J=7.8 Hz), 6.60-6.75 (2H, m), 6.81 (1H, d, J=3.0 Hz), 6.90-7.00 (1H, m), 7.14 (1H, d, J=8.8 Hz)

Compound 2-17

¹H-NMR (DMSO-d₆) δ ppm: 1.75-1.95 (1H, m), 2.25-3.60 (16H, m), 5.53 (1H, t, J=7.8 Hz), 6.77 (1H, dd, J=8.8, 3.0 Hz), 6.85-7.00 (2H, m), 7.10-7.20 (3H, m)

Compound 2-18

¹H-NMR (DMSO-d₆) δ ppm: 0.98 (3H, t, J=7.0 Hz), 1.80-1.95 (1H, m), 2.25 (3H, s), 2.30-2.45 (1H, m), 2.70-2.90 (1H, m), 2.90-3.60 (10H, m), 3.76 (3H, s), 5.35 (1H, t, J=7.8 Hz), 6.64 (1H, dd, J=8.8, 3.0 Hz), 6.80 (1H, d, J=3.0 Hz), 6.83 (1H, d, J=8.3 Hz), 6.96 (1H, d, J=8.3 Hz), 7.13 (1H, d, J=8.8 Hz)

Compound 2-19

¹H-NMR (DMSO-d₆) δ ppm: 0.73 (3H, t, J=7.3 Hz), 1.30-1.50 (2H, m), 1.85-2.00 (1H, m), 2.24 (3H, s), 2.30-2.45 (1H, m), 2.65-3.60 (11H, m), 5.40 (1H, t, J=7.8 Hz), 6.63 (1H, dd, J=8.8, 3.0 Hz), 6.79 (1H, d, J=3.0 Hz), 6.90-7.00 (1H, m), 7.05-7.20 (3H, m)

Compound 2-20

¹H-NMR (DMSO-d₆) δ ppm: 1.85-2.00 (1H, m), 2.24 (3H, s), 2.30-2.45 (1H, m), 2.65-2.85 (1H, m), 2.90-3.60 (12H, m), 4.50-4.70 (1H, m), 5.42 (1H, t, J=7.8 Hz), 6.70 (1H, dd, J=8.8, 3.0 Hz), 6.85 (1H, d, J=3.0 Hz), 6.90-7.00 (1H, m), 7.05-7.20 (3H, m)

Compound 2-21

¹H-NMR (DMSO-d₆) δ ppm: 0.97 (3H, t, J=7.0 Hz), 1.80-1.95 (1H, m), 2.24 (3H, s), 2.30-2.45 (4H, m), 2.75-2.90 (1H, m), 2.95-3.60 (10H, m), 5.37 (1H, t, J=7.8 Hz), 6.64 (1H, dd, J=8.8, 3.0 Hz), 6.80 (1H, d, J=3.0 Hz), 6.88 (1H, d, J=7.8 Hz), 6.98 (1H, d, J=7.8 Hz), 7.12 (1H, d, J=8.8 Hz)

Compound 2-22

¹H-NMR (DMSO-d₆) δ ppm: 0.99 (3H, t, J=7.0 Hz), 1.80-2.00 (1H, m), 2.20-2.45 (7H, m), 2.60-2.80 (1H, m), 2.85-3.60 (10H, m), 5.37 (1H, t, J=7.8 Hz), 6.64 (1H, dd, J=9.0, 3.0 Hz), 6.77 (1H, s), 6.80 (1H, d, J=3.0 Hz), 6.96 (1H, s), 7.13 (1H, d, J=9.0 Hz)

Compound 2-23

¹H-NMR (DMSO-d₆) δ ppm: 1.80-1.95 (1H, m), 2.30-2.45 (1H, m), 2.60 (3H, s), 2.70-2.85 (1H, m), 2.90-3.60 (8H, m), 5.63 (1H, t, J=7.8 Hz), 6.90-7.00 (1H, m), 7.10-7.25 (4H, m), 7.45 (1H, d, J=8.5 Hz)

Compound 2-24

¹H-NMR (DMSO-d₆) δ ppm: 1.02 (3H, t, J=7.0 Hz), 1.85-2.05 (1H, m), 2.35-150 (1H, m), 2.70-2.90 (1H, m), 2.95-3.60 (10H, m), 5.50 (1H, t, J=8.0 Hz), 6.90-7.20 (5H, m), 7.41 (1H, d, J=9.0 Hz)

Compound 2-25

¹H-NMR (DMSO-d₆) δ ppm: 1.49 (3H, d, J=6.8 Hz), 2.21 (3H, s), 2.71 (3H, s), 3.05-3.55 (7H, m), 5.10-5.25 (1H, m), 7.00-7.15 (5H, m), 7.41 (1H d, J=9.8 Hz)

Compound 2-26

¹H-NMR (DMSO-d₆) δ ppm: 1.90-2.05 (1H, m), 2.24 (3H, s), 2.30-2.50 (1H, m), 2.75-3.60 (13H, m), 5.40 (1H, t, J=7.8 Hz) 6.69 (1H, dd, J=8.8, 3.0 Hz), 6.85 (1H, d, J=3.0 Hz), 6.95-7.05 (2H, m), 7.14 (1H, d, J=8.8 Hz)

Compound 2-27

¹H-NMR (DMSO-d₆) δ ppm: 1.80-1.95 (1H, m), 2.27 (3H, s), 2.30-2.45 (1H, m), 2.45-3.60 (12H, m), 5.52 (1H, t, J=7.8 Hz), 6.77 (1H, dd, J=8.8, 3.0 Hz), 6.91 (1H, d, J=3.0 Hz), 6.95-7.05 (2H, m), 7.17 (1H, d, J=8.8 Hz)

Compound 2-28

¹H-NMR (DMSO-d₆) δ ppm: 1.75-1.90 (1H, m), 2.25-2.40 (4H, m), 2.45-3.60 (12H, m), 3.76 (3H, s), 5.46 (1H, t, J=7.8 Hz), 6.75 (1H, dd, J=8.8, 3.0 Hz), 6.85 (1H, d, J=8.3 Hz), 6.89 (1H, d, J=3.0 Hz), 6.94 (1H, d, J=8.3 Hz), 7.16 (1H, d, J=8.8 Hz)

Compound 2-29

¹H-NMR (DMSO-d₆) δ ppm: 0.98 (3H, t, J=7.0 Hz), 1.49 (3H, d, J=6.8 Hz), 2.24 (3H, s), 3.10-3.55 (9H, m), 5.00-5.10 (1H, m), 6.59 (1H, dd, J=8.8, 3.0 Hz), 6.77 (1H, d, J=3.0 Hz), 7.10-7.20 (4H, m)

Compound 2-30

¹H-NMR (DMSO-d₆) δ ppm: 0.93 (3H, t, J=6.8 Hz) 1.46 (3H, d, J=6.8 Hz), 2.24 (3H, s), 3.05-3.55 (9H, m), 3.75 (3H, s), 4.95-5.10 (1H, m), 6.59 (1H, dd, J=8.8, 3.0 Hz), 6.76 (1H, d, J=3.0 Hz), 6.89 (1H, d, J=8.3 Hz), 7.05-7.15 (3H, m)

Compound 2-31

¹H-NMR (DMSO-d₆) δ ppm: 0.95 (3H, t, J=7.0 Hz), 1.48 (3H, d, J=6.8 Hz), 2.23 (3H, s), 3.05-3.55 (9H, m), 5.00-5.10 (1H, m), 6.60 (1H, dd, J=8.8, 3.0 Hz), 6.76 (1H, d, J=3.0 Hz), 7.05-7.30 (4H, m)

Compound 2-32

¹H-NMR (DMSO-d₆) δ ppm: 0.98 (3H, t, J=7.0 Hz), 1.49 (3H, d, J=6.8 Hz), 2.23 (3H, s), 3.10-3.60 (9H, m), 5.00-5.10 (1H, m), 6.59 (1H, dd, J=9.0, 3.0 Hz), 6.76 (1H, d, J=3.0 Hz), 7.11 (1H, d, J=9.0 Hz), 7.15 (1H dd, J=8.3, 2.0 Hz), 7.30 (1H, d, J=2.0 Hz), 7.35 (1H, d, J=8.3 Hz)

Compound 2-33

¹H-NMR (DMSO-d₆) δ ppm: 1.50 (3H, d, J=6.8 Hz), 2.74 (3H, s), 3.10-3.65 (7H, m), 5.15-5.30 (1H, m), 7.05-7.15 (2H, m), 7.16 (1H, dd, J=8.3, 2.0 Hz), 7.29 (1H, d J=2.0 Hz), 7.35-7.50 (2H, m)

Compound 2-34

¹H-NMR (DMSO-d₆) δ ppm: 1.03 (3H, t, J=7.0 Hz), 1.54 (3H, d, J=6.8 Hz), 3.10-3.65 (9H, m), 5.10-5.25 (1H, m), 6.95-7.05 (2H, m), 7.16 (1H, dd, J=8.3, 2.0 Hz), 7.30 (1H, d, J=2.0 Hz), 7.35-7.45 (2H, m)

Compound 2-35

¹H-NMR (DMSO-d₆) δ ppm: 1.47 (3H, d, J=6.8 Hz), 2.21 (3H, s), 2.22 (3H, s), 3.05-3.55 (14H, m), 4.95-5.10 (1H, m), 6.60 (1H, dd, J=8.8, 3.0 Hz), 6.78 (1H, d, J=3.0 Hz), 6.95-7.15 (4H, m)

Compound 2-36

¹H-NMR (DMSO-d₆) δ ppm: 1.47 (3H, d, J=6.8 Hz), 2.21 (3H, s), 2.22 (3H, s), 3.05-3.60 (11H, m), 4.95-5.10 (1H, m), 6.61 (1H, dd, J=8.8, 3.0 Hz), 6.79 (1H, d, J=3.0 Hz), 6.95-7.15 (4H, m)

Compound 2-37

¹H-NMR (DMSO-d₆) δ ppm: 1.52 (3H, d, J=6.8 Hz), 2.21 (3H, s), 3.00-3.60 (11H, m), 5.00-5.15 (1H, m), 6.95-7.20 (5H, m), 7.30-7.45 (1H, m)

Compound 2-38

¹H-NMR (DMSO-d₆) δ ppm: 1.53 (3H, d, J=6.8 Hz), 2.22 (3H, s), 3.00-3.60 (14H, m), 5.00-5.15 (1H, m), 6.95-7.15 (5H, m), 7.37 (1H, d, J=9.0 Hz)

Compound 2-39

¹H-NMR (DMSO-d₆) δ ppm: 1.85-2.05 (1H, m), 2.30-2.55 (4H, m), 2.80-2.95 (1H, m), 3.00-3.70 (12H, m), 4.65-4.80 (1H, m), 5.35-5.50 (1H, m), 6.80-7.25 (4H, m), 7.40 (1H, d, J=8.7 Hz)

Compound 2-40

¹H-NMR (DMSO-d₆) δ ppm: 1.90-2.05 (1H, m), 2.30-2.50 (4H, m), 2.80-2.95 (1H, m), 3.05-3.60 (15H, m), 5.42 (1H, t, J=7.8 Hz), 6.87 (1H, d, J=7.8 Hz), 6.99 (1H, d, J=7.8 Hz), 7.06 (1H, dd, J=9.0, 3.0 Hz), 7.13 (1H, d, J=3.0 Hz), 7.40 (1H, d, J=9.0 Hz)

Compound 2-41

¹H-NMR (DMSO-d₆) δ ppm: 1.07 (3H, t, J=7.0 Hz), 1.59 (3H, d, J=6.8 Hz), 3.10-3.75 (9H, m), 5.15-5.30 (1H, m), 6.95-7.05 (2H, m), 7.25-7.70 (4H, m)

Compound 2-42

¹H-NMR (DMSO-d₆) δ ppm: 1.54 (3H, d, J=6.8 Hz), 2.78 (3H, s) 3.10-3.75 (7H, m), 5.25-5.40 (1H, m), 7.05-7.15 (2H, m), 7.25-7.70 (4H, m)

Compound 2-43

¹H-NMR (DMSO-d₆) δ ppm: 1.02 (3H, t, J=7.0 Hz), 1.53 (3H, d, J=6.8 Hz), 2.23 (3H, s), 3.10-3.75 (9H, m), 5.05-5.20 (1H, m), 6.59 (1H, dd, J=8.8, 3.0 Hz), 6.77 (1H, d, J=3.0 Hz), 7.12 (1H, d, J=8.8 Hz), 7.32 (1H, d, J=8.3 Hz), 7.55 (1H, s), 7.63 (1H, d, J=8.3 Hz)

Compound 2-44

¹H-NMR (DMSO-d₆) δ ppm: 1.53 (3H, d, J=6.8 Hz), 2.22 (3H, s), 2.81 (3H, s), 3.05-3.55 (7H, m), 5.30-5.45 (1H, m), 7.00-7.20 (5H, m), 7.79 (1H, d, J=8.8 Hz)

Compound 2-45

¹H-NMR (DMSO-d₆) δ ppm: 0.80-1.00 (6H, m), 1.85-2.15 (2H, m), 2.21 (3H, s), 3.05-3.55 (9H, m), 4.90 (1H, t, J=7.3 Hz) 7.00-7.20 (5H, m), 7.39 (1H, d, J=9.0 Hz)

Compound 2-46

¹H-NMR (DMSO-d₆) δ ppm: 0.80-1.00 (6H, m), 1.80-2.10 (2H, m), 2.21 (3H, s), 2.24 (3H, s), 3.00-3.60 (9H, m), 4.79 (1H, t, J=7.3 Hz), 6.65 (1H, dd, J=9.0, 3.0 Hz), 6.79 (1H, d, J=3.0 Hz), 7.00-7.15 (4H, m)

Compound 2-47

¹H-NMR (DMSO-d₆) δ ppm: 0.97 (3H, t, J=7.0 Hz), 1.49 (3H, d, J=6.8 Hz), 2.22 (3H, s), 3.00-3.70 (9H, m), 4.95-5.10 (1H, m), 6.70-6.80 (2H, m), 6.95-7.20 (5H, m)

Compound 2-48

¹H-NMR (DMSO-d₆) δ ppm: 0.97 (3H, t, J=7.0 Hz), 1.48 (3H, d, J=6.8 Hz), 2.21 (3H, s), 3.00-3.60 (9H, m), 4.95-5.10 (1H, m), 6.50-6.65 (1H, m), 6.75 (2H, d, J=8.0 Hz), 7.00-7.20 (5H, m)

Compound 2-49

¹H-NMR (DMSO-d₆) δ ppm: 0.97 (3H, t, J=7.0 Hz), 1.50 (3H, d, J=6.8 Hz), 2.21 (3H, s), 3.00-3.70 (9H, m), 4.95-5.15 (1H, m), 6.55-6.75 (3H, m), 6.95-7.20 (4H, m)

Compound 2-50

¹H-NMR (DMSO-d₆) δ ppm: 0.97 (3H, t, J=7.0 Hz), 1.48 (3H, d, J=6.8 Hz), 2.21 (3H, s), 3.05-3.55 (9H, m), 3.66 (3H, s), 4.90-5.10 (1H, m), 6.15-6.30 (2H, m), 6.37 (1H, dd, J=8.3, 2.3 Hz), 6.95-7.20 (4H, m)

Compound 2-51

¹H-NMR (DMSO-d₆) δ ppm: 0.89 (3H, t, J=7.0 Hz), 1.35 (3H, d, J=6.8 Hz), 2.21 (3H, s), 2.90-3.55 (9H, m), 3.66 (3H, s), 4.60-4.75 (1H, m), 6.70-6.85 (4H, m), 7.00-7.20 (3H, m)

Example 3-1

1-(3-{[(4-Chloro-3-methylphenyl)(ethyl)amino]methyl}benzyl)azetidine-3-carboxylic acid (Compound 3-1)

Step 1

To a mixture of (3-{[(4-chloro-3-methylphenyl)(ethyl)amino]methyl}-phenyl)methanol (Reference Example 2-1) (384 mg) and dichloromethane (10 mL) was added Dess-Martin periodinane (562 mg), and the mixture was stirred at room temperature for 30 minutes. After the mixture was diluted with ethyl acetate, the resulting mixture was washed 1 mol/L sodium hydroxide aqueous solution and brine successively, and concentrated under reduced pressure to give 3-{[(4-chloro-3-methylphenyl)(ethyl)amino]methyl}benzaldehyde (347 mg).

Step 2

To a mixture of 3-{[(4-chloro-3-methylphenyl)(ethyl)amino]methyl}-benzaldehyde (347 mg), azetidine-3-carboxylic acid methyl ester hydrochloride salt (457 mg), triethylamine (0.42 mL) and tetrahydrofuran (8 mL) was added sodium triacetoxyborohydride (1.28 g), and the mixture was stirred at room temperature for 3 hours. After the mixture was diluted with ethyl acetate, the resulting mixture was washed with saturated sodium hydrogen carbonate aqueous solution and brine successively, and concentrated under reduced pressure. The residue was purified by column chromatography on silica gel (eluent: 20%100% ethyl acetate/hexane, gradient elution) to give 1-(3-{[(4-chloro-3-methylphenyl)(ethyl)amino]methyl}benzyl)-azetidine-3-carboxylic acid methyl ester (407 mg).

MS (ESI, m/z): 387(M+H)⁺

Step 3

To a mixture of 1-(3-{[(4-chloro-3-methylphenyl)(ethyl)amino]methyl}-benzyl)azetidine-3-carboxylic acid methyl ester (372 mg), 1,4-dioxane (3 mL) and methanol (3 mL) was added 2 mol/L sodium hydroxide aqueous solution (0.72 mL), and the mixture was stirred at room temperature for 2 hours. To the mixture was added 2 mol/L hydrochloric acid (0.72 mL), and concentrated under reduced pressure. The obtained residue was diluted with ethanol, and the insoluble material was removed by filtration. The filtrate was concentrated under reduced pressure to give the title compound (344 mg). The structural formula was illustrated in Table 10.

Example 3-2 to Example 3-14 (Compound 3-2 to Compound 3-14)

Compound 3-2 to Compound 3-14 were synthesized in a similar manner to that described in Example 3-1 using the corresponding benzyl alcohols (Reference Example 2-2 to Reference Example 2-10, Reference Example 2-13 to Reference Example 2-16) instead of (3-{[(4-chloro-3-methylphenyl)(ethyl)amino]methyl}phenyl)methanol (Reference Example 2-1) in Step 1. The structural formula was illustrated in Table 10.

TABLE 10

| Compound No. | Structural formula |
|---|---|
| 3-1 | 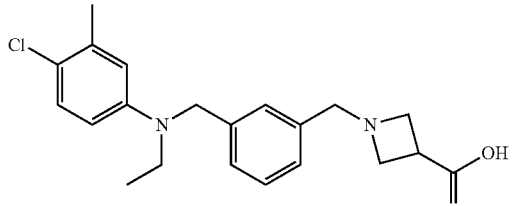 |
| 3-2 | 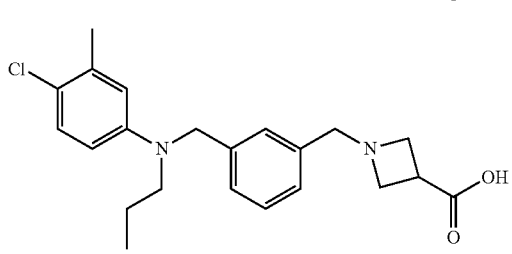 [SMILES: CCCN(Cc1cccc(CN2CC(C(=O)O)C2)c1)c1ccc(Cl)c(C)c1] |
| 3-3 | 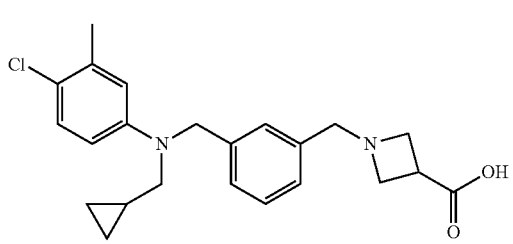 [SMILES: Cc1cc(N(Cc2cccc(CN3CC(C(=O)O)C3)c2)CC2CC2)ccc1Cl] |

TABLE 10-continued

| Compound No. | Structural formula |
|---|---|
| 3-4 | 4-chloro-3-methylphenyl-N-isopropyl, benzyl-azetidine-3-carboxylic acid |
| 3-5 | 4-chloro-3-methylphenyl-N-(2,2,2-trifluoroethyl), benzyl-azetidine-3-carboxylic acid |
| 3-6 | 4-chloro-3-methylphenyl-N-cyclobutyl, benzyl-azetidine-3-carboxylic acid |
| 3-7 | 4-chloro-3-methylphenyl-N-ethyl, tetrahydronaphthyl-azetidine-3-carboxylic acid |
| 3-8 | 4-chloro-3-(trifluoromethyl)phenyl-N-ethyl, benzyl-azetidine-3-carboxylic acid |
| 3-9 | 4-chloro-3-methoxyphenyl-N-ethyl, benzyl-azetidine-3-carboxylic acid |
| 3-10 | 3-chloro-4-methylphenyl-N-ethyl, benzyl-azetidine-3-carboxylic acid |
| 3-11 | 3,4-dimethylphenyl-N-ethyl, benzyl-azetidine-3-carboxylic acid |
| 3-12 | 3,4-dichlorophenyl-N-ethyl, benzyl-azetidine-3-carboxylic acid |
| 3-13 | 3,4,5-trichlorophenyl-N-ethyl, benzyl-azetidine-3-carboxylic acid |
| 3-14 | 4-chloro-3,5-dimethylphenyl-N-ethyl, benzyl-azetidine-3-carboxylic acid |

The physical data of Compound 3-1 to Compound 3-14 were shown below.

Compound 3-1

¹H-NMR (DMSO-d₆) δ ppm: 1.09 (3H, t, J=6.9 Hz), 2.20 (3H, s), 3.10-3.15 (9H, m), 4.48 (2H, s), 6.46 (1H, dd, J=9.0, 3.0 Hz), 6.64 (1H, d, J=3.0 Hz), 7.00-7.30 (5H, m)

Compound 3-2

¹H-NMR (DMSO-d₆) δ ppm 0.87 (3H t, J=7.3 Hz), 1.50-1.55 (2H, m), 2.19 (3H, s), 3.10-3.55 (9H, m), 4.51 (2H, s), 6.45 (1H, dd, J=8.8, 2.5 Hz), 6.62 (1H, d, J=2.5 Hz), 7.00-7.30 (5H, m)

Compound 3-3

¹H-NMR (DMSO-d₆) δ ppm: 0.15-0.25 (2H, m), 0.40-0.50 (2H, m), 1.00-1.15 (1H, m), 2.20 (3H, s), 3.10-3.55 (9H, m), 4.58 (2H, s), 6.50 (1H, dd, J=8.8, 3.0 Hz), 6.69 (1H, d, J=3.0 Hz), 7.00-7.30 (5H, m)

Compound 3-4

¹H-NMR (DMSO-d₆) δ ppm: 1.13 (6H, d, J=6.5 Hz), 2.18 (3H, s), 3.10-3.55 (7H, m), 4.15-4.30 (1H, m), 4.35 (2H, m), 6.44 (1H, dd, J=9.0, 3.0 Hz), 6.67 (1H, d, J=3.0 Hz), 7.00-7.30 (5H, m)

Compound 3-5

¹H-NMR (DMSO-d₆) δ ppm: 2.19 (3H, s), 3.10-3.60 (7H, m), 4.30-4.45 (2H, m), 4.66 (2H, s), 6.61 (1H, dd, J=8.8, 3.0 Hz), 6.83 (1H, d, J=3.0 Hz) 7.00-7.30 (5H, m)

Compound 3-6

¹H-NMR (DMSO-d₆) δ ppm: 1.55-1.70 (2H, m), 1.90-2.05 (2H, m), 2.15-2.30 (5H, m), 3.10-3.60 (7H, m), 4.10-4.25 (1H, m), 4.49 (2H, s), 6.46 (1H, dd, J=8.8, 3.0 Hz), 6.63 (1H, d, J=3.0 Hz), 7.00-7.30 (5H, m)

Compound 3-7

¹H-NMR (DMSO-d₆) δ ppm: 1.04 (3H, t, J=7.0 Hz), 1.70-2.05 (4H, m), 2.23 (3H, s), 2.55-2.70 (1H, m), 2.80-2.90 (1H, m), 2.90-3.65 (9H, m), 5.00-5.10 (1H, m), 6.59 (1H, dd, J=9.0, 2.8 Hz), 6.76 (1H, d, J=2.8 Hz), 6.90-7.15 (4H, m)

Compound 3-8

¹H-NMR (DMSO-d₆) δ ppm: 1.14 (3H, t, J=7.0 Hz), 3.20-3.75 (9H, m), 4.58 (2H, s), 6.85-7.40 (7H, m)

Compound 3-9

¹H-NMR (DMSO-d₆) δ ppm: 1.12 (3H, t, J=7.0 Hz), 3.10-3.55 (9H, m), 3.71 (3H, s), 4.51 (2H, s), 6.21 (1H, dd, J=8.7, 2.8 Hz), 6.33 (1H, d, J=2.8 Hz), 7.00-7.30 (5H, m)

Compound 3-10

¹H-NMR (DMSO-d₆) δ ppm: 1.10 (3H, t, J=7.0 Hz), 2.15 (3H, s), 3.15-3.65 (9H, m), 4.47 (2H, s), 6.54 (1H, dd, J=8.6, 2.8 Hz), 6.62 (1H, d, J=2.8 Hz), 7.00-7.30 (5H, m)

Compound 3-11

¹H-NMR (DMSO-d₆) δ ppm: 1.07 (3H, t, J=7.0 Hz), 2.05 (3H, s), 2.10 (3H, s), 3.05-3.55 (9H, m), 4.42 (2H, s), 6.35-6.55 (2H, m), 6.80-7.30 (5H, m)

Compound 3-12

¹H-NMR (DMSO-d₆) δ ppm: 1.11 (3H, t, J=7.0 Hz), 3.20-3.70 (9H, m), 4.53 (2H, s), 6.62 (1H, dd, J=9.3, 3.0 Hz), 6.79 (1H, d, J=3.0 Hz), 7.05-7.35 (5H, m)

Compound 3-13

¹H-NMR (DMSO-d₆) δ ppm: 1.11 (3H, t, J=7.0 Hz), 3.00-4.00 (9H, m), 4.57 (2H, s), 6.83 (2H, s), 7.10-7.35 (4H, m)

Compound 3-14

¹H-NMR (DMSO-d₆) δ ppm: 1.08 (3H, t, J=7.0 Hz), 2.20 (6H, s), 3.25-3.55 (9H, m), 4.46 (2H, s), 6.50 (2H, s), 7.00-7.15 (3H, m), 7.20-7.30 (1H, m)

Example 4-1

1-(5-{1-[(4-Chloro-3-trifluoromethylphenyl)(ethyl)amino]ethyl}-2-vinylbenzyl)-azetidine-3-carboxylic acid (Compound 4-1)

Step 1

To a mixture of (5-{1-[(4-chloro-3-trifluoromethylphenyl)(ethyl)amino]ethyl}-2-vinylphenyl)methanol (Reference Example 2-12) (614 mg), triethylamine (0.40 mL) and tetrahydrofuran (12 mL) was added methanesulfonyl chloride (0.19 mL) under ice-cooling, and the mixture was stirred at the same temperature for 30 minutes. After the mixture was diluted with ethyl acetate, the resulting mixture was washed saturated sodium hydrogen carbonate aqueous solution and brine successively, and concentrated under reduced pressure to give methanesulfonic acid 5-{1-[(4-chloro-3-trifluoromethylphenyl)(ethyl)amino]ethyl}-2-vinylbenzyl ester (760 mg).

Step 2

To a mixture of methanesulfonic acid 5-{1-[(4-chloro-3-trifluoromethylphenyl)(ethyl)amino]ethyl}-2-vinylbenzyl ester (760 mg), azetidine-3-carboxylic acid methyl ester hydrochloride salt (364 mg), N,N-diisopropylethylamine (0.98 mL) and acetonitrile (14 mL) was added sodium iodide (120 mg), and the mixture was stirred at an external temperature of 50° C. for 50 minutes. The mixture was cooled to room temperature. After the mixture was diluted with ethyl acetate, and the resulting mixture was washed with water, saturated sodium hydrogen carbonate aqueous solution and brine successively, and concentrated under reduced pressure. The residue was purified by column chromatography on silica gel (eluent: 15%-60% ethyl acetate/hexane, gradient elution) to give 1-(5-{1-[(4-chloro-3-trifluoromethylphenyl)(ethyl)amino]ethyl}-2-vinylbenzyl)azetidine-3-carboxylic acid methyl ester (695 mg).

MS (ESI, m/z): 481(M+H)⁺

Step 3

To a mixture of 1-(5-{1-[(4-chloro-3-trifluoromethylphenyl)(ethyl)amino]-ethyl}-2-vinylbenzyl)azetidine-3-carboxylic acid methyl ester (122 mg), 1,4-dioxane (2 mL) and methanol (2 mL) was added 2 mol/L sodium hydroxide aqueous solution (0.25 mL), and the mixture was stirred at room temperature for 2 hours. To the mixture was added 2 mol/L hydrochloric acid (0.25 mL), and concentrated under reduced pressure. The obtained residue was diluted with ethanol, and the insoluble material was removed by filtration. The filtrate was concentrated under reduced pressure to give the title compound (115 mg). The structural formula was illustrated in Table 11.

Example 4-2 to Example 4-3 (Compound 4-2 to Compound 4-3)

Compound 4-2 to Compound 4-3 were synthesized in a similar manner to that described in Example 4-1 using the corresponding benzyl alcohols (Reference Example 2-11 and Reference Example 2-17) instead of (5-{1-[(4-chloro-3-trifluoromethylphenyl)(ethyl)amino]ethyl}-2-vinylphenyl)methanol (Reference Example 2-12) in Step 1. These structural formulae were illustrated in Table 11.

TABLE 11

| Compound No. | Structural formula |
|---|---|
| 4-1 | (structure: 4-chloro-3-trifluoromethylphenyl-N(ethyl)-CH(CH₃)- attached to a benzene ring bearing a vinyl group and a CH₂-azetidine-3-carboxylic acid) |
| 4-2 | (structure: 3,5-bis(trifluoromethyl)phenyl-N(ethyl)-CH(CH₃)- attached to a methyl-substituted benzene bearing a CH₂-azetidine-3-carboxylic acid) |
| 4-3 | (structure: 4-chloro-3-methylphenyl-N(ethyl)-CH₂- attached to a cyano-substituted benzene bearing a CH₂-azetidine-3-carboxylic acid) |

The physical data of Compound 4-1 to Compound 4-3 were shown below.

Compound 4-1

$^1$H-NMR (DMSO-d$_6$) δ ppm 1.02 (3H, t, J=6.9 Hz), 1.55 (3H, d, J=7.0 Hz), 3.10-3.70 (9H, m), 5.14 (1H, q, J=7.0 Hz), 5.25-5.35 (1H, m), 5.65-5.75 (1H, m), 6.95-7.55 (7H, m)

Compound 4-2

$^1$H-NMR (DMSO-d$_6$) δ ppm: 1.01 (3H, t, J=7.0 Hz), 1.56 (3H, d, J=6.8 Hz), 2.23 (3H, s), 3.10-3.60 (9H, m), 5.26 (1H, q, J=6.8 Hz), 7.05-7.25 (6H, m)

Compound 4-3

$^1$H-NMR (DMSO-d$_6$) δ ppm 1.11 (3H, t, J=7.0 Hz), 2.21 (3H, s), 3.15-3.50 (7H, m), 3.74 (2H, s), 4.66 (2H, s), 6.44 (1H, dd, J=9.0, 3.0 Hz), 6.66 (1H, d, J=3.0 Hz), 7.05-7.20 (2H, m), 7.35-7.45 (1H, m), 7.50-7.60 (1H, m), 12.4 (1H, br s)

Example 5-1

1-(5-{1-[(4-Chloro-3-trifluoromethylphenyl)(ethyl)amino]ethyl}-2-hydroxymethyl-benzyl)azetidine-3-carboxylic acid (Compound 5-1)

Step 1

To a mixture of 1-(5-{1-[(4-chloro-3-trifluoromethylphenyl)(ethyl)amino]-ethyl}-2-vinylbenzyl)azetidine-3-carboxylic acid methyl ester (290 mg) obtained in Step 2 of Example 4-1, 4-methylmorpholine N-oxide (4.8 mol/L aqueous solution, 0.31 mL), water (4 mL) and tetrahydrofuran (8 mL) was added osmium tetroxide (2.5 wt % tert-butanol solution, 0.39 mL), and the mixture was stirred at room temperature for 1 hour. To the mixture was added sodium periodate (387 mg), and the mixture was stirred at room temperature for 30 minutes. After the mixture was diluted with ethyl acetate, the resulting mixture was washed saturated sodium hydrogen carbonate aqueous solution and brine successively, and concentrated under reduced pressure to give 1-(5-{1-[(4-chloro-3-trifluoromethylphenyl)(ethyl)-amino]ethyl}-2-formylbenzyl) azetidine-3-carboxylic acid methyl ester (290 mg).

Step 2

To a mixture of 1-(5-{1[(4-chloro-3-trifluoromethylphenyl)(ethyl)amino]-ethyl}-2-formylbenzyl)azetidine-3-carboxylic acid methyl ester (290 mg) and methanol (8 mL) was added sodium borohydride (23 mg) under ice-cooling, and the mixture was stirred at the same temperature for 20 minutes. After the mixture was diluted with ethyl acetate, the resulting mixture was washed with saturated sodium hydrogen carbonate aqueous solution and brine successively, and concentrated under reduced pressure. The residue was purified by column chromatography on silica gel (eluent: 50%-100% ethyl acetate/hexane, gradient elution) to give 1-(5-{1-[(4-chloro-3-trifluoromethylphenyl)(ethyl)amino]ethyl}-2-hydroxymethylbenzyl)azetidine-3-carboxylic acid methyl ester (180 mg).

MS (ESI, m/z): 485(M+H)$^+$

Step 3

To a mixture of 1-(5-{1-[(4-chloro-3-trifluoromethylphenyl)(ethyl)amino]-ethyl}-2-hydroxymethyl benzyl)azetidine-3-carboxylic acid methyl ester (180 mg), 1,4-dioxane (3 mL) and methanol (3 mL) was added 2 mol/L sodium hydroxide aqueous solution (0.37 mL), and the mixture was stirred at room temperature for 2 hours. To the mixture was added 2 mol/L hydrochloric acid (0.37 mL), and concentrated under reduced pressure. The obtained residue was diluted with ethanol, and the insoluble material was removed by filtration. The filtrate was concentrated under reduced pressure to give the title compound (170 mg). The structural formula was illustrated in Table 12.

TABLE 12

| Compound No. | Structural formula |
|---|---|
| 5-1 | (structure shown) |

The physical data of Compound 5-1 was shown below.
Compound 5-1
$^1$H-NMR (DMSO-d$_6$) δ ppm: 1.00 (3H, t, J=7.0 Hz), 1.54 (3H, d, J=6.8 Hz), 3.10-3.65 (9H, m), 4.40-4.55 (2H, m), 5.14 (1H, q, J=6.8 Hz), 6.95-7.45 (6H, m)

Example 6-1

1-(3-{1-[(4-Chloro-3-methylphenyl)(ethyl)amino]-2-hydroxyethyl}benzyl)azetidine-3-carboxylic acid (Compound 6-1)

Step 1

To a mixture of 3-{1-[(4-chloro-3-methylphenyl)(ethyl)amino]-2-hydroxyethyl}benzonitrile (Reference Example 4-2) (257 mg) and dichloromethane (6 mL) was added diisobutylaluminium hydride (1 mol/L hexane solution, 2.0 mL) under ice-cooling, and the mixture was stirred at the same temperature for 50 minutes. The mixture was diluted with 1 mol/L hydrochloric acid and ethyl acetate. The ethyl acetate layer was washed with saturated sodium hydrogen carbonate aqueous solution and brine successively, and concentrated under reduced pressure to give 3-{1-[(4-chloro-3-methylphenyl)(ethyl)amino]-2-hydroxyethyl}benzaldehyde (259 mg).

Step 2

To a mixture of 3-{1-[(4-chloro-3-methylphenyl)amino]-2-hydroxyethyl}benzaldehyde (259 mg), azetidine-3-carboxylic acid methyl ester hydrochloride salt (186 mg), triethylamine (0.17 mL) and tetrahydrofuran (6 mL) was added sodium triacetoxyborohydride (519 mg), and the mixture was stirred at room temperature for 15 hours. After the mixture was diluted with ethyl acetate, the resulting mixture was washed with saturated sodium hydrogen carbonate aqueous solution and brine successively, and concentrated under reduced pressure. The residue was purified by column chromatography on silica gel (eluent: 0%-20% methanol/ethyl acetate, gradient elution) to give 1-(3-{1-[(4-chloro-3-methylphenyl)(ethyl)amino]-2-hydroxyethyl}benzyl)azetidine-3-carboxylic acid methyl ester (267 mg).

MS (ESI, m/z): 417M+H)$^+$

Step 3

To a mixture of 1-(3-{1-[(4-chloro-3-methylphenyl)(ethyl)amino]-2-hydroxyethyl}benzyl) azetidine-3-carboxylic acid methyl ester (267 mg), 1,4-dioxane (3 mL) and methanol (3 mL) was added 2 mol/L sodium hydroxide aqueous solution (0.61 mL), and the mixture was stirred at room temperature for 2 hours. To the mixture was added 2 mol/L hydrochloric acid (0.61 mL), and concentrated under reduced pressure. The obtained residue was diluted with ethanol, and the insoluble material was removed by filtration. The filtrate was concentrated under reduced pressure to give the title compound (247 mg). The structural formula was illustrated in Table 13.

Example 6-2 to Example 6-5 (Compound 6-2 to Compound 6-5)

Compound 6-2 to Compound 6-5 were synthesized in a similar manner to that described in Example 6-1 using the corresponding cyanobenzenes (Reference Example 4-1, Reference Example 4-3, Reference Example 5-1 to Reference Example 5-2) instead of 3-{1-[(4-chloro-3-methylphenyl)(ethyl)amino]-2-hydroxyethyl}benzonitrile (Reference Example 4-2) in Step 1. The structural formula was illustrated in Table 13.

TABLE 13

| Compound No. | Structural formula |
|---|---|
| 6-1 | (structure shown) |

TABLE 13-continued

| Compound No. | Structural formula |
|---|---|
| 6-2 | (structure: 4-chloro-3-(trifluoromethyl)phenyl-N(ethyl)-CH(CH2OH)-aryl(2-methyl)-CH2-azetidine-3-COOH) |
| 6-3 | (structure: 4-chloro-3-methylphenyl-N(ethyl)-indanyl-CH2-azetidine-3-COOH) |
| 6-3 | (structure: 4-chloro-3-methylphenyl-N(ethyl)-CH(CH3)-phenyl-CH2-azetidine-3-COOH, with stereochemistry) |
| 6-5 | (structure: 4-chloro-3-methylphenyl-N(ethyl)-CH(CH3)-phenyl-CH2-azetidine-3-COOH, with opposite stereochemistry) |

The physical data of Compound 6-1 to Compound 6-5 were shown below.

Compound 6-1

$^1$H-NMR (DMSO-d$_6$) δ ppm: 0.95 (3H, t, J=6.9 Hz) 2.23 (3H, s), 3.10-3.60 (9H, m), 3.80-3.90 (1H, m), 3.90-4.00 (1H, m), 4.70-5.10 (2H, m), 6.59 (1H, dd, J=9.0, 3.0 Hz), 6.75 (1H, d, J=3.0 Hz), 7.05-7.30 (5H, m)

Compound 6-2

$^1$H-NMR (DMSO-d$_6$) δ ppm: 1.00 (3H, t, J=6.9 Hz), 2.21 (3H, s), 3.10-3.60 (9H, m), 3.80-4.00 (2H, m), 4.80-5.10 (2H, m), 6.95-7.20 (5H, m), 7.38 (1H, d, J=9.0 Hz)

Compound 6-3

$^1$H-NMR (DMSO-d$_6$) δ ppm: 0.99 (3H, t, J=6.91 Hz), 1.80-2.00 (1H, m), 2.24 (3H, s), 2.30-2.45 (1H, m), 2.70-3.60 (11H, m), 5.42 (1H, t, J=7.8 Hz), 6.65 (1H, dd, J=9.0, 3.0 Hz), 6.81 (1H, d, J=3.0 Hz), 6.90-7.00 (1H, m), 7.10-7.20 (3H, m)

Compound 6-4

$^1$H-NMR (DMSO-d$_6$) δ ppm: 0.95 (3H, t, J=7.0 Hz), 1.49 (3H, d, J=6.9 Hz), 2.23 (3H, s), 3.10-3.60 (9H, m), 5.06 (1H, q, J=6.9 Hz), 6.59 (1H, dd, J=8.8, 3.0 Hz), 6.76 (1H, d, J=3.0 Hz), 7.05-7.30 (5H, m)

Compound 6-5

$^1$H-NMR (DMSO-d$_6$) δ ppm: 0.95 (3H, t, J=7.0 Hz), 1.49 (3H, d, J=6.9 Hz), 2.23 (3H, s), 3.10-3.60 (9H, m), 5.06 (1H, q, J=6.9 Hz), 6.59 (1H, dd, J=8.8, 3.0 Hz), 6.76 (1H, d, J=3.0 Hz), 7.05-7.30 (5H, m)

Comparative Example 1

1-{5-[1-(4-Chloro-3-methylphenylamino)ethyl]-2-methylbenzyl}azetidine-3-carboxylic acid Step 1

To a mixture of 1-(3-bromo-4-methylphenyl)ethanone (1.51 g), 4-chloro-3-methylphenylamine (1.0 g) and methanol (14 mL) was added decaborane (259 mg), and the mixture was stirred at room temperature for 12 hours. After the mixture was diluted with ethyl acetate, to the resulting mixture was added aminopropyl silica gel powder (5 g). The resulting mixture was filtered and the filtrate was concentrated under reduced pressure to give [1-(3-bromo-4-methylphenyl)ethyl]-(4-chloro-3-methylphenyl)amine (1.99 g).

Step 2

To a mixture of [1-(3-bromo-4-methylphenyl)ethyl]-(4-chloro-3-methylphenyl)amine (0.19 g) and tetrahydrofuran (2.8 mL) was added n-butyllithium (2.65 mol/L tetrahydrofuran solution, 0.53 mL) at −78° C., and the mixture was stirred at the same temperature for 30 minutes. To the mixture was added N,N-dimethylformamide (0.22 mL), and the mixture was stirred at room temperature for 20 minutes. The mixture was diluted with ammonium chloride aqueous solution and ethyl acetate. The ethyl acetate layer was washed with brine, and concentrated under reduced pressure to give 5-[1-(4-chloro-3-methylphenylamino)ethyl]-2-methylbenzaldehyde (106 mg).

Step 3

To a mixture of 5-[1-(4-chloro-3-methylphenylamino)ethyl]-2-methylbenzaldehyde (106 mg), azetidine-3-carboxylic acid methyl ester hydrochloride salt (140 mg), triethylamine (0.13 mL) and tetrahydrofuran (3.6 mL) was added sodium triacetoxyborohydride (390 mg), and the mixture was stirred at room temperature for 12 hours. After the mixture was diluted with ethyl acetate, the resulting mixture was washed with saturated sodium hydrogen carbonate aqueous solution and brine successively, and concentrated under reduced pressure. The residue was purified by column chromatography on aminopropylsilica gel (eluent: 0%-40% ethyl acetate/hexane, gradient elution) to give 1-{5-[1-(4-chloro-3-methylphenylamino)ethyl]-2-methylbenzyl}azetidine-3-carboxylic acid methyl ester (95 mg).

Step 4

To a mixture of 1-{5-[1-(4-chloro-3-methylphenylamino)ethyl]-2-methyl-benzyl}azetidine-3-carboxylic acid methyl ester (95 mg) and methanol (2.5 mL) was added 2 mol/L sodium hydroxide aqueous solution (0.41 mL), and the mixture was stirred at room temperature for 2 hours. To the mixture was added 2 mol/L hydrochloric acid (0.41 mL), and concentrated under reduced pressure. The obtained residue was diluted with ethanol, and the insoluble material was removed by filtration. The filtrate was concentrated under reduced pressure to give the title compound (90 mg). The structural formula was illustrated in Table 14.

TABLE 14

| Comparative Example | Structural formula |
|---|---|
| 1 | (4-chloro-3-methylphenyl)-NH-CH(CH₃)-phenyl-CH₂-azetidine-3-COOH structure |

The physical data of Comparative Examples 1 was shown below.

$^1$H-NMR (DMSO-d$_6$) δ ppm: 1.36 (3H, t, J=6.8 Hz), 2.10 (3H, s), 2.17 (3H, s), 3.05-3.55 (7H, m), 4.30-4.45 (1H, m), 6.20 (1H, d, J=7.3 Hz), 6.29 (1H, dd, J=8.8, 2.5 Hz), 6.46 (1H, d, J=2.5 Hz), 6.93 (1H, d, J=8.8 Hz), 7.02 (1H, d, J=8.0 Hz), 7.09 (1H, dd, J=8.0, 1.8 Hz), 7.15-7.25 (1H, m)

Test Example 1

Confirmation Test of Antagonistic Activity for Human S1P$_1$ Receptor

Test compounds were tested by reduction of functional binding activity of $^{35}$S-GTP (guanosine 5'-O-[gamma-thio] triphosphate, PerkinElmer) to G protein using cell membranes expressing human S1P$_1$ (EDG-1). S1P$_1$-pcDNA3.1/V5-His-Topo vector was prepared by inserting cDNA (NM_001400) encoding human S1P$_1$ into the expression vector, pcDNA3.1/V5-His-Topo (registered trademark) (Invitrogen). Next, the above S1P$_1$-pcDNA3.1 vector was transfected into HEK293 cells by Lipofectamine2000 (registered trademark) (Invitrogen). The transfected cells were incubated with D-MEM liquid medium each containing 10% FBS (Fetal bovine serum), 100 U/mL penicillin, 100 µg/mL streptomycin and 1 mg/mL Geneticin (registered trademark) (Invitrogen) in an incubator under the condition of 5% CO$_2$ at 37° C. and Geneticin (registered mark)-resistant cell line stably expressing S1P$_1$ were obtained. The obtained stably S1P$_1$-expressing cells were incubated with D-MEM liquid medium each containing 10% FBS and 0.5 mg/mL Geneticin (registered trademark) in an incubator under the condition of 5% CO$_2$ at 37° C. The cells grown to confluence were harvested by a buffer solution containing 50 mM Tris, 2 mM EDTA (ethylmediaminetetraacetic acid) and 125 mM sodium chloride, and centrifuged at 1880×g, 4° C. for 10 minutes. After a supernatant was removed, a cell pellet was resuspended by the same buffer solution. For making cell membranes fragile, this cell suspension was frozen at −80° C. and then thawed. The cells were centrifuged at 1880×g, 4° C. for 10 minutes, and a supernatant was removed. The cell pellet was suspended by adding the same buffer solution and a fracture solution (10 mM sodium bicarbonate and 5 mM EDTA, pH 7.5) at a ratio of 2:1. The cells were fractured by subjecting the cell suspension to ultrasonication, and a cell membrane fraction was isolated by centrifugation at 1880×g, 4° C. for 10 minutes and ultracentrifugation of the supernatant at 80000×g, 4° C. for 30 minutes. A pellet of the cell membrane fraction was suspended by the fracture solution containing protease inhibitor cocktail (Roche) and stored at −80° C. until use. A protein concentration of the cell membrane fraction was determined using BCA Protein Assay Kit (Pierce) in accordance with an attached protocol.

Inhibitory activity evaluation was performed by multi-screen (registered trademark) HTS 96-well plate (Millipore) using the cell membrane fraction stably expressing S1P$_1$ obtained by the above operation. 25 µL of assay solution (50 mM Tris, 100 mM sodium chloride, 5 mM magnesium chloride, 1 mM EDTA, 1 mM DTT (dithiothreitol), 10 µM GDP (guanosine diphosphate) and 0.5% BSA (bovine serum albumin), pH 7.4), 25 µL of test compounds solution diluted by assay solution and 25 µL of the membrane fraction (0.2 µg protein/µL) were added to each well, and the mixture was gently shaken at room temperature: for 30 minutes. Then, 25 µL of $^{35}$S-GTP, and 25 µL of 50 nM S1P$_1$ receptor selective agonist (1-[4-(4-phenyl-5-trifluoromethylthiophen-2-yl-methoxy)benzyl]azetidine-3-carboxylic acid, "J. Med. Chem.", 2004, vol. 47, pp. 6662-6665, compound 18) were added to each well, respectively, and it was reacted at room temperature for 60 minutes. After the reaction, a reaction solution of each well was suction-filtered. After suction filtration, ice-colded wash solution (50 mM Tris, 100 mM sodium chloride, 5 mL magnesium chloride and 1 mM EDTA, pH 7.4) was added to each well, and moreover filters were washed by suction filtration. This wash procedure was performed three times. A bottom of the plate containing the filters was dried at 60° C. After drying, 30 µL of MicroScinti-40 (PerkinElmer) was added to each well, and the radioactivity adsorbed on the filter was determined by TopCount NXT (registered trademark) (PerkinElmer) after shaking for 30 minutes at room temperature.

The evaluation of the antagonistic activity of compounds was represented inhibitory effect of test compounds as an inhibition ratio by a percentage, based on that the radioactivity of the S1P$_1$ receptor selective agonist is 100% and the maximum inhibitory reaction of a control compound (1-({5'-[1-(4-chloro-3-methyl-phenyl)-ethylamino]-2'-fluoro-3,5-dimethyl-biphenyl-4-carbonyl}-amino)-cyclopropanecarboxylic acid, International publication No. WO2010/072712, Example EX26) is 0%. Test compounds were diluted from 10 µM of a final concentration to 0.01 nM with assay solution by common ratio of 10 times. The inhibition ratio of each concentration for test compounds was plotted on nonlinear regression curve, and the concentration for inhibition of 50% was calculated as the value of IC$_{50}$ (nM). The results were shown in Table 15.

TABLE 15

| Compound No. | IC$_{50}$ (nM) |
|---|---|
| 1-2 | 7.6 |
| 2-1 | 5.3 |
| 2-2 | 6.7 |
| 2-3 | 2.8 |
| 2-4 | 3.9 |
| 2-6 | 1.0 |
| 2-7 | 1.2 |
| 2-8 | 2.9 |
| 2-9 | 22.2 |
| 2-10 | 2.5 |
| 2-11 | 1.1 |
| 2-12 | 6.8 |
| 2-13 | 21.5 |
| 2-14 | 1.7 |
| 2-15 | 2.5 |
| 2-16 | 3.3 |
| 2-17 | 27.3 |
| 2-18 | 4.7 |
| 2-21 | 1.9 |

TABLE 15-continued

| Compound No. | IC$_{50}$ (nM) |
| --- | --- |
| 2-22 | 5.0 |
| 2-24 | 3.7 |
| 2-25 | 6.7 |
| 2-29 | 1.2 |
| 2-30 | 6.9 |
| 2-31 | 5.7 |
| 2-32 | 1.1 |
| 2-33 | 7.8 |
| 2-34 | 1.5 |
| 2-37 | 8.6 |
| 2-39 | 3.4 |
| 2-41 | 1.9 |
| 2-43 | 3.5 |
| 2-44 | 9.0 |
| 2-45 | 0.8 |
| 2-46 | 1.9 |
| 2-47 | 1.8 |
| 2-49 | 0.9 |
| 3-1 | 8.9 |
| 3-4 | 15.3 |
| 3-7 | 12.8 |
| 4-1 | 1.2 |
| 4-2 | 3.1 |
| 5-1 | 4.4 |
| 6-1 | 11.2 |
| 6-2 | 2.5 |
| 6-3 | 2.8 |
| 6-5 | 1.2 |
| Comparative Example 1 | 441 |

As the results of Test Example 1, it was shown that the compounds of the present invention exhibit a highly potent S1P$_1$ receptor antagonistic activity, compared with Comparative Example 1 wherein R$^4$ is a hydrogen atom.

Test Example 2

Confirmation Test for Reduction Effects on the Number of Lymphocytes

Reduction effects on the number of blood lymphocytes by test compounds were confirmed using Male Sprague-Dawley rats (Japan SLC, 7-weeks-old in use). Administration solutions for test compounds were prepared on hot-plate at 50° C. After test compounds were dissolved by DMSO (dimethyl sulfoxide, Wako Pure Chemicals) of 1/10 volume of the total volume, WellSolve (Celeste) of 1/10 volume of the total volume was added to this solution. Further, distilled water (Otsuka Pharmaceutical Factory) of 8/10 volume of the total volume was added to this solution, and the administration solutions for test compounds were prepared. A solution, prepared in the same volume ratios of DMSO. WellSolve and distilled water as the administration solution for test compounds, was used as a solvent (Vehicle). Vehicle or test compound was administered orally to rats at 1 mL/body. After 6, 24 and 48 hours from administration of vehicle or test compounds, rats were held on the board at supine position under inhalation anesthesia with isoflurane (Abbott Japan). Blood samples (200 to 250 μL) were collected from the cervical vein of this rat using 1 mL syringes with needles of 25G. The collected blood samples were transferred to a microtube treated with EDTA-2K (Japan Becton Dickinson), and stored at room temperature after gently mixing with inversion. The number of lymphocytes was measured by ADVIA (registered mark) (Bayer), which is a multi-parameter automated blood cell counter using this blood samples. The average number of lymphocytes in vehicle-treated group (vehicle group) was defined as 100%, and the average number of lymphocytes in each test compound-treated group was calculated as % of vehicle. As Comparative Example 2, 1-{5-[1-(4-chloro-3-methyl-phenyl)-propylamino]-2-methyl-benzyl}-azetidine-3-carboxylic acid (patent literature 1, Example 4) was evaluated as well. The results were shown in Table 16.

TABLE 16

| Compound No. | mg/kg | Number of lymphocytes (% of Vehicle) | | |
| --- | --- | --- | --- | --- |
| | | After 6 hours | After 24 hours | After 48 hours |
| 2-6 | 10 | 9.9 | 14.1 | 65.7 |
| 2-7 | 1 | 15.0 | 11.1 | 66.8 |
| | 10 | 10.9 | 10.6 | 13.2 |
| 2-8 | 1 | 15.1 | 34.5 | 87.7 |
| | 10 | 13.7 | 12.3 | 33.4 |
| Comparative Example 2 | 1 | 39.9 | 82.3 | 109.6 |
| | 10 | 16.8 | 94.0 | 110.3 |

As the results of Test Example 2, the compounds of the present invention were decreased the number of lymphocytes even after 24 and 48 hours from administration of test compounds while Comparative Example 2 had a transient reduction of the number of lymphocytes in blood. It was shown that compounds of the present invention exhibit continuous lymphopenia, compared with Comparative Example 2.

Test Example 3

Confirmation Test for Reduction Effects on Heart Rate

Effects on heart rate of a test compound and fingolimod, which is an S1P$_1$ receptor agonist, were confirmed using male guinea pigs (Japan SLC, 5 to 8-weeks-old in use). Guinea pigs were incised in the median line of cervical region under anesthesia with pentobarbital (Kyoritsu Pharmaceutical) by intraperitoneal administration. A PE90 catheter filled with saline (Otsuka Pharmaceutical Factory) containing 50 units/mL heparin (Mochida Pharmaceutical) was inserted to right common carotid artery. By holding the insertion site of the catheter with silk sutures, it was performed to avoid bleeding from the insertion site and to fix the catheter. After it was confirmed that blood flow reached into the catheter, an apical end of catheter opposite to the insertion site of artery was connected to pressure transducer, and blood pressure and heart rate were measured via a strain pressure amplifier and a heart rate counter unit, respectively.

The test compound or fingolimod was dissolved with DMSO, and administered. Also, DMSO was used as a solvent (vehicle).

After it was confirmed that blood pressure and heart rate were stabilized in guinea pigs, vehicle, the test compound or fingolimod was administered into the vein of penis at 0.25 mL/kg using 1 mL syringes with needles of 27G. The changes of blood pressure and heart rate were measured every 5 minutes after administration of vehicle, the test compound or fingolimod. The result of time course on heart rate was shown in FIG. 1.

As the result of Test Example 3, fingolimod, which is an S1P$_1$ receptor agonist, showed remarkable reduction of heart rate at low dose (0.03 mg/kg). Meanwhile the compound of the present invention, which is an S1P$_1$ receptor antagonist, did not have reduction of heart rate even at high dose (30 mg/kg). Therefore, it was shown that the compounds of the present invention do not induce bradycardia.

Test Example 4

The Drug Efficiency Evaluation in Naïve T Cells—Transferred Colitis Model (1) Purification of CD45RB Positive Naïve T Cells and Transfer the Cells into SCID Mice After female BALB/c mice (Charles River Japan, 8-weeks-old in use) were sacrificed by blood removal from cervical vein under inhalation anesthesia with isoflurane spleens were harvested from these mice. Spleens were washed with ice-cold PBS (phosphate buffered saline, Invitrogen) and stored in 50 mL tube containing PBS on ice. Spleens stored on ice were mashed with the upper portion of slide glasses inside a biological safety cabinet, and filtered through a cell filter (pore size 70 μm), and the filtrate was centrifuged at 500×g, room temperature for 5 minutes. After the supernatant was removed, 12 mL of RBC lysis buffer (Biolegend) was added to a cell pellet and it was resuspended and left for about 3 minutes. The supernatant was removed after centrifugation and the hemolytic process was performed by repeating same procedure once again.

The cells were purified with Mouse Naive T cell $CD4^+/CD62L^+/CD44^{low}$ Colum Kit (R&D systems). The cells performed with the hemolytic process, were suspended by column buffer attached to the above Column Kit, and purified through a cell filter (pore size 70 μm) after centrifugation at 500×g, room temperature for 5 minutes. The cells were resuspended with column buffer, and antibody cocktails attached to the above Column Kit were added to this and mixed. After that, the cells were purified according to the protocol of the Column Kit.

Next, purification of CD45RB positive cells was performed by MACS (registered mark) separator (Miltenyi Biotec). The purified cells were suspended with 2 mL of PBS containing 0.5% BSA, and reacted at room temperature for 15 minutes after adding FITC (fluorescein isothiocyanate)-labeled anti-CD45RB antibody (Biolegend). After washing two times with PBS containing 0.5% BSA by centrifugation, the cells were resuspended with 2 mL of PBS containing 0.5% BSA and reacted at room temperature for 10 minutes after adding anti-FITC microbeads (Miltenyi Biotec). After washing one time with PBS containing 0.5% BSA by centrifugation, the cells were resuspended with 3 mL of PBS containing 0.5% BSA, and a fraction of CD45RB positive cells was purified according to the protocol of MACS (registered trademark) separator. In the process of elution after detached from MACS (registered trademark) separator, the cells were separated with 5 mL of PBS. The cell suspension was washed one time by centrifugation with PBS, resuspended by appropriate PBS and measured the cell number as naïve T cells suspension for transfer. Female CB17/Icr-scid/scid Jcl (SCID mice) (Charles River Japan, 8-weeks-old in use) were induced colitis by intraperitoneal administration of 500 μL (divided into 250 μL two times) of naïve T cells suspension prepared at $6 \times 10^5$ cells/mL by PBS.

(2) Measurement of Body Weight and Procedure for Administration of Drugs

Body weights were measured at day 1, 8 and 15 as day 0 when naïve T cells were transferred to mice. Mice were grouped evenly, based on body weight change at day 15. The measurement of body weight was performed two times a week after day 15. A solvent (Vehicle) and test compounds were administered twice a day from the evening of day 15. The administration solution was prepared as indicated below. Firstly, 0.5% methyl cellulose (Wako pure chemicals) of 1/10 volume of total volume was added to test compound, and a suspension was prepared by sonication. Only if test compound is Compound No. 2-7, after 0.5% methyl cellulose (Wako pure chemicals) of 1/10 volume of total volume was added, a suspension was prepared by adding an equal molar hydrochloric acid. After that, administration solutions for test compounds were prepared by sonication while adding distilled water of 9/10 volume of of total volume to these suspensions in several batches. A solution prepared in the same volume ratios of 0.5% methyl cellulose and distilled water as administration solutions for test compounds was used as vehicle. Administration solutions for vehicle or test compounds were orally administered to mice at 5 mL/kg.

(3) Collection of Colon Tissues

The measurement of body weight and condition of feces based on the dirtying around the anus (with or without diarrhea and bloody stool) were confirmed on day 30. Mice were collected blood from the abdominal large vein under anesthesia of diethyl ether (Wako Pure Chemicals). After death from exsanguination, whole colons from anus to the appendix were collected. The collected colons were took photos on the seat with scale marks. The colons from anus to 7 cm were cut, and washed with saline. The feces in the colons were washed out using a metallic sound, and then the colons were cut open longitudinally. After the colons were washed with saline again, saline attached to the colons was wiped off using a paper towel, and the weights of the colons were measured.

(4) Evaluation by Disease Activity Index (DAI)

Three parameters of loss of body weight, colon weight, and stool consistency/condition of feces, were scored and calculated a sum of scores as DAI (minimum: 0 points, maximum: 11 points).

Change of body weight: They were scored as over 100% (0 points), 95-100% (1 point), 90-95% (2 points), 85-90% (3 points) and below 85% (4 points) as body weight at start of administration (day 15) is 100%.

Colon weight: About the colon weight measured in the above (3), they were scored as below 200 mg (0 points), 200 to 250 mg (1 point), 250 to 300 mg (2 points), and over 300 mg (3 points).

Condition of feces: They were scored as normal (0 points), feces slightly crumbling shape (1 point), no observation of normal feces (2 points), based on the photograph taken in the above (3). Furthermore, diarrhea (1 point) and bloody stool (1 point) were added as score, based on the advance confirmation of the dirtying around the anus. Each evaluation parameters represented as that average of vehicle-treated group (vehicle group) is 100%, and the results of each compound-treated group were indicated by mean±standard error as % of vehicle. The results were shown in Table 17.

TABLE 17

| Group | Case | mg/kg | Body weight change ratio (%) | DAI score (%) | Colon weight (%) |
|---|---|---|---|---|---|
| Normal group | 7 | — | 6.1 ± 1.1 | 0 | 0 |
| Control group | 14 | — | −8.6 ± 3.4 | 100.0 ± 12.0 | 100.0 ± 10.9 |
| Compound 2-6 | 14 | 15 | 1.7 ± 1.1** | 24.3 ± 11.8*** | 36.8 ± 17.1** |
| Compound 2-7 | 16 | 15 | 1.6 ± 1.2** | 22.1 ± 14.8*** | 32.4 ± 14.2** |
| 5-Aminosalicylic acid | 15 | 50 | −8.4 ± 2.6 | 72.1 ± 17.1 | 75.9 ± 58.3 |
| Prednisclone | 15 | 1.5 | −10.4 ± 1.4 | 104.4 ± 20.0 | 58.3 ± 18.9 | mean ± standard error,
**p < 0.01,
***p < 0.001 vs control group (t-test)

As the result of Test Example 4, compounds of the present invention had significantly improvement effects on all evaluation parameters of body weight change ratio DAI score and colon weight. It was shown that compounds of the present invention show more efficativeness than existing medicines in the colitis model.

Test Example 5

The Drug Efficiency Evaluation in Experimental Autoimmune Encephalomyelitis (EAE) Model An EAE model (experimental autoimmune encephalomyelitis, hereinafter referred to as EAE), which is widely used as an animal model reflecting the pathological condition of human multiple sclerosis was prepared using DA rats (Japan SLC, 8 to 9-week-old in use) as described below, and the effect of test compound was confirmed.

Firstly, the emulsion for immunization was prepared by the method described below. After rats were sacrificed by exsanguination from the carotid artery under anesthesia of isoflurane, two spinal cords and a brain were collected. On ice, 10 mL of PBS was added to collected spinal cords and a brain, and homogenates containing collected spinal cords and a brain were prepared with tissue raptor (Qiagen). After an equal volume of the complete freund's adjuvant (Thermo Fisher) was added to homogenates, the emulsion was prepared by mixing with a glass syringe. The prepared emulsion was filled in 1 mL syringes with needles of 27G, and stored on ice until use.

Under anesthesia of isoflurane, hairs on the root of tails of rats were cut with a shaver for small animals (Natsume Seisalcusho). Rats were immunized by intradermal administration of 100 μL of the previous described emulsions at two sites on the root of tail.

A solvent (Vehicle) and a test compound were administered orally twice a day from the day after immunization. Administration solutions for vehicle and the test compound were prepared as described below. Firstly, 0.5% methyl cellulose solution of 1/10 volume of total volume was added to test compound, and a suspension was prepared by adding equimolar hydrochloric acid after subjecting the mixture to sonication. After that, the administration solution for the test compound was prepared by subjecting the mixture to sonication while adding distilled water of 9/10 volume of total volume to this suspension in several batches. Administration solution for vehicle was prepared with 0.5% methyl cellulose and distilled water with the same volume ratios of administration solution for test compound. These administration solutions were administered orally from the day after immunization to day 12.

The EAE score was evaluated daily to day 13 as day 0 when DA rats were immunized. The EAE score was evaluated as 0-5 points: 0 points: no symptoms, 1 point: walkable straight with normal our limbs but complete loss of tail tonus, 2 points: slight paralysis of a limb (especially hind limbs) and walkable wobbly, 3 points: full paralysis of two limbs (especially hind limbs) and walkable with a limp, 4 points: tetraplegia, moribund or abasia, 5 points: dead.

The area under the curve was calculated based on the variation per day of EAE score during evaluation periods from immunization day 0 to day 13, and used as an index for effects of test compounds. The results were shown in Table 18.

TABLE 18

| Group | Case | mg/kg | Area under the curve of EAE score |
|---|---|---|---|
| Normal group | 7 | — | 0 |
| Control group | 14 | — | 13.3 ± 0.8 |
| Compound 2-7 | 14 | 15 | 6.1 ± 1.6*** | mean ± standard error,
***p < 0.001 vs control group (t-test)

As the results of Test Example 5, the compound of the present invention significantly decreased an area under the curve of EAE score in all evaluation periods and improved the symptoms of EAE model. Therefore it was suggested that the compounds of the present invention are useful as an agent for treatment or prevention of multiple sclerosis.

INDUSTRIAL APPLICABILITY

The compounds of the present invention have an excellent $S1P_1$ receptor antagonistic activity and thus are useful as an agent for the treatment or prevention of autoimmune diseases and the like.

The invention claimed is:
1. A compound represented by the general formula (I):

[Chem. 1]

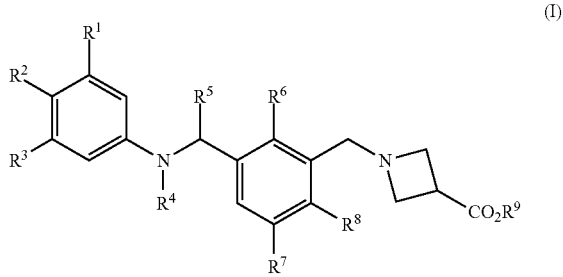

wherein
R¹, R² and R³ are each independently any one of the following a) to f):
a) a hydrogen atom,
b) a halogen atom,
c) a $C_{1-6}$ alkyl group,
d) a halo $C_{1-6}$ alkyl group,
e) a $C_{1-6}$ alkoxy, or
f) a cyano group;
R⁴ is any one of the following a) to f):
a) a $C_{1-6}$ alkyl group,
b) a halo $C_{1-6}$ alkyl group,
c) a cycloalkyl group,
d) a cycloalkyl $C_{1-6}$ alkyl group,
e) a $C_{1-6}$ alkoxy $C_{1-6}$ alkyl group, or
f) a hydroxy $C_{1-6}$ alkyl group;
R⁵ is any one of the following a) to c):
a) a hydrogen atom,
b) a $C_{1-6}$ alkyl group, or
c) a hydroxy $C_{1-6}$ alkyl group;
R⁶ is any one of the following a) to c):
a) a hydrogen atom,
b) a $C_{1-6}$ alkyl group, or
c) a cyano group,
or R⁵ and R⁶ combine to form —$(CH_2)_n$—;
R⁷ and R⁸ are each independently any one of the following a) to h):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group,
g) a $C_{2-6}$ alkenyl group, or
h) a cyano group;
R⁹ is a hydrogen atom or a $C_{1-6}$ alkyl group; and
n is 2 or 3,
or a pharmaceutically acceptable salt thereof.

2. The compound as claimed in claim 1, wherein R⁷ and R⁸ are each independently any one of the following a) to g):
a) a hydrogen atom,
b) a halogen atom,
c) a $C_{1-6}$ alkyl group,
d) a halo $C_{1-6}$ alkyl group,
e) a $C_{1-6}$ alkoxy group,
f) a hydroxy $C_{1-6}$ alkyl group, or
g) a $C_{2-6}$ alkenyl group,
or a pharmaceutically acceptable salt thereof.

3. The compound as claimed in claim 2, wherein R¹, R² and R³ are each independently any one of the following a) to e):
a) a hydrogen atom,
b) a halogen atom,
c) a $C_{1-6}$ alkyl group,
d) a halo $C_{1-6}$ alkyl group, or
e) a cyano group,
or a pharmaceutically acceptable salt thereof.

4. The compound as claimed in claim 3, wherein R⁴ is a $C_{1-6}$ alkyl group or a hydroxy $C_{1-6}$ alkyl group, or a pharmaceutically acceptable salt thereof.

5. The compound as claimed in claim 4, wherein R⁵ is any one of the following a) to c):
a) a hydrogen atom,
b) a $C_{1-6}$ alkyl group, or
c) a hydroxy $C_{1-6}$ alkyl group, and
R⁶ is any one of the following a) to b):
a) a hydrogen atom, or
b) a $C_{1-6}$ alkyl group,
or R⁵ and R⁶ combine to form —$(CH_2)_n$—,
or a pharmaceutically acceptable salt thereof.

6. The compound as claimed in claim 5, wherein R⁴ is a $C_{1-6}$ alkyl group, or a pharmaceutically acceptable salt thereof.

7. The compound as claimed in claim 6, wherein R⁷ is a hydrogen atom, R⁸ is any one of the following a) to f):
a) a halogen atom,
b) a $C_{1-6}$ alkyl group,
c) a halo $C_{1-6}$ alkyl group,
d) a $C_{1-6}$ alkoxy group,
e) a hydroxy $C_{1-6}$ alkyl group, or
f) a $C_{2-6}$ alkenyl group,
or a pharmaceutically acceptable salt thereof.

8. The compound as claimed in claim 7, wherein R¹ and R² are each independently any one of the following a) to d):
a) a halogen atom,
b) a $C_{1-6}$ alkyl group,
c) a halo $C_{1-6}$ alkyl group, or
d) a cyano group, and
R³ is a hydrogen atom,
or a pharmaceutically acceptable salt thereof.

9. The compound as claimed in claim 8, wherein R⁵ is a $C_{1-6}$ alkyl group, R⁶ is a hydrogen atom, or R⁵ and R⁶ combine to form —$(CH_2)_n$—, or a pharmaceutically acceptable salt thereof.

10. The compound as claimed in claim 9, wherein R¹ and R² are each independently any one of the following a) to c):
a) a halogen atom,
b) a $C_{1-6}$ alkyl group, or
c) a halo $C_{1-6}$ alkyl group,
or a pharmaceutically acceptable salt thereof.

11. The compound as claimed in claim 10, wherein R⁸ is any one of the following a) to c):
a) a halogen atom,
b) a $C_{1-6}$ alkyl group, or
c) a halo $C_{1-6}$ alkyl group,
or a pharmaceutically acceptable salt thereof.

12. A compound selected from the group consisting of:
1-(5{1-[(4-Chloro-3-methylphenyl(ethyl)amino]ethyl}-2-methylbenzyl)-azetidine-3-carboxylic acid;
1-(5{1-[(4-Chloro-3-trifluoromethylphenyl)(ethyl)amino]ethyl}-2-methylbenzyl)azetidine-3-carboxylic acid;
1-{1-[(4-Chloro-3-trifluoromethylphenyl)(ethyl)amino]-5-methylindan-4-ylmethyl}azetidine-3-carboxylic acid;
1-{1-[(4-Chloro-3-trifluoromethylphenyl)(methyl)amino]-5-methylindan-4-ylmethyl}azetidine-3-carboxylic acid;
1-(5-{1-[(4-Chloro-3-methylphenyl)(propyl)amino]ethyl}-2-methylbenzyl)-azetidine-3-carboxylic acid;
1-{1-[(4-Chloro-3-methylphenyl)(ethyl)amino]-5-fluoroindan-4-ylmethyl}-azetidine-3-carboxylic acid;
1-{1-[(4-Chloro-3-methylphenyl)(ethyl)amino]-5-methylindan-4-ylmethyl}-azetidine-3-carboxylic acid;
1-(5-{1-[(4-Chloro-3-trifluoromethylphenyl)(methyl)amino]ethyl}-2-methylbenzyl)azetidine-3-carboxylic acid;
1-(5-{1-[(4-Chloro-3-methylphenyl)(ethyl)amino]ethyl}-2-fluorobenzyl)-azetidine-3-carboxylic acid;
1-(2-Chloro-5-{1-[(4-chloro-3-methylphenyl)(ethyl)amino]ethyl}benzyl)-azetidine-3-carboxylic acid;

1-(2-Chloro-5-{1-[(4-chloro-3-trifluoromethylphenyl)(methyl)amino]ethyl}-benzyl)azetidine-3-carboxylic acid;

1-(2-Chloro-5-{1-[(4-chloro-3-trifluoromethylphenyl)(ethyl)amino]ethyl}-benzyl)azetidine-3-carboxylic acid;

1-(5-{1-[(4-Chloro-3-trifluoromethylphenyl)(ethyl)amino]ethyl}-2-trifluoromethylbenzyl)azetidine-3-carboxylic acid;

1-(5-{1-[(4-Chloro-3-methylphenyl)(ethyl)amino]ethyl}-2-trifluoromethyl-benzyl)azetidine-3-carboxylic acid;

1-(5-{1-[(4-Chloro-3-trifluoromethylphenyl)(ethyl)amino]propyl}-2-methyl-benzyl)azetidine-3-carboxylic acid; and 1-(5-{1-[(4-Chloro-3-methylphenyl)(ethyl)amino]propyl}-2-methylbenzyl)-azetidine-3-carboxylic acid;

or a pharmaceutically acceptable salt thereof.

13. A pharmaceutical composition comprising a compound as claimed in claim 1, or pharmaceutically acceptable salt thereof.

14. The pharmaceutical composition as claimed in claim 13, which is an agent for the treatment of a disease mediated by $S1P_1$ receptor selected from autoimmune diseases, inflammatory bowel disease, age-related macular degeneration, acute or chronic rejection on allo- or xenogeneic tissue or organ transplantation, graft-versus-host disease and cancer.

15. An agent for the treatment of a disease mediated by $S1P_1$ receptor selected from autoimmune diseases, inflammatory bowel disease, age-related macular degeneration, acute or chronic rejection on allo- or xenogeneic tissue or organ transplantation, graft-versus-host disease and cancer, comprising a compound as claimed in claim 1, or pharmaceutically acceptable salt thereof.

16. An $S1P_1$ receptor antagonist comprising a compound claimed in claim 1, or a pharmaceutically acceptable salt thereof.

* * * * *